(12) United States Patent
Haruta

(10) Patent No.: US 11,744,967 B2
(45) Date of Patent: Sep. 5, 2023

(54) INTRANASAL DELIVERY DEVICES

(71) Applicant: SHIN NIPPON BIOMEDICAL LABORATORIES, LTD., Kagoshima (JP)

(72) Inventor: Shunji Haruta, Kagoshima (JP)

(73) Assignee: SHIN NIPPON BIOMEDICAL LABORATORIES, LTD., Kagoshima (JP)

( * ) Notice: Subject to any disclaimer, the term of this patent is extended or adjusted under 35 U.S.C. 154(b) by 1117 days.

(21) Appl. No.: 16/137,852

(22) Filed: Sep. 21, 2018

(65) Prior Publication Data

US 2019/0091424 A1 Mar. 28, 2019

Related U.S. Application Data

(60) Provisional application No. 62/563,244, filed on Sep. 26, 2017.

(51) Int. Cl.
| | | |
|---|---|---|
| *A61M 15/08* | (2006.01) | |
| *B05B 11/06* | (2006.01) | |
| *A61M 11/02* | (2006.01) | |
| *B05B 11/00* | (2006.01) | |
| *A61M 15/00* | (2006.01) | |

(Continued)

(52) U.S. Cl.
CPC ........... *A61M 15/08* (2013.01); *B05B 11/061* (2013.01); *A61M 11/02* (2013.01); *A61M 15/0025* (2014.02); *A61M 16/208* (2013.01); *A61M 2202/064* (2013.01); *A61M 2205/075* (2013.01); *A61M 2210/0618* (2013.01); *B05B 11/062* (2013.01); *B05B 11/1052* (2023.01)

(58) Field of Classification Search
CPC ............ A61M 2202/064; A61M 15/08; A61M 2205/073; A61M 11/02; A61M 2205/075; A61M 2210/0618; A61M 15/0025; A61M 16/208; A61M 15/009; A61M 31/00; A61M 1/82; B05B 11/061; B05B 11/3052; B05B 11/062
See application file for complete search history.

(56) References Cited

U.S. PATENT DOCUMENTS

| | | | | |
|---|---|---|---|---|
| 2,218,983 | A | * 10/1940 | Daisley | ..................... F01L 3/14 123/188.8 |
| 3,809,084 | A | * 5/1974 | Hansen | ................ A61M 11/001 239/315 |
| 3,856,185 | A | 12/1974 | Riccio et al. | |

(Continued)

FOREIGN PATENT DOCUMENTS

| | | |
|---|---|---|
| CN | 1146729 A | 4/1997 |
| CN | 1155440 A | 7/1997 |

(Continued)

OTHER PUBLICATIONS

International Search Report and Written Opinion for International Application No. PCT/JP2018/035560 dated Nov. 6, 2018.

(Continued)

*Primary Examiner* — Victoria Murphy
(74) *Attorney, Agent, or Firm* — Wilson Sonsini Goodrich & Rosati

(57) ABSTRACT

The present disclosure provides devices for delivery of powder formulations and methods of manufacture and use of such devices.

24 Claims, 7 Drawing Sheets

Nozzle (1)

Poppet valve (2)

Retainer (3)

Pump (4)

(51) Int. Cl.
*A61M 16/20* (2006.01)
*B05B 11/10* (2023.01)

(56) References Cited

U.S. PATENT DOCUMENTS

| | | |
|---|---|---|
| 3,906,950 A | 9/1975 | Cocozza |
| 3,921,857 A * | 11/1975 | Riccio .................. B65D 83/60 |
| | | 222/145.5 |
| 4,013,075 A | 3/1977 | Cocozza |
| 4,017,007 A | 4/1977 | Riccio et al. |
| 4,159,345 A | 6/1979 | Aoyagi et al. |
| 4,200,099 A | 4/1980 | Guenzel et al. |
| 4,226,233 A | 10/1980 | Kritzer |
| 4,300,545 A | 11/1981 | Goodnow et al. |
| 4,535,808 A * | 8/1985 | Johanson ............. F16K 15/063 |
| | | 137/533.21 |
| 4,613,500 A | 9/1986 | Suzuki et al. |
| 4,889,114 A | 12/1989 | Kladders |
| 5,046,493 A | 9/1991 | Kropkowski et al. |
| 5,098,907 A | 3/1992 | Kondo et al. |
| 5,320,094 A | 6/1994 | Laube et al. |
| 5,419,315 A | 5/1995 | Rubsamen |
| 5,647,349 A | 7/1997 | Ohki et al. |
| 5,672,581 A | 9/1997 | Rubsamen et al. |
| 5,674,507 A | 10/1997 | Banker et al. |
| 5,683,361 A | 11/1997 | Elk et al. |
| 5,702,362 A | 12/1997 | Herold et al. |
| 5,731,303 A | 3/1998 | Hsieh |
| 5,756,483 A | 5/1998 | Merkus |
| 5,804,209 A | 9/1998 | De et al. |
| 5,810,004 A | 9/1998 | Ohki et al. |
| 5,939,100 A | 8/1999 | Albrechtsen et al. |
| 5,942,242 A | 8/1999 | Mizushima et al. |
| 5,948,749 A | 9/1999 | Igarashi et al. |
| 5,958,458 A | 9/1999 | Norling et al. |
| 5,989,217 A | 11/1999 | Ohki et al. |
| 6,089,228 A | 7/2000 | Smith et al. |
| 6,136,295 A | 10/2000 | Edwards et al. |
| 6,186,141 B1 | 2/2001 | Pike et al. |
| 6,197,328 B1 | 3/2001 | Yanagawa |
| 6,230,707 B1 * | 5/2001 | Horlin ................. A61M 11/002 |
| | | 128/203.15 |
| 6,248,363 B1 | 6/2001 | Patel et al. |
| 6,273,086 B1 | 8/2001 | Ohki et al. |
| 6,290,667 B1 | 9/2001 | Cook et al. |
| 6,298,846 B1 | 10/2001 | Ohki et al. |
| 6,345,737 B1 | 2/2002 | Martin et al. |
| 6,427,680 B1 | 8/2002 | Oechsel et al. |
| 6,488,648 B1 | 12/2002 | Matsugi et al. |
| 6,494,204 B1 | 12/2002 | Ponce et al. |
| 6,516,795 B1 | 2/2003 | Bougamont et al. |
| 6,543,448 B1 | 4/2003 | Smith et al. |
| 6,585,172 B2 | 7/2003 | Arghyris et al. |
| 6,644,305 B2 | 11/2003 | Macrae et al. |
| 6,815,424 B2 | 11/2004 | Vickery et al. |
| 6,824,080 B2 | 11/2004 | Matsugi et al. |
| 6,835,389 B1 | 12/2004 | Dohi et al. |
| 6,855,913 B2 | 2/2005 | Nikodym |
| 6,866,039 B1 | 3/2005 | Wright et al. |
| 6,906,027 B2 | 6/2005 | Oki et al. |
| 6,938,798 B2 | 9/2005 | Stradella et al. |
| 7,022,311 B1 | 4/2006 | Ohkuma et al. |
| 7,115,281 B2 | 10/2006 | Singh et al. |
| 7,278,982 B2 | 10/2007 | Tsutsui |
| 7,306,787 B2 | 12/2007 | Tarara et al. |
| 7,353,823 B2 | 4/2008 | Tsutsui |
| 7,481,218 B2 | 1/2009 | Djupesland et al. |
| 7,638,138 B2 | 12/2009 | Oki et al. |
| 7,806,117 B2 | 10/2010 | Tsutsui |
| 8,062,670 B2 | 11/2011 | Baran, Jr. et al. |
| 8,827,946 B2 | 9/2014 | Tsutsui et al. |
| RE45,404 E | 3/2015 | Tsutsui |
| 10,071,211 B2 | 9/2018 | Tsutsui et al. |
| 2001/0027301 A1 | 10/2001 | Lau et al. |
| 2001/0038824 A1 | 11/2001 | Horii et al. |
| 2002/0002172 A1 | 1/2002 | Bell-Huff et al. |
| 2002/0012688 A1 | 1/2002 | Dohi et al. |
| 2002/0040139 A1 | 4/2002 | Billotte et al. |
| 2002/0062829 A1 | 5/2002 | Ohki et al. |
| 2002/0174865 A1 | 11/2002 | Gatton et al. |
| 2003/0199424 A1 | 10/2003 | Smith et al. |
| 2004/0050966 A1 * | 3/2004 | Piper .................... A61M 11/001 |
| | | 239/340 |
| 2004/0063615 A1 | 4/2004 | Oki et al. |
| 2004/0076588 A1 | 4/2004 | Batycky et al. |
| 2004/0092428 A1 | 5/2004 | Chen et al. |
| 2004/0112378 A1 | 6/2004 | Djupesland et al. |
| 2004/0135002 A1 * | 7/2004 | Beller ................. B05B 11/0038 |
| | | 239/103 |
| 2004/0149289 A1 | 8/2004 | Djupesland et al. |
| 2004/0173211 A1 | 9/2004 | Kladders et al. |
| 2004/0187868 A1 | 9/2004 | Hochrainer et al. |
| 2004/0241232 A1 | 12/2004 | Brown et al. |
| 2005/0022812 A1 | 2/2005 | Hrkach |
| 2005/0042177 A1 | 2/2005 | Ryde et al. |
| 2005/0118272 A1 | 6/2005 | Besse et al. |
| 2005/0142073 A1 | 6/2005 | Watts et al. |
| 2005/0158250 A1 | 7/2005 | Oki et al. |
| 2005/0177095 A1 | 8/2005 | Tsutsui |
| 2005/0232988 A1 | 10/2005 | Venkatesh et al. |
| 2006/0024185 A1 | 2/2006 | Aakerman et al. |
| 2006/0057213 A1 | 3/2006 | Larhrib et al. |
| 2006/0106057 A1 | 5/2006 | Daniel et al. |
| 2006/0116657 A1 | 6/2006 | Schmid |
| 2006/0196556 A1 * | 9/2006 | Johnson ............. F16K 27/0209 |
| | | 137/542 |
| 2006/0216352 A1 | 9/2006 | Nystrom et al. |
| 2006/0217658 A1 | 9/2006 | Tsutsui |
| 2006/0219240 A1 | 10/2006 | Djupesland et al. |
| 2006/0233715 A1 | 10/2006 | Oki et al. |
| 2006/0254585 A1 * | 11/2006 | Ishizeki ............. A61M 15/0043 |
| | | 128/203.15 |
| 2007/0055200 A1 | 3/2007 | Gilbert |
| 2007/0060868 A1 | 3/2007 | Tsutsui |
| 2007/0062525 A1 * | 3/2007 | Bonney ............... A61M 15/009 |
| | | 128/203.15 |
| 2007/0065509 A1 | 3/2007 | Kanikanti et al. |
| 2007/0098804 A1 | 5/2007 | Aronhime et al. |
| 2007/0129665 A1 | 6/2007 | Dickens et al. |
| 2007/0178164 A1 | 8/2007 | Blau |
| 2007/0184109 A1 | 8/2007 | Floyd et al. |
| 2007/0249674 A1 | 10/2007 | Bolton et al. |
| 2007/0272763 A1 | 11/2007 | Dunne et al. |
| 2008/0029084 A1 | 2/2008 | Costantino et al. |
| 2008/0031959 A1 | 2/2008 | Blondino et al. |
| 2008/0090841 A1 | 4/2008 | Johnson et al. |
| 2008/0127972 A1 | 6/2008 | Morton |
| 2008/0142018 A1 | 6/2008 | Doshi et al. |
| 2008/0161771 A1 | 7/2008 | Djupesland et al. |
| 2008/0260848 A1 | 10/2008 | Nagata et al. |
| 2008/0286362 A1 | 11/2008 | Baran, Jr. et al. |
| 2008/0289629 A1 | 11/2008 | Djupesland et al. |
| 2009/0025720 A1 | 1/2009 | Chen et al. |
| 2009/0064997 A1 | 3/2009 | Li et al. |
| 2009/0157037 A1 | 6/2009 | Iyer et al. |
| 2009/0169640 A1 | 7/2009 | Oki et al. |
| 2010/0178331 A1 | 7/2010 | Nagata et al. |
| 2011/0033544 A1 | 2/2011 | Nagata et al. |
| 2011/0045088 A1 * | 2/2011 | Tsutsui .................. A61M 15/08 |
| | | 424/490 |
| 2011/0088690 A1 * | 4/2011 | Djupesland ............ A61M 11/02 |
| | | 128/203.18 |
| 2013/0287852 A1 | 10/2013 | Oki et al. |

FOREIGN PATENT DOCUMENTS

| | | |
|---|---|---|
| CN | 1652836 A | 8/2005 |
| CN | 101217992 A | 7/2008 |
| CN | 101553269 A | 10/2009 |
| CN | 103635218 A | 3/2014 |
| CN | 106470724 A | 3/2017 |
| EP | 0122036 A1 | 10/1984 |
| EP | 0147755 A2 | 7/1985 |

(56) References Cited

FOREIGN PATENT DOCUMENTS

| | | |
|---|---|---|
| EP | 0761248 A1 | 3/1997 |
| EP | 0768094 A2 | 4/1997 |
| EP | 0943326 A1 | 9/1999 |
| EP | 1025859 A1 | 8/2000 |
| EP | 1108423 A1 | 6/2001 |
| EP | 1454648 A1 | 9/2004 |
| EP | 1504780 A1 | 2/2005 |
| EP | 1673123 A2 | 6/2006 |
| EP | 1785145 A1 | 5/2007 |
| EP | 1390091 B1 | 1/2009 |
| EP | 3682922 A1 | 7/2020 |
| GB | 2395900 A | 6/2004 |
| GB | 2448183 A | 10/2008 |
| GB | 2472327 A | 2/2011 |
| JP | 3912469 | 7/1964 |
| JP | S53127553 A | 11/1978 |
| JP | S5420126 A | 2/1979 |
| JP | S5462328 A | 5/1979 |
| JP | S5934267 A | 2/1984 |
| JP | S59163313 A | 9/1984 |
| JP | S60185564 A | 9/1985 |
| JP | S60224616 A | 11/1985 |
| JP | S6242888 B2 | 9/1987 |
| JP | S63267731 A | 11/1988 |
| JP | H0329146 U | 3/1991 |
| JP | H0532560 A | 2/1993 |
| JP | H07165613 A | 6/1995 |
| JP | H0871152 A | 3/1996 |
| JP | H0898888 A | 4/1996 |
| JP | H08103499 A | 4/1996 |
| JP | H08112357 A | 5/1996 |
| JP | H08206208 A | 8/1996 |
| JP | H08243164 A | 9/1996 |
| JP | H08280808 A | 10/1996 |
| JP | H08322934 A | 12/1996 |
| JP | H0928805 A | 2/1997 |
| JP | H0999080 A | 4/1997 |
| JP | H09248342 A | 9/1997 |
| JP | H09276405 A | 10/1997 |
| JP | H09291026 A | 11/1997 |
| JP | H1028735 A | 2/1998 |
| JP | H1059841 A | 3/1998 |
| JP | H11197245 A | 7/1999 |
| JP | H11216357 A | 8/1999 |
| JP | H11221280 A | 8/1999 |
| JP | H11322582 A | 11/1999 |
| JP | 2000229859 A | 8/2000 |
| JP | 2000239187 A | 9/2000 |
| JP | 2001055323 A | 2/2001 |
| JP | 2001095918 A | 4/2001 |
| JP | 2002099080 A | 4/2002 |
| JP | 2002255795 A | 9/2002 |
| JP | 2003154006 A | 5/2003 |
| JP | 2003175103 A | 6/2003 |
| JP | 2003206227 A | 7/2003 |
| JP | 3488624 B2 | 1/2004 |
| JP | 3547605 B2 | 7/2004 |
| JP | 3678955 B2 | 8/2005 |
| JP | 2006122189 A | 5/2006 |
| JP | 2011015954 A | 1/2011 |
| JP | 2014506495 A | 3/2014 |
| JP | 2016140527 A | 8/2016 |
| JP | 2016140530 A | 8/2016 |
| RU | 2013140383 A | 3/2015 |
| WO | WO-9007351 A1 | 7/1990 |
| WO | WO-9404133 A1 | 3/1994 |
| WO | WO-9512399 A1 | 5/1995 |
| WO | WO-9534582 A1 | 12/1995 |
| WO | WO-9624400 A1 * | 8/1996 ........ A61M 15/0028 |
| WO | WO-9731626 A1 | 9/1997 |
| WO | WO-9830207 A1 | 7/1998 |
| WO | WO-9916422 A1 | 4/1999 |
| WO | WO-9916470 A1 | 4/1999 |
| WO | WO-9951205 A1 | 10/1999 |
| WO | WO-0012063 A1 | 3/2000 |
| WO | WO-0012136 A1 | 3/2000 |
| WO | WO-0023023 A1 | 4/2000 |
| WO | WO-0038811 A1 | 7/2000 |
| WO | WO-0126630 A1 | 4/2001 |
| WO | WO-0132125 A2 | 5/2001 |
| WO | WO-0200282 A1 | 1/2002 |
| WO | WO-0232406 A2 | 4/2002 |
| WO | WO-02094233 A1 | 11/2002 |
| WO | WO-03000310 A2 | 1/2003 |
| WO | WO-03004048 A1 | 1/2003 |
| WO | WO-03030872 A2 | 4/2003 |
| WO | WO-03077825 A2 | 9/2003 |
| WO | WO-03095008 A1 | 11/2003 |
| WO | WO-2004004922 A1 | 1/2004 |
| WO | WO-2004073729 A1 | 9/2004 |
| WO | WO-2004087243 A1 | 10/2004 |
| WO | WO-2005000477 A1 | 1/2005 |
| WO | WO-2005013937 A2 | 2/2005 |
| WO | WO-2005056008 A1 | 6/2005 |
| WO | WO-2005104712 A2 | 11/2005 |
| WO | WO-2006016530 A1 | 2/2006 |
| WO | WO-2006040680 A1 | 4/2006 |
| WO | WO-2008026730 A1 | 3/2008 |
| WO | WO-2008031028 A2 | 3/2008 |
| WO | WO-2008075102 A1 | 6/2008 |
| WO | WO-2007102089 A3 | 7/2008 |
| WO | WO-2008078730 A1 | 7/2008 |
| WO | WO-2008031028 A3 | 11/2008 |
| WO | WO-2009095684 A1 | 8/2009 |
| WO | WO-2011013003 A2 | 2/2011 |
| WO | WO-2012105236 A1 | 8/2012 |
| WO | WO-2019065673 A1 | 4/2019 |

OTHER PUBLICATIONS

Extended European Search Report dated May 18, 2021 for EP Application No. 18863196.4.
Advisory action dated Sep. 13, 2013 for U.S. Appl. No. 12/848,850.
Component definition, Dictionary.com, accessed Apr. 1, 2014, pp. 1-4.
European search report and opinion dated Dec. 19, 2011 for Application No. 07860016.0.
European search report and opinion datede Dec. 20, 2013 for Application No. 10774745.3.
European search report dated Jul. 15, 2008 for Application No. 05768543.0.
Final Office action dated Mar. 4, 2013 for U.S. Appl. No. 12/848,850.
Final Office action dated Apr. 2, 2015 for U.S. Appl. No. 13/649,515.
"Fluorouracil" definition viewed on the National Cancer Institute website at www.cancergov/drugdictionary?cdrid=43130 on May 31, 2012.
Hens, et al., "BMP4 and PTHrP interact to stimulate ductal outgrowth during embryonic mammary development and to inhibit hair follicle induction," Development 2007, 134, pp. 1221-1230.
Hibberd, et al. Immunization strategies for the immunocompromised host: the need for immunoadjuvants. Ann Intern Med. Jun. 15, 1989;110(12):955-6.
International search report dated Jun. 8, 2010 for PCT Application No. JP2010/003285.
International search report and written opinion dated Jun. 28, 2011 for PCT Application No. IB2010/02168.
International search report dated Nov. 1, 2005 for PCT Application No. JP2005/014389.
International search report dated Feb. 5, 2008 for PCT Application No. JP2007/074787.
International search report dated May 7, 2003 for PCT Application No. JP2003/001948.
International search report (partial) dated Dec. 21, 2010 for PCT Application No. IB2010/02168.
Ishikawa, et al. Improved nasal bioavailability of calcitonin by insoluble powder formulation. Int J Pharm. Aug. 14, 2001;224(1-2):105-14.
Kleinebudde, et al. Influence of degree of polymerization on behavior of cellulose during homogenization and extrusion/spheronization. AAPS Pharmasci 2000, 2(2) Article 21, 1-10.

(56) References Cited

OTHER PUBLICATIONS

Labiris, et al. Pulmonary drug delivery. Part I: physiological factors affecting therapeutic effectiveness of aerosolized medications. Br J Clin Pharmacol. Dec. 2003;56(6):588-99.
Merriam-Webster's Collegiate Dictionary, 10th edition, Merriam-Webster Incorporated: Springfield, Massachusetts, 1993, pp. 41.
Notice of allowance dated Apr. 22, 2015 for U.S. Appl. No. 12/780,433.
Notice of allowance dated Sep. 24, 2014 for U.S. Appl. No. 12/576,219.
Notice of allowance dated Nov. 5, 2014 for U.S. Appl. No. 13/827,859.
Office Action and translation issued in Chinese Patent Application No. 2018800763432 dated Aug. 26, 2021.
Office action dated Jan. 6, 2014 for U.S. Appl. No. 12/576,219.
Office action dated Jan. 13, 2011 for U.S. Appl. No. 12/346,537.
Office action dated Jan. 20, 2011 for U.S. Appl. No. 12/576,219.
Office action dated Jan. 29, 2008 for U.S. Appl. No. 10/545,764.
Office action dated Apr. 8, 2014 for U.S. Appl. No. 13/827,859.
Office action dated Apr. 9, 2014 for U.S. Appl. No. 12/780,433.
Office action dated Apr. 12, 2012 for U.S. Appl. No. 12/576,219.
Office action dated Apr. 20, 2012 for U.S. Appl. No. 12/780,433.
Office action dated May 7, 2013 for U.S. Appl. No. 11/660,131.
Office action dated Jun. 4, 2012 for U.S. Appl. No. 12/521,116.
Office action dated Jun. 10, 2013 for U.S. Appl. No. 12/576,219.
Office action dated Jun. 25, 2012 for U.S. Appl. No. 12/346,537.
Office action dated Sep. 6, 2011 for U.S. Appl. No. 12/346,537.
Office action dated Sep. 6, 2011 for U.S. Appl. No. 12/576,219.
Office action dated Sep. 20, 2013 for U.S. Appl. No. 13/827,859.
Office action dated Sep. 24, 2008 for U.S. Appl. No. 10/545,764.
Office action dated Sep. 27, 2010 for U.S. Appl. No. 11/660,131.
Office action dated Sep. 28, 2011 for JP Application No. 2006-531575 (in Japanese with English translation).
Office action dated Oct. 10, 2012 for U.S. Appl. No. 12/780,433.
Office action dated Oct. 15, 2012 for U.S. Appl. No. 12/848,850.
Office action dated Oct. 15, 2014 for U.S. Appl. No. 12/780,433.
Office action dated Oct. 29, 2009 for U.S. Appl. No. 11/660,131.
Office action dated Nov. 1, 2012 for U.S. Appl. No. 11/660,131.
Office action dated Nov. 24, 2014 for U.S. Appl. No. 13/649,515.
Office action dated Dec. 5, 2011 for U.S. Appl. No. 12/346,537.
Partition Coefficient, Wikipedia, accessed Mar. 31, 2014, pp. 1-8.
Rowe, et al. (Eds). Handbook of Pharmaceutical Excipients. Pharmaceutical Press. 2003. p. 108-109.
Topliss, John. Quantitative Structure-Activity Relationships of Drugs, 1983, pp. 2.
UK combined office action and search report dated Nov. 10, 2010 for Application No. GB1012959.1.
UK office action dated Apr. 10, 2012 for Application No. GB1012959.1.
UK search report dated Sep. 9, 2011 for Application No. GB1012959.1.
U.S. Appl. No. 12/576,219, filed Oct. 8, 2009.
U.S. Appl. No. 13/649,515, filed Oct. 11, 2012.
First Examination Report issued in Indian Patent Application No. 202017014124 dated Mar. 20, 2022.

* cited by examiner

INTRANASAL DELIVERY DEVICES

CROSS-REFERENCE

This application claims the benefit of U.S. Provisional Application No. 62/563,244 filed on Sep. 26, 2017, which is incorporated herein by reference in its entirety.

INCORPORATION BY REFERENCE

All publications and patent applications mentioned in this specification are herein incorporated by reference to the same extent as if each individual publication or patent application was specifically and individually indicated to be incorporated by reference.

BRIEF SUMMARY

In some cases, the present disclosure provides a device that comprises: a nozzle having a reservoir disposed within the nozzle, a poppet valve at least partially fit into the reservoir, a retainer that is hollow and holds the poppet valve, and a manual air pump, e.g., operably linked to an upstream end of the nozzle and a downstream end of the retainer, wherein the poppet valve has one or more contacting points with the retainer. In some instances, the one or more contacting points are one or more inner ribs. In some instances, the retainer has an inner circumferential groove based from an upstream end of the retainer. In some instances, a rim of the circumferential groove of the retainer is in contact with the one or more contacting points of the poppet valve. In some instances, the retainer immobilizes the poppet valve. In some instances, when the device is activated, a portion of air from the pump flows into the retainer along the circumferential groove and travels through surface grooves of the retainer to generate a vortex into the reservoir. In some instances, the one or more air intake holes of the retainer allows outside air to enter the pump after the device is activated. In some instances, the reservoir contains a powdered therapeutic formulation. In some instances, the device is adapted to deliver at least about 85% of the powdered therapeutic formulation into a nostril of a subject after a single, two, or three times of activation of the manual air pump. In some instances, at least about 90% of the powdered therapeutic formulation is delivered into the nostril of the subject after the single, two, or three times of activation of the manual air pump. In some instances, the powdered therapeutic formulation is present in an amount of about 1 to about 30 mg. In some instances, the powdered therapeutic formulation is present in an amount of about 20 mg. In some instances, the nozzle further comprises a breakable tab positioned at the downstream end of the nozzle. In some instances, the device is a single-use device. In some instances, the poppet valve further comprises a conical top section. In some instances, the conical top section is connected to a first shelf that is connected to a first cylindrical section. In some instances, the first cylindrical section is connected to a second shelf that is connected to a second cylindrical section. In some instances, the poppet valve has one or more surface grooves. In some instances, the poppet valve has about 3 to about 20 surface grooves, for example about 8 surface grooves. In some instances, the one or more surface grooves creates a vortex in the reservoir when the device is activated. In some instances, the one or more surface grooves are present on the second shelf. In some instances, the poppet valve has about 2 to about 10 inner ribs. In some instances, the poppet valve has about 3 inner ribs. In some instances, the poppet valve is at least partially located within the reservoir. In some instances, the poppet valve is at least partially located within the manual air pump. In some instances, the poppet valve comprises a cavity. In some instances, the device is less than about 100 $cm^3$ in volume. In some instances, the device is less than about 50 $cm^3$ in volume. In some instances, the device is about 30 $cm^3$ in volume. In some instances, the device has a mass of less than about 20 grams. In some instances, the device has a mass less than about 10 grams. In some instances, the device has a mass of about 6-7 grams. In some instances, the reservoir has an inner diameter of less than about 10 mm. In some instances, the reservoir has an outer diameter of about 8 to about 9 mm. In some instances, the outer diameter of the reservoir is about 8.7 to about 8.9 mm. In some instances, an upstream end of the reservoir has smooth surface adapted to contact the poppet valve. In some instances, the poppet valve has an outer diameter of about 7 to about 8 mm, for example about 7.7 to about 7.9 mm. In some instances, an opening of the manual air pump is wider than an outer diameter of the poppet valve. In some instances, the retainer contains an outer circumferential rim that is wider than an opening of the manual air pump. In some instances, the retainer has two air intake holes. In some instances, the one or more air intake holes are about 0.2-0.4 mm wide. In some instances, the retainer is at least partially fit into the manual air pump. In some instances, a portion of the poppet valve fit into the nozzle is about 5 mm to about 6 mm, for example 5.7 mm to about 5.9 mm, in length parallel to an upstream to downstream axis. In some instances, the nozzle has a length parallel to an upstream to downstream axis of between 5 mm and 40 mm. In some instances, the nozzle of the device comprises a clear, lightly tint, or translucent material.

In some cases, the present disclosure provides a method of using a device disclosed herein to deliver a powdered therapeutic formulation in a subject in need thereof, comprising positioning a nozzle of the device at least partially into a nostril of the subject and activating the manual air pump, wherein the nozzle comprises the powdered therapeutic formulation. In some instances, the method treats a disease or condition of the subject, for example migraine. In some instances, the powdered therapeutic formulation comprises an active agent disclosed herein, for example dihydroergotamine or a pharmaceutically acceptable salt thereof. In some instances, the method further comprises visually inspecting the amount of the powdered therapeutic formulation remaining in the reservoir and repeating the method until a sufficient dose is delivered.

In some cases, the present disclosure provides a method of manufacturing the device, comprising: inserting the poppet valve in the nozzle, inserting the retainer in the manual air pump, and coupling the manual air pump to the nozzle. In some instances, the method further comprises filling the reservoir with a powdered therapeutic formulation.

DETAILED DESCRIPTION

Figure 1:
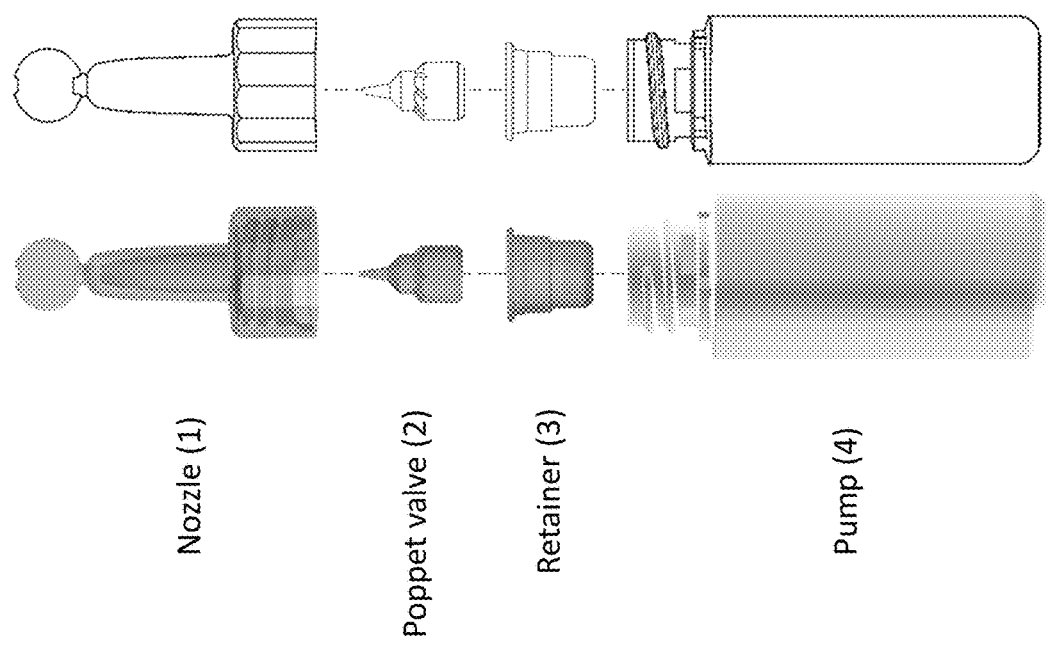
FIG. 1 illustrates two views of parts of a device. The device comprises a nozzle (1), a poppet valve (2), a retainer (3), and a pump (4). The device can further comprise a cap to protect the nozzle.

The present application describes intranasal delivery devices. An intranasal delivery device can be used for administering a powdered therapeutic formulation to a person in need of treatment. Delivery of a powdered therapeutic formulation can be performed by a medical professional and/or by a subject in need of treatment (e.g., a human subject). As described herein, devices can be pre-loaded with a dry powdered therapeutic formulation. An intranasal delivery device can be a single-use device. A device described herein can comprise at least four parts, e.g., a nozzle, a retainer, a poppet valve, and a pump. A powdered therapeutic formulation can be introduced into the nozzle of a device, which can serve as a reservoir. The nozzle can be coupled with a pump. Devices described herein can provide for complete delivery of a powdered therapeutic formulation with minimal powdered therapeutic formulation remaining in the device after activation of the device. A poppet valve can be adapted to regulate airflow from a pump to a nozzle when the device is activated. A poppet valve can be adapted to prevent movement of a powdered therapeutic formulation from a reservoir in the device upstream to a pump in the device. The poppet valve can comprise slits (canals or grooves) that can be used to generate a vortex in a reservoir to enable efficient delivery of a powdered therapeutic formulation. The grooves in the poppet valve can be positioned to permit laminar air flow in the reservoir. The grooves in the poppet valve can be positioned to create spinning air flow in the reservoir when the pump is activated. Also provided are methods for treating or prevention a condition or disease with a device or a formulation disclosed herein.

Unless defined otherwise, all technical and scientific terms used herein have the same meaning as commonly understood by one of the ordinary skill in the art to which this invention belongs. Although any methods and materials similar or equivalent to those described herein can be used in the practice or testing of the compositions or unit doses herein, some methods and materials are now described. Unless mentioned otherwise, the techniques employed or contemplated herein are standard methodologies. The materials, methods and examples are illustrative only and not limiting.

The details of one or more inventive embodiments are set forth in the accompanying drawings, the claims, and the description herein. A feature, object, or advantage of an inventive embodiment disclosed and contemplated herein can be combined with that of any other embodiment disclosed and contemplated herein, unless explicitly excluded.

Unless otherwise indicated, open terms for example "contain," "containing," "include," "including," and the like mean comprising.

The singular forms "a", "an", and "the" are used herein to include plural references unless the context clearly dictates otherwise. Accordingly, unless the contrary is indicated, the numerical parameters set forth in this application are approximations that may vary depending upon the desired properties sought to be obtained by the present invention.

Unless otherwise indicated, some instances herein contemplate numerical ranges. When a numerical range is provided, unless otherwise indicated, the range includes the range endpoints. Unless otherwise indicated, numerical ranges include all values and subranges therein as if explicitly written out. Unless otherwise indicated, any numerical ranges and/or values herein can be at 80-125% of the numerical ranges and/or values.

The term "about" means the referenced numeric indication plus or minus 15% of that referenced numeric indication.

The term "subject" as used herein refers to a mammal (e.g., a human, mouse, rat, guinea pig, dog, cat, horse, cow, pig, or non-human primate, such as a monkey, chimpanzee or baboon). In a particular instance, the subject is a human subject.

I. Devices

Overview

In some cases, the present disclosure provides a device that comprises: a nozzle having a reservoir disposed within the nozzle, a poppet valve at least partially fit into the reservoir, a retainer that is hollow and holds the poppet valve, and a manual air pump operably linked to an upstream end of the nozzle and a downstream end of the retainer, wherein the poppet valve has one or more contacting points with the retainer. In some instances, the one or more contacting points are one or more inner ribs. In some instances, the retainer has an inner circumferential groove based from an upstream end of the retainer. In some instances, a rim of the circumferential groove of the retainer is in contact with the one or more contacting points of the poppet valve. In some instances, the retainer immobilizes the poppet valve. In some instances, when the device is activated, a portion of air from the pump flows into the retainer along the circumferential groove and travels through surface grooves of the retainer to generate a vortex into the reservoir. In some instances, the one or more air intake holes of the retainer allows outside air to enter the pump after the device is activated. In some instances, the reservoir contains a powdered therapeutic formulation. In some instances, the device is adapted to deliver at least about: 70%, 75%, 80%, 85%, 90%, or 95% of the powdered therapeutic formulation into a nostril of a subject after a single, two, or three times of activation of the manual air pump. In some instances, the powdered therapeutic formulation is present in an amount of about 1 to about 30 mg, or about 1 to about 50 mg. In some instances, the powdered therapeutic formulation is present in an amount of about: 5, 10, 15, 20, 25, 30, 35, 40, or 45 mg. In some instances, the nozzle further comprises a breakable tab positioned at the downstream end of the nozzle. In some instances, the device further comprises a cap that at least partially covers the nozzle. In some instances, the cap comprises polypropylene. In some instances, the nozzle further comprises an engaging screw adaptable to secure the nozzle to the manual air pump. In some instances, the manual air pump further comprises an engaging thread adaptable to secure the manual air pump to the nozzle. In some instances, the engaging thread spans a width of about 9-12 mm, for example about: 9.7-10.3 mm, 10.1-10.7 mm, or 10.5-11.1 mm. In some instances, the device is a single-use device. In some instances, the poppet valve further comprises a conical top section. In some instances, the conical top section is connected to a first shelf that is connected to a first cylindrical section. In some instances, the first cylindrical section is connected to a second shelf that is connected to a second cylindrical section. In some instances, the poppet valve has one or more surface grooves. In some instances, the poppet valve has about 3 to about 20 surface grooves, for example about: 4, 6, 8, 10, 12, 14, 16, or 18 surface grooves. In some instances, the one or more surface grooves creates a vortex in the reservoir when the device is activated. In some instances, the one or more surface grooves are present on the second shelf. In some instances, the poppet valve has about 2 to about 10 inner ribs. In some instances, the poppet valve has about: 3 inner ribs. In some instances, the poppet valve is at least partially located within the reservoir. In some instances, the poppet valve is at least partially located within the manual air pump. In some instances, the poppet valve comprises a cavity. In some instances, the device is less than about 100 cm$^3$ in volume. In some instances, the device is less than about 50 cm$^3$ in volume. In some instances, the device is about: 20 cm$^3$ or 30 cm$^3$ in volume. In some instances, the device has a mass of less than about 20 grams, for example about: 11, 12, 13, 14, 15, 16, 17, 18, or 19 grams. In some instances, the device has a mass less than about 10 grams, for example about: 1, 2, 3, 4, 5, 6, 7, 8, or 9 grams. In some instances, the device has a mass of about 6-7 grams. In some instances, the reservoir has an inner diameter of less than about 10 mm. In some instances, the reservoir has an outer diameter of about 8 to about 9 mm. In some instances, the outer diameter of the reservoir is about 8.7 to about 8.9 mm. In some instances, an upstream end of the reservoir has smooth surface adapted to contact the poppet valve. In some instances, the poppet valve has an outer diameter of about 7 to about 8 mm, for example about 7.7 to about 7.9 mm. In some instances, an opening of the manual air pump is wider than an outer diameter of the poppet valve. In some instances, the retainer contains an outer circumferential rim that is wider than an opening of the manual air pump. In some instances, the retainer has two air intake holes. In some instances, the one or more air intake holes are about 0.2-0.4 mm wide. In some instances, the retainer is at least partially fit into the manual air pump. In some instances, a portion of the poppet valve fit into the nozzle is about 5 mm to about 6 mm, for example about 5.7 mm to about 5.9 mm, in length parallel to an upstream to downstream axis. In some instances, the nozzle has a length parallel to an upstream to downstream axis of from about 5 mm to about 40 mm. In some instances, the nozzle of the device comprises a clear, lightly tint, or translucent material.

In some cases, the present disclosure provides a method of using a device disclosed herein to deliver a powdered therapeutic formulation in a subject in need thereof, comprising positioning a nozzle of the device at least partially into a nostril of the subject and activating the manual air pump, wherein the nozzle comprises the powdered therapeutic formulation. In some instances, the method treats a disease or condition of the subject, for example migraine. In some instances, the powdered therapeutic formulation comprises an active agent disclosed herein, for example dihydroergotamine or a pharmaceutically acceptable salt thereof. In some instances, the method further comprises visually inspecting the amount of the powdered therapeutic formulation remaining in the reservoir and repeating the method until a sufficient dose is delivered.

In some cases, the present disclosure provides a method of manufacturing the device, comprising: inserting the poppet valve in the nozzle, inserting the retainer in the manual air pump, and coupling the manual air pump to the nozzle. In some instances, the method further comprises filling the reservoir with a powdered therapeutic formulation.

In some cases, a device is provided comprising: a) a nozzle having an upstream end and a downstream end adapted to allow positioning of at least a portion of said nozzle into a nostril of a subject; b) a reservoir comprising a single dose of a powdered therapeutic formulation, the reservoir having an upstream end and a downstream end, and disposed within said nozzle; c) a poppet valve having an upstream end and a downstream end, wherein the poppet valve is adapted to cause diffusion of the powdered therapeutic formulation when the device is activated; and d) a pump operably linked to the upstream end of a poppet valve, wherein the device is a single-use device. In some instances, the poppet valve is adapted to create a spinning airflow in the reservoir when the pump is activated. In some instances, the poppet valve is adapted to permit the entire wall of the reservoir to be covered by airflow when the pump is activated. In some instances, the poppet valve is at least partially located in the nozzle. In some instances, the powdered therapeutic formulation is located along the internal wall of the nozzle and between the poppet valve and internal wall of the nozzle. In some instances, the poppet valve is adapted to minimize the powdered therapeutic formulation remaining between the poppet valve and the internal wall of the nozzle when the pump is activated. In some instances, the device is adapted to deliver from about 80% to about 99% of the single dose of powdered therapeutic formulation into the nostril of the subject. In some instances, the device is adapted to deliver about 80% to about 99% of the single dose of powdered therapeutic formulation into the nostril of the subject after a single activation of the pump. In some instances, the pump comprises a flow outlet. In some instances, the poppet valve is adapted to prevent movement of the powdered therapeutic formulation through the flow outlet when the device is not activated. In some instances, the poppet valve is adapted to prevent movement of the powdered therapeutic formulation through the flow outlet when the device is activated. In some instances, the poppet valve covers the flow outlet when the device is not activated. In some instances, the poppet valve does not cover the flow outlet when the device is activated. In some instances, the poppet valve comprises a top section connected to a first cylindrical section, and the first cylindrical section is connected to a first shelf, and the first shelf is connected to a second cylindrical section.

In some instances, the top section comprises a conical shape. In some instances, a surface of the first shelf comprises at least one groove. In some instances, the first shelf comprises at least one groove. In some instances, the first shelf comprises about 1 to 50 grooves. In some instances, the first shelf comprises about 1 to 20 grooves. In some instances, the first shelf comprises about 1 to 10 grooves. In some instances, the at least one groove lies at a 45 degree angle relative to an edge of the first shelf. In some instances, the at least one groove is adapted to permit air flow from the pump to the nozzle when the pump is engaged. In some instances, the nozzle comprises a nozzle pipe. In some instances, the poppet valve is partially located within the nozzle pipe. In some instances, the top section and first cylindrical section of the poppet valve are located within the nozzle pipe. In some instances, the second cylindrical section of the poppet valve is not located within the nozzle pipe.

In some instances, the first shelf contacts the nozzle pipe in the pump is activated. In some instances, the pump is adapted to deliver about 2 to 7 mL of air. In some instances, the device is adapted to deliver about 1 to 50 mg of powdered therapeutic agent. In some instances, the device is less than about 50 cm³ in volume. In some instances, the device has a mass of less than about 20 grams. In some instances, the pump is adapted to be activated by a user to force air from the pump through the flow outlet, along the surface of the at least one groove in the first shelf, into the reservoir, and out the downstream end of a nozzle. In some instances, the device is adapted to provide laminar airflow within at least a portion of a reservoir while a device is in use. In some instances, the device is adapted to deliver a powdered therapeutic formulation into the nostril of the subject by application of from about 5 to about 30 kilopascals of compressive force to a pump. In some instances, the pump further comprises a deformable volume adapted to be activated by a user. In some instances, the pump comprises a manual air pump. In some instances, the manual air pump is adapted to be activated by a user by squeezing the pump between a thumb and a forefinger, middle finger, ring finger, little finger or combination thereof. In some instances, the reservoir comprises an inner diameter of less than about 10 mm. In some instances, the nozzle further comprises a length perpendicular to an upstream to downstream axis of about 5 mm to about 20 mm. In some instances, the nozzle further comprises a length parallel to an upstream to downstream axis of about 5 mm to about 40 mm.

In some instances, the pump further comprises a flow inlet, wherein said flow inlet is less than 10% of the size of a flow outlet. In some instances, said flow inlet is about 0.1 to 2 mm in diameter. In some instances, the nozzle further comprises an airtight cap positioned on the upstream end of a nozzle and adapted to prevent outside air from contacting a powdered therapeutic formulation. In some instances, the nozzle further comprises a removable or breakable tab positioned at the downstream end of the nozzle, and adapted to prevent a flow of air through a nozzle. In some instances, the downstream end of the nozzle further comprises a nozzle hole.

In some instances, the poppet valve is adapted to provide laminar airflow along at least a portion of the reservoir. In some instances, sufficient flow of air is generated by a compression force of at least 20 kilopascals applied to the pump. In some instances, the nozzle is comprised of a substantially clear or translucent material. In some instances, the nozzle further comprises a thread adaptable to secure the nozzle to the pump.

In some cases, a method of using a device to deliver a powdered therapeutic formulation is provided, wherein said method comprises positioning a nozzle of a device into a nostril of a subject and activating a pump, and wherein said device is a single-use device that comprises: a) a nozzle having an upstream end and a downstream end, said nozzle adapted to allow position of at least a portion of said nozzle into a nostril of a subject; b) a reservoir comprising a dose of a powdered therapeutic formulation and having an upstream end and a downstream end, operably linked to and disposed within said nozzle; c) a poppet valve having an upstream end and a downstream end, wherein the poppet valve is adapted to cause diffusion of the powdered therapeutic formulation when the device is activated; d) a retainer having inner ribs linked to the poppet valve; and e) a pump operably linked to the upstream end of the retainer. In some instances, the device is a single-use device. In some instances, the nozzle and the reservoir of the device comprise clear or translucent material. In some instances, the method further comprises visually inspecting the amount of powdered therapeutic formulation remaining in a reservoir and repeating the method until a sufficient dose is delivered. In some instances, the method further comprises activating the pump to produce laminar flow along at least a portion of a reservoir. In some instances, the method further comprises delivering between 1 mg and 50 mg of a powdered therapeutic formulation to the nostril of the subject. In some instances, the method further comprises delivering about 80%-99% of the single dose of powdered therapeutic formulation to the nostril of the subject. In some instances, the method further comprises compressing the manual air pump with about 5-30 kilopascals of force. In some instances, the method further comprises removing a cover from the nozzle before the nozzle is positioned in the nostril of the subject.

In some cases, a method of manufacturing a device for delivering a powdered therapeutic formulation to a subject, wherein said method comprises providing a powdered therapeutic formulation to a reservoir and subsequently coupling a nozzle to a pump, wherein said device comprises: a) a nozzle having an upstream end and a downstream end, said nozzle adapted to allow positioning of at least a portion of said nozzle into a nostril of a subject; b) a reservoir comprising a dose of a powdered therapeutic formulation and having an upstream end and a downstream end, operably linked to and disposed within said nozzle; c) a poppet valve having an upstream end and a downstream end, wherein the poppet valve is adapted to cause diffusion of the powdered therapeutic formulation when the device is activated; d) a retainer having inner ribs linked to the poppet valve; and e) a pump operably linked to the upstream end of the retainer.

In some instances, the device does not comprise a flow inlet when the removable cover positioned at the downstream end of the nozzle is not removed. In some instances, the reservoir for a powdered therapeutic formulation is a closed system when the removable cover is not removed, thereby increasing the stability of a powdered therapeutic formulation within the reservoir. In some instances, the device comprises a flow inlet when the removable cover positioned at the downstream end of the nozzle is removed. In some instances, the downstream end of the nozzle further comprises a nozzle hole and the nozzle hole comprises the flow inlet.

In some instances, the poppet valve comprises an inner inlet section and the inner inlet section is connected to a first cylindrical section, and the first cylindrical section is connected to a first shelf, and the first shelf is connected to a second cylindrical section. In some instances the poppet valve further comprises an inner inlet section and the inner inlet section is connected to the top section. In some instances, the poppet valve comprises a poppet valve cavity. In some instances, the poppet valve cavity comprises a hollow chamber within the poppet valve, an opening at the upstream end of the poppet valve cavity, and an opening at the downstream end of the poppet valve cavity. In some instances, the poppet valve cavity spans the entire length of the poppet valve. In some instances, the poppet valve cavity and the opening at the upstream end of the poppet valve cavity is connected to the reservoir and the opening at the downstream end of the poppet valve cavity is connected to the pump.

Device Height

The devices disclosed herein can be of any convenient dimensions for application of a powdered therapeutic formulation contained therein. For example, a device can be about: 3-15 cm, 4-15 cm, 5-15 cm, 6-15 cm, 7-15 cm, 8-15 cm, 3-10 cm, 3-9 cm, or 3-8 cm in height. A device can be about 3 cm, about 4 cm, about 5 cm, about 6 cm, about 7 cm, about 8 cm, about 9 cm, about 10 cm, about 11 cm, about 12 cm, about 13 cm, about 14 cm, or about 15 cm in height. A device can be more than: about 3 cm, about 4 cm, about 5 cm, about 6 cm, about 7 cm, about 8 cm, about 9 cm, about 10 cm, about 11 cm, about 12 cm, about 13 cm, about 14 cm, or about 15 cm in height. A device can be less than: about 3 cm, about 4 cm, about 5 cm, about 6 cm, about 7 cm, about 8 cm, about 9 cm, about 10 cm, about 11 cm, about 12 cm, about 13 cm, about 14 cm, or about 15 cm in height. Dimensions for the device can be chosen based on the amount of powdered therapeutic formulation to be delivered, ease of use, ease of portability, or manufacturing convenience.

Device Volume

As described herein, a device can be configured to be a small size such that it can easily be stored or transported. A device can be between about 1 and 100 $cm^3$ in volume, between about 5 and 90 $cm^3$ in volume, between about 10 and 80 $cm^3$ in volume, between about 25 and 80 $cm^3$ in volume, between about 50 and 100 $cm^3$ in volume, between about 1 and 50 $cm^3$ in volume, between about 5 and 75 $cm^3$ in volume, between about 1 and 25 $cm^3$ in volume, between about 5 and 50 $cm^3$ in volume, between about 10 and 50 $cm^3$ in volume, or between about 25 and 50 $cm^3$ in volume. A device can be at least about: 1, 2, 5, 10, 25, 30, 40, 50, 75, or 100 $cm^3$ in volume. A device can be less than about: 250, 200, 175, 150, 125, 100, 75, 70, 65, 60, 55, 50, 40, 30, 25, 10, 5, 2, or 1 $cm^3$ in volume.

Device Width

At its widest point, the device can be between about 0.5-5 cm in width. The device at its widest point can be about: 0.5, 1, 1.5, 2, 2.5, 3, 3.5, 4, 4.5, or 5 cm in width. The device at its widest point can be more than about: 0.5, 1, 1.5, 2, 2.5, 3, 3.5, 4, 4.5, or 5 cm in width. The device at its widest point can be less than about: 0.5, 1, 1.5, 2, 2.5, 3, 3.5, 4, 4.5, or 5 cm in width.

Device Mass

A device can be configured to be lightweight. For example, a device can have a total mass of between about 1 and about 50 grams, between about 5 and about 40 grams, between about 10 and about 35 grams, between about 10 and about 30 grams, between about 10 and about 25 grams, between about 1 and about 10 grams, between about 1 about 5 grams, or between about 10 and about 20 grams. A device can have a total mass of less than about: 100 grams, 90 grams, 80 grams, 75 grams, 70 grams, 65 grams, 60 grams, 55 grams, 50 grams, 45 grams, 40 grams, 35 grams, 30 grams, 25 grams, 20 grams, 10 grams, 9 grams, 8 grams, 7 grams, 6 gram, 5 grams, 4 grams, 3 grams, 2 grams, 1 gram, 0.5 gram, or less. A device can have a total mass of more than about: 0.5 gram, 1 gram, 2 grams, 3 grams, 4 grams, 5 grams, 6 grams, 7 grams, 8 grams, 9 grams, 10 grams, 11 grams, 12, grams, 13 grams, 14 grams, 15 grams, 16 grams, 17 grams, 18 grams, 19 grams, 20 grams, 25 grams, 30 grams, 35 grams, 40 grams, 45 grams, 50 grams, 55 grams, 60 grams, 65 grams, 70 grams, 75 grams, 80 grams, 85 grams, 90 grams, 95 grams, or 100 grams. A device can a have a total mass of about: 1 gram, 2 grams, 3 grams, 4 grams, 5 grams, 6 grams, 7 grams, 8 grams, 9 grams, 10 grams, 11 grams, 12, grams, 13 grams, 14 grams, 15 grams, 16 grams, 17 grams, 18 grams, 19 grams, 20 grams, 25 grams, 30 grams, 35 grams, 40 grams, 45 grams, 50 grams, 55 grams, 60 grams, 65 grams, 70 grams, 75 grams, 80 grams, 85 grams, 90 grams, 95 grams, or 100 grams. Total mass can be the mass of a device without a powdered therapeutic formulation or the mass of a device with a powdered therapeutic formulation.

Device Delivery Efficiency

As described herein, a device can be configured to deliver a substantial fraction of a single dose of a powdered therapeutic formulation (powdered formulation) into a nostril of a subject. A device can be configured to deliver a substantial fraction of an amount of powdered therapeutic formulation residing within the device into a nostril of a subject. A powdered therapeutic formulation or a substantial fraction thereof can be delivered after a single activation of a device. Activation of a device can be, for example, compression of a flexible vial that serves as a manual air pump. A substantial fraction of a powdered therapeutic formulation can be delivered after multiple activations of a device, such as, for example 2, 3, 4, 5, 6, 7, 8, 9, or 10 activations. Multiple activations of a device can constitute a single use of a device. The substantial fraction of powdered therapeutic formulation that can be delivered by a device can be at least about: 50%, 55%, 60%, 65%, 70%, 75%, 80%, 85%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5%, 99%, 99.1%, 99.2%, 99.3%, 99.4%, 99.5%, 99.5%, 99.6%, 99.7%, 99.8% 99.9%, 99.95%, or 100% of the amount of powdered therapeutic formulation such as the amount in a single dose or the amount residing in the device. The substantial fraction of powdered therapeutic formulation that can be delivered by a device can be about: 50%, 55%, 60%, 65%, 70%, 75%, 80%, 85%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5%, 99%, 99.1%, 99.2%, 99.3%, 99.4%, 99.5%, 99.5%, 99.6%, 99.7%, 99.8% 99.9%, 99.95%, or 100% of the amount of powdered therapeutic formulation such as the amount in a single dose or the amount residing in the device. In some instances, about: 60-100%, 60-99%, 60-95%, 60-90%, 60-85%, 60-80%, 60-75%, 60-70%, 70-100%, 70-99%, 70-95%, 70-90%, 70-85%, 70-80%, 75-100%, 75-99%, 75-95%, 75-90%, 75-85%, 75-80%, 80-100%, 80-99%, 80-95%, 80-90%, 80-85%, 85-100%, 85-99%, 85-95%, 85-90%, 90-100%, 90-99%, 90-95%, 95-100%, or 95-99% of the amount of powdered therapeutic formulation is expelled from the device after the first activation. In such instances, a second activation can result in expulsion of substantially all of the powdered therapeutic formulation. The remainder of 1% or less of the powdered therapeutic formulation in the device, typically as a residual powder on the walls of the chamber, can constitute delivery of substantially all of the powdered therapeutic formulation.

A. Nozzle

Provided herein are nozzles adapted to deliver a powdered therapeutic formulation to a nostril of a subject. In some instances, a nozzle is adapted to be placed partially or completely into a nostril of a subject during use. In some instances, a nozzle is adapted to be placed externally and adjacent to a nostril, totally or partially covering the opening of a nostril.

Nozzle Shape

A nozzle disclosed herein is not limited to a particular shape. A nozzle can be of a uniform width such as in the shape of a cylinder, a cuboid, a rhombohedron, or a parallelepiped. A nozzle can also be a funnel or frustum shape, with a wide end and a narrow end. The shape of a nozzle can be wider at the upstream end and narrower at the downstream end. A nozzle can be wider at the downstream end and narrower at the upstream end. In some instances, the widest and narrowest sections of a nozzle, however, are not being at any end. For example, the widest section of a nozzle can be at any position along the upstream to downstream axis. In nozzles where the widest section is found mid-length along the axis, the widest section can function as a stop that prevents the nozzle from being inserted further into a nostril. In some instances, a nozzle is composed of two or more shapes such as any of the shapes provided herein. For example, a nozzle can include a cylinder shaped portion and a cone shaped portion. The nozzle can include a section, e.g., a nozzle pipe, designed for insertion into a nostril and a section, e.g., a nozzle base, designed for attachment to a pump, for example, attachment to the throat of a flexible vial.

Nozzle Material

A nozzle can be composed of a variety of polymers, plastics, rubber, silicones, metal, composites, any other materials described herein as suitable for use in the manufacture of a device applicator, or any other material suitable for use as an applicator nozzle. A nozzle can be made of one material or type of material. A nozzle can be composed two or more different materials or types of materials. All or a portion of a nozzle can be a biocompatible material or a hypoallergenic material. In some instances, a nozzle is comprised of one or more of cyclic olefin copolymer (COC), silicone, styrene butadiene block copolymer (SBC), polyacetal, polyoxymethylene, acrylates, polyethylenes, polyurethane, hydrogel, polyester (e.g., DACRONB from E. I. Du Pont de Nemours and Company, Wilmington, Del.), polypropylene, polytetrafluoroethylene (PTFE), expanded PTFE (ePTFE), polyether ether ketone (PEEK), nylon, extruded collagen, polymer foam, rubber, silicone rubber, polyethylene terephthalate, ultra high molecular weight polyethylene, polycarbonate urethane, polyimides, aluminum, stainless steel, nickel-titanium alloy (e.g., Nitinol), titanium, stainless steel, or cobalt-chrome alloy (e.g., ELGILOYB from Elgin Specialty Metals, Elgin, Ill.; CONICHROMEB from Carpenter Metals Corp., Wyomissing, Pa.).

Nozzle Opaqueness

A nozzle can be composed partially or entirely of clear or translucent materials. The use of a clear or translucent nozzle can allow for the visual inspection of the nozzle to ascertain whether there is appreciable residual powdered therapeutic formulation (powdered formulation) remaining in a reservoir after use. If, upon inspection, a subject notices that there is a residual powdered therapeutic formulation in a reservoir, the subject can activate a pump once or multiple times and then check by visual inspection of the clear or translucent nozzle to see if there was sufficient delivery. This process can be repeated as needed to ensure that an adequate dose is delivered. The nozzle can be composed partially or entirely of opaque or substantially opaque materials. For example, if the device contains a light-sensitive powdered therapeutic formulation, an opaque nozzle or substantially opaque material can protect the light-sensitive powdered therapeutic formulation from exposure to light.

Nozzle Rigidity

A nozzle material can be a soft, pliable or malleable material such that the nozzle can conform to the shape of a nostril of a subject. A nozzle can be composed of rigid, substantially rigid, flexible, or substantially flexible materials, or a combination thereof. A nozzle can be a rigid material such as a polymer, plastic, silicone, metal, or a composite at one end, and a soft, malleable, or pliable material at another end, such as, for example the end of the nozzle that is placed in the nostril. The soft, pliable, or malleable material can provide the advantage of reducing the likelihood of injury during contact between a nostril of a subject and the nozzle. The reduction of likelihood of an injury can be useful if a device is used by a third party such as a doctor, a nurse, a nursing home attendant, an emergency medical technician, a paramedic, a parent, a guardian or other caregiver to deliver a powdered therapeutic formulation to a subject (e.g., a child or an elderly person).

Nozzle/Nasal Insertion

In some instances, a nozzle is of a size to substantially fit inside a nostril of a subject. For example, at least about: 10%, 20%, 25%, 30%, 40%, 50%, 60%, 70%, 75%, 80%, 90%, or 95% of the nozzle can fit inside a nostril of a subject during use of a device. Less than about: 10%, 20%, 25%, 30%, 40%, 50%, 60%, 70%, 75%, 80%, 90%, or 95% of the nozzle can fit inside a nostril of a subject during use of a device. Between about 5% and about 90% of the nozzle of a device can fit inside the nostril of a subject during use of a device. In some instances, between about: 5% and 75%, 10% and 50%, 10% and 30%, 20% and 60%, or 30% and 90% of the nozzle of a device can fit inside the nostril of a subject during use of a device. About: 10%, 20%, 25%, 30%, 40%, 50%, 60%, 70%, 75%, 80%, 90%, or 95% of the nozzle can fit inside a nostril of a subject during use of a device.

Nozzle Pipe/Nasal Insertion

The nozzle can comprise a nozzle pipe for insertion into a nostril and a base section, e.g., for attachment to a pump. In some instances, a nozzle pipe is of a size to substantially fit inside a nostril of a subject. For example, at least about: 10%, 20%, 25%, 30%, 40%, 50%, 60%, 70%, 75%, 80%, 90%, or 95% of the nozzle pipe can fit inside a nostril of a subject during use of a device. Less than about: 10%, 20%, 25%, 30%, 40%, 50%, 60%, 70%, 75%, 80%, 90%, or 95% of the nozzle pipe can fit inside a nostril of a subject during use of a device. Between about 5% and about 90% of the nozzle pipe of a device can fit inside the nostril of a subject during use of a device. In some instances, between about: 5% and 75%, 10% and 50%, 10% and 30%, 20% and 60%, or 30% and 90% of the nozzle pipe of a device can fit inside the nostril of a subject during use of a device. About: 10%, 20%, 25%, 30%, 40%, 50%, 60%, 70%, 75%, 80%, 90%, or 95% of the nozzle pipe can fit inside a nostril of a subject during use of a device. In some instances, a nozzle base section can fit inside a nostril of a subject. For example, at least about: 10%, 20%, 25%, 30%, 40%, 50%, 60%, 70%, 75%, 80%, 90%, or 95% of the nozzle base can fit inside a nostril of a subject during use of a device. Less than about: 10%, 20%, 25%, 30%, 40%, 50%, 60%, 70%, 75%, 80%, 90%, or 95% of the nozzle base can fit inside a nostril of a subject during use of a device. Between about 5% and about 90% of the nozzle base of a device can fit inside the nostril of a subject during use of a device. In some instances, between about: 5% and 75%, 10% and 50%, 10% and 30%, 20% and 60%, or 30% and 90% of the nozzle base of a device can fit inside the nostril of a subject during use of a device. About: 10%, 20%, 25%, 30%, 40%, 50%, 60%, 70%, 75%, 80%, 90%, or 95% of the nozzle base can fit inside a nostril of a subject during use of a device. Alternatively, in some instances, the nozzle base section does not fit inside a nostril of the subject.

Nozzle Length

The length of nozzle can be measured from an upstream end to a downstream end, where upstream and downstream denote the direction of flow of air or other propellant during operation of a device (i.e., air or other propellant can flow from upstream to downstream). The length of a nozzle can include the length of a nozzle pipe and a nozzle base section. The length of nozzle can be the length of a nozzle pipe. The upstream to downstream length of the nozzle can be less than about 5 cm, less than about 4.5 cm, less than about 4 cm, less than about 3.5 cm, less than about 3 cm, less than about 2.5 cm, less than about 2 cm, less than about 1.5 cm, less than about 1.0 cm, or less than about 0.5 cm. The length of the nozzle can be between about 0.5 cm and 5 cm, between about 1 cm and 5 cm, between about 1 cm and 4 cm, between about 1 cm and 3 cm, between about 2 cm and 5 cm, or between about 2 cm and 4 cm in length. The length of the nozzle can be about: 0.5 cm, 1 cm, 1.5 cm, 2 cm, 2.5 cm, 3 cm, 3.5 cm, 4 cm, 4.5 cm, or 5 cm. The length of the nozzle can be more than about: 0.5 cm, 1 cm, 1.5 cm, 2 cm, 2.5 cm, 3 cm, 3.5 cm, 4 cm, 4.5 cm, or 5 cm.

Nozzle Pipe Length

A nozzle can comprise a nozzle pipe for insertion into a nostril and a throat section for attachment to a pump. The length of a nozzle pipe can be measured from an upstream end to a downstream end, where upstream and downstream denote the direction of flow of air or other propellant during operation of a device (i.e., air or other propellant can flow from upstream to downstream). The upstream to downstream length of the nozzle pipe can be less than about 5 cm, less than about 4.5 cm, less than about 4 cm, less than about 3.5 cm, less than about 3 cm, less than about 2.5 cm, less than about 2 cm, less than about 1.5 cm, or less than about 1.0 cm. The length of the nozzle pipe can be between about 0.5 cm and 5 cm, between about 1 cm and 5 cm, between about 1 cm and 4 cm, between about 1 cm and 3 cm, between about 2 cm and 5 cm, or between about 2 cm and 4 cm in length. The length of the nozzle pipe can be about: 0.5 cm, 1 cm, 1.5 cm, 2 cm, 2.5 cm, 3 cm, 3.5 cm, 4 cm, 4.5 cm, or 5 cm. The length of the nozzle pipe can be more than about: 0.5 cm, 1 cm, 1.5 cm, 2 cm, 2.5 cm, 3 cm, 3.5 cm, 4 cm, 4.5 cm, or 5 cm.

External Nozzle Width

In some instances, the external width perpendicular to the upstream to downstream axis of the nozzle at its widest section is about: 0.1 cm to 4 cm, 1 cm to 4 cm, 1 cm to 3 cm, 1 cm to 2 cm, 2 cm to 4 cm, or 2 cm to 3 cm, 0.1 cm to 2 cm, 0.5 cm to 2 cm, or 1 cm to 2 cm. In some instances, the external width perpendicular to the upstream to downstream axis of the nozzle at its widest section is no more than about: 0.5 cm, 1 cm, 1.5 cm, 2 cm, 2.5 cm, 3 cm, 3.5 cm, 4 cm, 4.5 cm, or 5 cm wide. In some instances, the external width perpendicular to the upstream to downstream axis of the nozzle at its widest section is about: 0.1 cm, 0.2 cm, 0.3 cm, 0.4 cm, 0.5 cm, 0.6 cm, 0.7 cm, 0.8 cm, 0.9 cm, 1.0 cm, 1.2 cm, 1.4 cm, 1.6 cm, 1.8 cm, 2.0 cm, 2.2 cm, 2.4 cm, 2.6 cm, 2.8 cm, 3 cm, 3.2 cm, 3.4 cm, 3.6 cm, 3.8 cm, 4 cm, 4.2 cm, 4.4 cm, 4.6 cm, 4.8 cm, or 5 cm. In some instances, the external width perpendicular to the upstream to downstream axis of the nozzle at its widest section is more than about: 0.1 cm, 0.2 cm, 0.3 cm, 0.4 cm, 0.5 cm, 0.6 cm, 0.7 cm, 0.8 cm, 0.9 cm, 1.0 cm, 1.2 cm, 1.4 cm, 1.6 cm, 1.8 cm, 2.0 cm, 2.2 cm, 2.4 cm, 2.6 cm, 2.8 cm, 3 cm, 3.2 cm, 3.4 cm, 3.6 cm, 3.8 cm, 4 cm, 4.2 cm, 4.4 cm, 4.6 cm, 4.8 cm, or 5 cm.

In some instances, the external width perpendicular to the upstream to downstream axis of the nozzle at its narrowest section is no more than about: 0.1 cm, 0.25 cm, 0.5 cm, 0.75 cm, 1.0 cm, 1.5 cm, 2.0 cm, 2.5 cm, or 3.0 cm. In some instances, the external width perpendicular to the upstream to downstream axis of the nozzle at its narrowest section lies within the range of about: 0.5 cm to 3.0 cm; 1.0 to 2.5 cm, 1.0 to 2.0 cm, 0.1 cm to 2.0 cm, or 0.5 cm to 1.5 cm. In some instances, the external width perpendicular to the upstream to downstream axis of the nozzle at its narrowest section is about: 0.1 cm, 0.2 cm, 0.3 cm, 0.4 cm, 0.5 cm, 0.6 cm, 0.7 cm, 0.8 cm, 0.9 cm, 1.0 cm, 1.2 cm, 1.4 cm, 1.6 cm, 1.8 cm, 2.0 cm, 2.2 cm, 2.4 cm, 2.6 cm, 2.8 cm, 3 cm, 3.2 cm, 3.4 cm, 3.6 cm, 3.8 cm, 4 cm, 4.2 cm, 4.4 cm, 4.6 cm, 4.8 cm, or 5 cm. In some instances, the external width perpendicular to the upstream to downstream axis of the nozzle at its narrowest section is more than about: 0.1 cm, 0.2 cm, 0.3 cm, 0.4 cm, 0.5 cm, 0.6 cm, 0.7 cm, 0.8 cm, 0.9 cm, 1.0 cm, 1.2 cm, 1.4 cm, 1.6 cm, 1.8 cm, 2.0 cm, 2.2 cm, 2.4 cm, 2.6 cm, 2.8 cm, 3 cm, 3.2 cm, 3.4 cm, 3.6 cm, 3.8 cm, 4 cm, 4.2 cm, 4.4 cm, 4.6 cm, 4.8 cm, or 5 cm.

The width of the nozzle can vary continuously, can vary in a step-wise fashion, does not vary, or a combination thereof. The inner width or the outer width of the nozzle can vary continuously, can vary in a step-wise fashion, does not vary, or a combination thereof. The upstream and downstream ends of the nozzle can be the same width or different. In some instances, the narrowest end is the end that is placed in a nostril of a subject before and during administration. In some instances, the widest and narrowest sections of a nozzle are at the ends. For example, the widest section of a nozzle can be at the upstream end and the narrowest section of the nozzle can be at the downstream end, or vice versa. In some instances, the widest and/or narrowest sections of a nozzle are not at the end. In some instances, the widest section of a nozzle houses a powdered therapeutic formulation reservoir. In some instances, the widest section of a nozzle is a nozzle base for attachment to a manual air pump.

Internal Nozzle Width

In some instances, the internal width perpendicular to the upstream to downstream axis of the nozzle at its widest section is between about: 0.1 cm to 4 cm, 1 cm to 4 cm, 1 cm to 3 cm, 1 cm to 2 cm, 2 cm to 4 cm, 2 cm to about 3 cm, 0.1 cm to 2 cm, 0.5 cm to 2 cm, or 1 cm to 2 cm. In some instances, the internal width perpendicular to the upstream to downstream axis of the nozzle at its widest section is no more than about: 0.5 cm, 1 cm, 1.5 cm, 2 cm, 2.5 cm, 3 cm, 3.5 cm, 4 cm, 4.5 cm, or 5 cm wide. In some instances, the internal width perpendicular to the upstream to downstream axis of the nozzle at its widest section is more than about: 0.5 cm, 1 cm, 1.5 cm, 2 cm, 2.5 cm, 3 cm, 3.5 cm, 4 cm, 4.5 cm, or 5 cm wide. In some instances, the internal width perpendicular to the upstream to downstream axis of the nozzle at its widest section is about: 0.1 cm, 0.2 cm, 0.3 cm, 0.4 cm, 0.5 cm, 0.6 cm, 0.7 cm, 0.8 cm, 0.9 cm, 1.0 cm, 1.2 cm, 1.4 cm, 1.6 cm, 1.8 cm, 2.0 cm, 2.2 cm, 2.4 cm, 2.6 cm, 2.8 cm, 3 cm, 3.2 cm, 3.4 cm, 3.6 cm, 3.8 cm, 4 cm, 4.2 cm, 4.4 cm, 4.6 cm, 4.8 cm, or 5 cm.

In some instances, the internal width perpendicular to the upstream to downstream axis of the nozzle at its narrowest section is no more than about: 0.1 cm, 0.25 cm, 0.5 cm, 0.75 cm, 1.0 cm, 1.5 cm, 2.0 cm, 2.5 cm, or 3.0 cm. In some instances, the internal width perpendicular to the upstream to downstream axis of the nozzle at its narrowest section is more than about: 0.1 cm, 0.25 cm, 0.5 cm, 0.75 cm, 1.0 cm, 1.5 cm, 2.0 cm, 2.5 cm, or 3.0 cm. In some instances, the internal width perpendicular to the upstream to downstream axis of the nozzle at its narrowest section lies within the range of about: 0.5 cm to 3.0 cm; 1.0 to 2.5 cm, 1.0 to 2.0 cm, 0.1 cm to 2.0 cm, or 0.5 cm to 1.5 cm. In some instances, the internal width perpendicular to the upstream to downstream axis of the nozzle at its narrowest section is about: 0.1 cm, 0.2 cm, 0.3 cm, 0.4 cm, 0.5 cm, 0.6 cm, 0.7 cm, 0.8 cm, 0.9 cm, 1.0 cm, 1.2 cm, 1.4 cm, 1.6 cm, 1.8 cm, 2.0 cm, 2.2 cm, 2.4 cm, 2.6 cm, 2.8 cm, 3 cm, 3.2 cm, 3.4 cm, 3.6 cm, 3.8 cm, 4 cm, 4.2 cm, 4.4 cm, 4.6 cm, 4.8 cm, or 5 cm.

Nozzle Internal Volume

The nozzle can be hollow and can contain an internal volume. The internal volume of a nozzle can be about: 5 $cm^3$ or less, 4 $cm^3$ or less, 3 $cm^3$ or less, 2 $cm^3$ or less, 1 $cm^3$ or less, 0.5 $cm^3$ or less. In some instances, the internal volume of a nozzle is between about 1 $cm^3$ and about 5 $cm^3$, between about 1 $cm^3$ and about 4 $cm^3$, between about 1 $cm^3$ and about 3 $cm^3$, between about 1 $cm^3$ and about 2 $cm^3$, between about 0.1 $cm^3$ and 2 $cm^3$, and between about 0.1 $cm^3$ and about 1 $cm^3$. The internal volume of the nozzle can be about: 0.1, 0.2, 0.3, 0.4, 0.5, 0.6, 0.7, 0.8, 0.9, 1.0, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, or 5.0 $cm^3$. The internal volume of the nozzle can be more than about: 0.5, 1, 1.5, 2, 2.5, 3, 3.5, 4, 4.5, or 5 $cm^3$. The internal volume of the nozzle can be less than about: 0.5, 1, 1.5, 2, 2.5, 3, 3.5, 4, 4.5, or 5 $cm^3$.

Nozzle as a Reservoir

A nozzle can comprise a powdered therapeutic formulation reservoir adapted to contain a powdered therapeutic formulation for delivery into a nostril of a subject. In some instances, a powdered therapeutic reservoir is formed entirely by the nozzle. In other instances, a reservoir is formed in part by the nozzle and in part by a poppet valve of a device and/or a pump or components thereof. For example, the downstream end of a reservoir can be formed by a nozzle, and the upstream end of a reservoir can be formed by poppet valve and the pump and components thereof. A reservoir can be an integral part of the nozzle in that it cannot be removed or replaced separately from removing or replacing the nozzle itself. A reservoir can be a separate replaceable, insertable, or removable part. In some instances, the replaceable, insertable, or removable reservoir takes the form of a capsule or cartridge. In some instances, the replaceable reservoir is not a capsule. There can be a poppet valve or other means for regulating the flow of air, propellant, or powdered therapeutic from a reservoir. There can be a poppet valve or other means for regulating the flow of air, propellant, or powdered therapeutic into a reservoir. In some instances, a nozzle houses a separate powdered therapeutic formulation reservoir that is disposed within the nozzle adapted to contain a powdered therapeutic formulation for delivery into the nostril of a subject. By designing the drug reservoir in the nozzle, close to the exit opening, the amount of residual drug after activation of the device can be minimized, e.g., for a sticky drug or for powders that stick to plastic due to, e.g., adhesivity, electrostatic, etc.

Nozzle Reservoir Volume

In some instances, a powdered therapeutic formulation reservoir is about: 5 $cm^3$ or less, 4 $cm^3$ or less, 3 $cm^3$ or less, 2 $cm^3$ or less, 1 $cm^3$ or less, or 0.5 $cm^3$ or less in volume. In some instances, a powdered therapeutic formulation reservoir is between about 1 $cm^3$ and about 5 $cm^3$, between about 1 $cm^3$ and about 4 $cm^3$, between about 1 $cm^3$ and about 3 $cm^3$, between about 1 $cm^3$ and about 2 $cm^3$, between about 0.1 $cm^3$ and 2 $cm^3$, and between about 0.1 $cm^3$ and about 1 $cm^3$ in volume. A powdered therapeutic formulation reservoir can be about: 0.1, 0.2, 0.3, 0.4, 0.5, 0.6, 0.7, 0.8, 0.9, 1.0, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, or 5.0 $cm^3$ in volume. A powdered therapeutic formulation reservoir can be more than about: 0.5, 1, 1.5, 2, 2.5, 3, 3.5, 4, 4.5, or 5 $cm^3$ in volume. A powdered therapeutic formulation reservoir can be less than about: 0.5, 1, 1.5, 2, 2.5, 3, 3.5, 4, 4.5, or 5 $cm^3$ in volume.

Amount of Powdered Therapeutic Formulation in the Reservoir

In some instances, a reservoir is suitable for storing a dose of a powdered therapeutic formulation of about: between about 1 mg and 200 mg, between about 2 mg and 100 mg, between about 5 mg and 50 mg, between about 10 mg and 50 mg, between about 10 mg and 40 mg, or between about 10 mg and 25 mg of a powdered therapeutic formulation. In some instances, a reservoir is suitable for storing at least about: 1 mg, 5 mg, 10 mg, 20 mg, 30 mg, 40 mg, 50 mg, 60 mg, 70 mg, 80 mg, 90 mg, 100 mg, 150 mg, or 200 mg of a powdered therapeutic formulation. In some instances, a reservoir is suitable for storing at most about: 1 mg, 2.5 mg, 5 mg, 7.5 mg, 10 mg, 20 mg, 30 mg, 40 mg, 50 mg, 60 mg, 70 mg, 80 mg, 90 mg, 100 mg, 150 mg, or 200 mg of a powdered therapeutic formulation. A reservoir can store about: 1 mg, 2.5 mg, 5 mg, 7.5 mg, 10 mg, 20 mg, 30 mg, 40 mg, 50 mg, 60 mg, 70 mg, 80 mg, 90 mg, 100 mg, 150 mg, or 200 mg of a powdered therapeutic formulation. In some instances, a reservoir is configured to hold a single dose of a powdered therapeutic formulation while in some instances a reservoir is configured to hold multiple (e.g., 2, 3, 4, 5, 6, 7, 8, 9, 10) doses of a powdered therapeutic formulation. A dose can refer to the amount of powdered therapeutic formulation that a subject uses at a time.

A reservoir can be filled with a powdered therapeutic formulation during manufacture of a device. A reservoir can be filled with a powdered therapeutic formulation prior to affixing or attaching the nozzle to a pump. A reservoir can be filled after affixing or attaching a nozzle to a pump or a combination thereof.

Internal Nozzle Wall and Slits

The internal nozzle wall can also comprise one or more slits (canals or grooves). A slit or groove can be formed by a curved surface, two surfaces, three surfaces, four surfaces, five surfaces, six surfaces, seven surfaces, eight surfaces, nine surfaces, or 10 surfaces. An internal nozzle wall can have slits or grooves with at least 1, 2, 3, 4, 5, 6, 7, 8, 9, or 10 different forms. The one or more slits can be used to create a vortex in the reservoir of the device when the device is activated (e.g., when air enters a powdered therapeutic formulation reservoir from a pump). The vortex can enable complete delivery of the powdered therapeutic formulation. The one or more slits can be positioned to permit laminar air flow in the reservoir.

Slit or Groove Number

The internal nozzle wall can have at least about: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 slits or grooves. The internal nozzle wall can have less than about: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 slits or grooves. The internal nozzle wall can have about: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 slits or grooves. The internal nozzle wall can have about: 1-100, 1-90, 1-80, 1-70, 1-60, 1-50, 1-40, 1-30, 1-25, 1-20, or 1-10 slits or grooves.

Slit or Groove Positioning

The slits or grooves can be substantially parallel to each other in the internal nozzle wall. In some instances, all the slits or grooves are not substantially parallel to each other in the internal nozzle wall. In some instances, all the slits or grooves are not evenly spaced in the internal nozzle wall. In some instances, all the slits or grooves are evenly spaced on the internal nozzle wall.

Slit or Groove Length

A slit or groove can be about: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mm in length. A slit or groove can be less than about: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mm in length. A slit or groove can be more than about: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mm in length.

Powdered Therapeutic Formulation Reservoir Shape

A powdered therapeutic formulation reservoir is not limited to any particular shape and can be disposed within a nozzle as a sphere, an ellipsoid, a cylinder, a cuboid, a frustum, or any other suitable shape such as any of the shapes described herein. In some instances, the shape of a reservoir is chosen to minimize the presence of corners, sharp edges, or other surface features that can disrupt airflow. In some instances, the shape of a reservoir is chosen to eliminate areas that do not experience uniform, laminar or high airflow during operation of a device. This can have the effect of reducing places within a reservoir and the nozzle where the powdered therapeutic formulation can clump or accumulate and thereby lower the total amount of powdered therapeutic formulation delivered to the nostril of the subject. For example, the shape of a powdered therapeutic formulation reservoir can be a frustum, or parallelepiped in which all corners have been rounded off. In some instances, a powdered therapeutic formulation reservoir is composed of two or more shapes such as any of the shapes provided herein. For example, a powdered therapeutic formulation reservoir can include a cylinder shaped portion and a cone shaped portion. Alternatively, by way of example only, a powdered therapeutic formulation reservoir can include two cone shaped portions joined at their widest ends or two cone shaped portions linked by an intervening cylinder shaped portion. In some instances, the internal surface of the powdered therapeutic formulation reservoir is smooth. Alternatively, the internal surface can be rough. In some instances, one or more internal surface feature can be provided within the powdered therapeutic formulation reservoir. One or more ridges, grooves, protrusions, bumps, channels, or other surface features can be provided on the internal surface of the reservoir. Such surface features can affect the air flow and delivery of the powdered therapeutic formulation.

Nozzle Flow Restrictor

A nozzle can contain a flow restrictor adapted to restrict the flow of air through at least a portion of a device and thereby increase or decrease the velocity of, or redirect, the airflow within a device. In some instances, a flow restrictor is at the downstream end of the nozzle. A flow restrictor can be at the upstream end of the nozzle. There can be a flow restrictor at both the upstream and downstream end of a nozzle. In some instances, a flow restrictor is disposed at the downstream end of the nozzle and smoothly narrows in width from the upstream to the downstream end. Alternatively, a flow restrictor can narrow in a stepwise fashion, or can narrow in a combination of stepwise and continuously from the upstream to the downstream end. This narrowing can provide for increased velocity of air and/or powdered therapeutic from the nozzle into the nostril of the subject during operation of a device. In some instances, a flow restrictor disposed at the downstream end of a nozzle narrows down to a nozzle hole from which air and powdered therapeutic exits the nozzle during operation.

Nozzle Flow Restrictor Shape

A flow restrictor can provide for the redirection of air or other propellant from along the inner walls of the nozzle and into the center of the airflow stream. A flow restrictor can be configured to direct the flow of air from along the inner walls of the nozzle in a laminar like fashion. A flow restrictor can be configured to direct the airflow into a powdered therapeutic formulation reservoir in a turbulent fashion. A flow restrictor can be configured to provide a vortex in at least a portion of a powdered therapeutic formulation reservoir during use of a device. The redirected flow of air provided by the flow restrictor can break up at least a portion of aggregates or clumps of a powdered therapeutic formulation present in a reservoir. The redirected flow of air can ensure that a substantial fraction of a powdered therapeutic formulation present in a reservoir is delivered to the nostril of a subject during routine use of a device. For example, the redirected flow of air provided by a flow restrictor can turbulently mix and therefore effectively aerosolize a powdered therapeutic. A flow restrictor can be any of a number of shapes including but not limited to a cone, a cylinder, tapered cylinder, a frustum, and a parallelepiped or any other shape provided herein, including a combination of one or more shapes.

Nozzle Flow Restrictor Width

A flow restrictor can vary in width from slightly smaller than the width of a nozzle down to the width of a nozzle hole. For example, a flow restrictor can vary in width from at least about: 0.1 mm, 0.2 mm, 0.3 mm, 0.4 mm, 0.5 mm, 0.6 mm, 0.7 mm, 0.8 mm, 0.9 mm, 1 mm, 1.5 mm, 2 mm, 2.5 mm, 3 mm, 4 mm, 5 mm, 6 mm, 7 mm, 8 mm, 9 mm, 10 mm, 11 mm, 12 mm, 13 mm, 14 mm, or 15 mm at the widest part to less than about: 0.1 mm, 0.2 mm, 0.3 mm, 0.4 mm, 0.5 mm, 0.6 mm, 0.7 mm, 0.8 mm, 0.9 mm, 1 mm, 2 mm, 3 mm, 4 mm, 5 mm, 6 mm, 7 mm, 8 mm, 9 mm, or 10 mm at the narrowest section of the flow restrictor. A flow restrictor can be at its widest point between about 5 mm and about 15 mm wide, or between about 8 mm and about 12 mm. A flow restrictor can be at its narrowest point from about 1 mm to about 10 mm wide, about 2 mm to about 7 mm wide, about 0.1 mm to about 2 mm wide, or about 0.5 mm to about 1.5 mm wide.

Nozzle Flow Restrictor Length

A flow restrictor can have an upstream to downstream length of at least about: 20 mm, 15 mm, 10 mm, 5 mm, 4 mm, 3 mm, 2 mm, or 1 mm. A flow restrictor can have an upstream to downstream length of less than about: 20 mm, 15 mm, 10 mm, 5 mm, 4 mm, 3 mm, 2 mm, or 1 mm. A flow restrictor can be between about 5 mm and about 20 mm long, between about 5 mm and about 15 mm long, between about 5 mm and about 10 mm long, between about 1 mm and about 5 mm long, or between about 0.5 mm and about 2.5 mm long. A flow restrictor can be about: 0.5 mm, 1 mm, 1.5 mm, 2 mm, 2.5 mm, 3 mm, 3.5 mm, 4 mm, 4.5 mm, 5 mm, 5.5 mm, 6 mm, 6.5 mm, 7 mm, 7.5 mm, 8 mm, 8.5 mm, 9 mm, 9.5 mm, or 10 mm long.

Nozzle Hole

A nozzle hole can be adapted to allow the exit of a powdered therapeutic formulation from the nozzle as a single stream. In some instances, a nozzle has multiple holes that can emit a powdered therapeutic formulation as multiple streams that remain separate or that can combine into a single stream. In some instances, a nozzle hole is disposed at the downstream end of the nozzle. In some instances, a nozzle hole is also the downstream end of the flow restrictor. A nozzle hole can be any of a number of shapes including but not limited to a circle, oval, triangle, rectangle, or combination thereof. In some instances, a nozzle is configured to provide a high velocity of propellant and/or powdered therapeutic into the nostril of a subject. For example, a nozzle can be configured to provide a peak propellant velocity of between about 1 m/s to about 10 m/s, about 2 m/s to about 8 m/s or about 3 m/s to about 6 m/s.

Nozzle Hole Width

In some instances, the size of the nozzle hole when there is only one hole, when measured at its widest section, is less than 20 mm, less than about 15 mm, less than about 12 mm, less than about 10 mm, less than about 8 mm, less than about 5 mm, less than about 3 mm, less than about 2 mm, less than about 1 mm, or less than about 0.5 mm. In instances where there is more than one nozzle hole the width of individual holes is less than 10 mm, less than about 8 mm, less than about 6 mm, less than about 5 mm, less than about 4 mm, less than about 3 mm, less than about 2 mm, less than about 1 mm, or less than about 0.5 mm. The width of the nozzle hole at its widest section can be about: 0.1 mm, 0.15 mm, 0.2 mm, 0.25 mm, 0.3 mm, 0.35 mm, 0.4 mm, 0.45 mm, 0.5 mm, 0.55 mm, 0.6 mm, 0.65 mm, 0.7 mm, 0.75 mm, 0.8 mm, 0.9 mm, 1 mm, 1.1 mm, 1.2 mm, 1.3 mm, 1.4 mm, 1.5 mm, 1.6 mm, 1.7 mm, 1.8 mm, 1.9 mm, 2.0 mm, 2.1 mm, 2.2 mm, 2.3 mm, 2.4 mm, 2.5 mm, 2.6 mm, 2.7 mm, 2.8 mm, 2.9 mm, 3.0 mm. A nozzle hole at its widest section can be more than about: 0.1 mm, 0.15 mm, 0.2 mm, 0.25 mm, 0.3 mm, 0.35 mm, 0.4 mm, 0.45 mm, 0.5 mm, 0.55 mm, 0.6 mm, 0.65 mm, 0.7 mm, 0.75 mm, 0.8 mm, 0.9 mm, 1 mm, 1.1 mm, 1.2 mm, 1.3 mm, 1.4 mm, 1.5 mm, 1.6 mm, 1.7 mm, 1.8 mm, 1.9 mm, 2.0 mm, 2.1 mm, 2.2 mm, 2.3 mm, 2.4 mm, 2.5 mm, 2.6 mm, 2.7 mm, 2.8 mm, 2.9 mm, 3.0 mm. A nozzle hole at its widest section can be less than about: 0.1 mm, 0.15 mm, 0.2 mm, 0.25 mm, 0.3 mm, 0.35 mm, 0.4 mm, 0.45 mm, 0.5 mm, 0.55 mm, 0.6 mm, 0.65 mm, 0.7 mm, 0.75 mm, 0.8 mm, 0.9 mm, 1 mm, 1.1 mm, 1.2 mm, 1.3 mm, 1.4 mm, 1.5 mm, 1.6 mm, 1.7 mm, 1.8 mm, 1.9 mm, 2.0 mm, 2.1 mm, 2.2 mm, 2.3 mm, 2.4 mm, 2.5 mm, 2.6 mm, 2.7 mm, 2.8 mm, 2.9 mm, 3.0 mm. A nozzle hole at its widest section can be in a range from about: 0.1 mm to 2 mm, 0.5 mm to 1.5 mm, or 0.75 mm to 1.25 mm.

Nozzle Hole Depth

In some instances, the upstream to downstream depth of a nozzle hole, that is the length of the channel formed from the surface of a nozzle at the site of the hole to the tip of a reservoir or flow restrictor, is less than about 50 mm, less than about 40 mm, less than about 30 mm, less than about 25 mm, less than about 20 mm, less than about 15 mm, less than about 10 mm, less than about 7 mm, less than about 5 mm, less than about 3 mm, or less than about 1 mm. In some instances, the surface of a nozzle at the site of the hole is the downstream top of a reservoir or flow restrictor effectively producing a depth of 0 mm. A nozzle hole depth can be more than about: 0.1 mm, 0.25 mm, 0.5 mm, 0.75 mm, 1 mm, 1.5 mm, 2 mm, 3 mm, 4 mm, 5 mm, 6 mm, 7 mm, 8 mm, 9 mm, 10 mm, 12.5 mm, 15 mm, 17.5 mm, 20 mm, 22.5 mm, 25 mm, 27.5 mm, 30 mm, 35 mm, 40 mm, 45 mm, or 50 mm. A nozzle hole depth can be about 0.1 mm, 0.25 mm, 0.5 mm, 0.75 mm, 1 mm, 1.5 mm, 2 mm, 3 mm, 4 mm, 5 mm, 6 mm, 7 mm, 8 mm, 9 mm, 10 mm, 12.5 mm, 15 mm, 17.5 mm, 20 mm, 22.5 mm, 25 mm, 27.5 mm, 30 mm, 35 mm, 40 mm, 45 mm, or 50 mm.

Nozzle Base

A nozzle can also include a base. A base can be adapted to provide for a flow of air from a manual air chamber to a powdered therapeutic formulation reservoir or a nozzle. In some instances, a base is at the upstream end of a nozzle. A throat can additionally or alternatively be at the upstream end of a reservoir. In some instances, a base is a part of a nozzle. A base can form part of the upstream end of a powdered therapeutic formulation reservoir. In some instances, a base is partially formed by a nozzle and partially formed by a poppet valve. In some instances, a base can accommodate all or part of a poppet valve.

A base can be configured to provide for air or propellant egress from a manual air pump, thereby allowing it to enter a nozzle and/or powdered therapeutic formulation reservoir. In some instances, a base is configured to house a poppet valve or a portion of a poppet valve. In some instances, a throat is configured to slidably house a poppet valve or a portion of a poppet valve. In some instances, a poppet valve disposed within a base restrains a powdered therapeutic formulation inside a nozzle from moving upstream such as into a pump. A base can be any number of shapes including but not limited to a cone, a cylinder, tapered cylinder, a frustum, and a parallelepiped or any other shape provided herein, including a combination of one or more shapes.

In some instances, the upstream to downstream length of a base is about: less than 20 mm, less than 15 mm, less than 12 mm, less than 11 mm, less than 10 mm, less than 9 mm, less than 8 mm, less than 7 mm, less than 6 mm, less than 5 mm, less than 4 mm, or less than 2 mm. In some instances, the upstream to downstream length of a base is between about 2 mm and 20 mm, between about 5 mm and 15 mm, or between about 5 mm and 10 mm.

In some instances, the width perpendicular to the upstream to downstream axis of a base at its widest section is between about 2 mm to about 10 mm, about 2 mm to about 8 mm, or about 2 mm to about 5 mm. In some instances, the width perpendicular to the upstream to downstream axis of a base at its widest section is at least about: 1 mm, 2 mm, 3 mm, 4 mm, 5 mm, 6 mm, 7 mm, 8 mm, 9 mm, 10 mm wide, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, or 30 mm. The width perpendicular to the upstream to downstream axis of a base at its widest section can be about: 1 mm, 2 mm, 3 mm, 4 mm, 5 mm, 6 mm, 7 mm, 8 mm, 9 mm, 10 mm wide, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, or 30 mm.

A throat base can comprise one or more threads for attachment to, for example, a manual air pump and/or flexible vial. The one or more threads can be used to screw the nozzle and manual air pump together.

Cover

A nozzle can include a cover. A cover can be positioned at the downstream end of a nozzle. Alternatively, or in addition, a cover can be positioned at the downstream end of a nozzle hole. A cover can be configured to inhibit an unintentional discharge of a device. For example, a cover can be air tight preventing any airflow out of the downstream end of a nozzle and thereby preclude accidental activation of a pump from leading to discharge of a powdered therapeutic formulation. Such accidental activations can occur by rough handling of a device such as during storage or shipping. A cover can also be configured to provide an environment suitable for storage of a powdered therapeutic formulation within a powdered therapeutic formulation reservoir. For example, a cover can inhibit or block the intrusion of outside air and/or water into a nozzle and thus inhibit or block the intrusion of air or water into a powdered medicine reservoir. A cover can be a replaceable cover, such that it can be removed and replaced. With a replaceable cap, a removable band can be employed to securely fasten a cap to a nozzle. Alternatively, a cover can be a removable or breakable such that it is removed once by breaking from a nozzle or can be removed and replaced (e.g., put back into place) one or more times. A cover can be a removable or breakable tab, or a removable or breakable membrane, or a removable or breakable cap (e.g., an airtight cap).

B. Poppet Valve

A poppet valve in a device disclosed herein can be configured to regulate the flow of air from a pump and into a nozzle of a device. A poppet valve can further be configured to regulate the movement of powdered therapeutic formulation. A poppet valve can be configured to block air or gas flow from a pump into a nozzle when the device is not activated (e.g., a manual air pump is not compressed) and can permit air or gas flow from a pump into a nozzle when the device is activated (e.g., a manual air pump is compressed). In some instances, the poppet valve has one or more contacting points with the retainer, for example about 2 to about 10 inner ribs. In some instances, the poppet valve has about: 3 inner ribs. In some instances, the length of each inner rib is about: 1-20 mm, 1-10 mm, or 1-5 mm, for example about: 1, 2, 3, 4, 5, 6, 7, 8, 9, 10, 11, 12, 13, 14, 15, 16, 17, 18, 19, or 20 mm. In some instances, the length of each inner rib is about: 0.1-5 mm, for example about: 0.1, 0.2, 0.5, 1, 2, 3, 4, or 5 mm. In some instances, the height of each inner rib is about: 0.1-5 mm, for example about: 0.1, 0.2, 0.5, 1, 2, 3, 4, or 5 mm.

In some instances, a poppet valve is configured to block movement of powdered therapeutic formulation (e.g., by gravity) in an upstream direction (e.g., into a pump). A poppet valve can be configured so it can be in one position in the device when the device is not activated (e.g., a pump is not activated) and another position in the device when the device is activated (e.g., a pump is activated). A poppet valve can be configured to block movement of a powdered therapeutic formulation (e.g., by gravity) in an upstream direction (e.g., into a flexible vial and/or manual air pump) when the device is not activated (e.g., a manual air pump is not compressed) and when the device is activated (e.g., a manual air pump is compressed). The poppet valve can contain slits (or channels or grooves) diagonal to a major axis of the device that can create a vortex along the walls of the reservoir.

Poppet Valve Composition

A poppet valve can be composed of a variety of polymers, plastics, rubber, silicones, metal, composites, any other materials described herein as suitable for use in the manufacture of an intranasal delivery device, or any other material suitable for use in an intranasal delivery device. A poppet valve can be made of one material or type of material. Alternatively, a poppet valve can be composed two or more different materials or types of materials. All or a portion of a poppet valve can be a biocompatible material or a hypoallergenic material. A poppet valve can be composed of rigid, substantially rigid, flexible, or substantially flexible materials, or a combination thereof. In some instances, a poppet valve can be comprised of one or more of: cyclic olefin copolymer (COC), paper, silicone, styrene butadiene block copolymer (SBC), polyacetal, polyoxymethylene, acrylates, polyethylenes, polyurethane, hydrogel, polyester (e.g., DACRONB from E. I. Du Pont de Nemours and Company, Wilmington, Del.), polypropylene, polytetrafluoroethylene (PTFE), expanded PTFE (ePTFE), polyether ether ketone (PEEK), nylon, extruded collagen, polymer foam, rubber, silicone rubber, polyethylene terephthalate, ultra high molecular weight polyethylene, polycarbonate urethane, polyimides, aluminum, stainless steel, nickel-titanium alloy (e.g., Nitinol), titanium, stainless steel, or cobalt-chrome alloy (e.g., ELGILOYB from Elgin Specialty Metals, Elgin, Ill.; CONICHROMEB from Carpenter Metals Corp., Wyomissing, Pa.).

Poppet Valve Dimensions

A poppet valve can be any number of shapes including but not limited to a disc, an annulus, a torus, a cone, a pyramid, a cylinder, tapered cylinder, a frustum, a cuboid, and a parallelepiped or any other shape provided herein, including a combination of one or more shapes. A poppet valve can have a narrow end and a wide end. In some instances, the widest portion of a poppet valve can lie at the upstream or downstream end. In some instances, the narrowest portion of a poppet valve can lie at the upstream or downstream end. A poppet valve can be hollow. A poppet valve can have an opening at one end. In some instances, a poppet valve does not have an opening at one end.

The upstream to downstream length of a poppet valve can be less than about: 30, 29, 28, 27, 26, 25, 24, 23, 22, 21, 20, 19, 18, 17, 16, 15, 14, 13, 12, 11, 10, 9, 8, 7, 6, or 5 mm. The length of a poppet valve can be between about 5 mm and about 30 mm, between about 5 mm and about 20 mm, between about 5 mm and about 15 mm, or between about 5 mm and about 10 mm. The length the a poppet valve can be more than about: 5, 6, 7, 8, 9, 10, 11, 12, 13, 14, 15, 16, 17, 18, 19, 20, 21, 22, 23, 24, 25, 26, 27, 28, 29, or 30 mm. The length of a poppet valve can be about: 5, 6, 7, 8, 9, 10, 11, 12, 13, 14, 15, 16, 17, 18, 19, 20, 21, 22, 23, 24, 25, 26, 27, 28, 29, or 30 mm.

The width perpendicular to the upstream to downstream axis of a poppet valve at its widest section can be between about 1 mm to about 30 mm, about 1 mm to about 25 mm, about 1 mm to about 20 mm, about 1 mm to about 15 mm, about 1 mm to about 10 mm, or about 1 mm to about 5 mm. The width perpendicular to the upstream to downstream axis of a poppet valve at its widest section can be more than about: 1 mm, 2 mm, 3 mm, 4 mm, 5 mm, 6 mm, 7 mm, 8 mm, 9 mm, or 10 mm wide. The width perpendicular to the upstream to downstream axis of a poppet valve at its widest section can be less than about: 1 mm, 2 mm, 3 mm, 4 mm, 5 mm, 6 mm, 7 mm, 8 mm, 9 mm, or 10 mm wide.

The width perpendicular to the upstream to downstream axis of a poppet valve at its narrowest section can be between about 1 mm to about 30 mm, about 1 mm to about 25 mm, about 1 mm to about 20 mm, about 1 mm to about 15 mm, about 1 mm to about 10 mm, or about 1 mm to about 5 mm. In some instances, a poppet valve has a width at its narrowest section that is no more than about: 0.5 mm, 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, or 20 mm wide. In some instances, a poppet valve has a width at its narrowest section that is more than about: 0.5 mm, 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, or 20 mm wide. The width perpendicular to the upstream to downstream axis of a poppet valve at its widest section or narrowest section can be about: 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, or 20 mm wide.

Poppet Valve Dimensions Relative to Nozzle

A poppet valve can be configured to slidably fit within part or all of a nozzle. The width of part of a poppet valve can be less than the internal width of a nozzle pipe. For example, the width at the base of a top section and the width of a first cylindrical section can be less than the width of the widest part of a nozzle pipe. The difference in width of a first cylindrical section of a poppet valve and the internal width of the widest part a nozzle pipe can be about: 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.30, 0.31, 0.32, 0.33, 0.34, 0.35, 0.36, 0.37, 0.38, 0.39, 0.40, 0.41, 0.42, 0.43, 0.44, 0.45, 0.46, 0.47, 0.48, 0.49, or 0.5 mm. The difference in width of a first cylindrical section of a poppet valve and the internal width of the widest part a nozzle pipe can be less than about: 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.30, 0.31, 0.32, 0.33, 0.34, 0.35, 0.36, 0.37, 0.38, 0.39, 0.40, 0.41, 0.42, 0.43, 0.44, 0.45, 0.46, 0.47, 0.48, 0.49, or 0.5 mm. The difference in width of a first cylindrical section of a poppet valve and the internal width of the widest part a nozzle pipe can be more than about: 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.30, 0.31, 0.32, 0.33, 0.34, 0.35, 0.36, 0.37, 0.38, 0.39, 0.40, 0.41, 0.42, 0.43, 0.44, 0.45, 0.46, 0.47, 0.48, 0.49, or 0.5 mm. The difference in width of a first cylindrical section and the internal width of the widest part of a nozzle pipe can permit air to flow from a manual air pump to the nozzle when the manual air pump is activated.

Top Section

A poppet valve can have multiple sections. A poppet valve can have a top section in the shape of, e.g., a cone, a pyramid, or a trapezoid. A top section can have a convex surface. A top section can allow a powdered therapeutic formulation to accumulate along the wall of a nozzle pipe to increase flow and assist in proper air flow when the intranasal delivery device is activated. In some instances, a top section can further comprise an additional section. The additional section can be connected to the top portion of the top section and can be in the shape of, e.g., a cone, a pyramid, or a trapezoid.

Top Section Height

The height of a top section of a poppet valve can be about: 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, or 20 mm. The height of the top section of a poppet valve can be more than about: 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, or 20 mm. The height of a top section of a poppet valve can be less than about: 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, or 20 mm. The height of the top section of a poppet valve can be about: 1 to 20 mm, about: 1 to 10 mm, about: 1 to 5 mm, or about: 1 to 2.5 mm.

Top Section Width

The diameter of the bottom of a top section can be about: 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, or 20 mm. The diameter of the bottom of a top section can be more than about: 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, or 20 mm. The diameter of the bottom of a top section can be less than about: 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, or 20 mm. The diameter of the bottom of a top section can be from about: 1 to 20 mm, 1 to 10 mm, 1 to 7.5 mm, 1 to 5 mm, 2.5 to 20 mm, 2.5 to 10 mm, or 2.5 to 7.5 mm.

Top Section Angle

An angle formed by a surface of a top section of a poppet valve and a plane parallel to the base of the top section can be an obtuse angle. An obtuse angle formed by a surface of a top section of a poppet valve and a plane parallel to the base of the top section can be from about 179 degrees to about 91 degrees, from about 170 to 100 degrees, from about 160 to about 110 degrees, from about 150 to about 120 degrees, or from about 140 to about 130 degrees. An obtuse angle formed by a surface of a top section of a poppet valve and a plane parallel to the base of the top section can be about: 179, 178, 177, 176, 175, 174, 173, 172, 171, 170, 169, 168, 167, 166, 165, 164, 163, 162, 161, 160, 159, 158, 157, 156, 155, 154, 153, 152, 151, 150, 149, 148, 147, 146, 145, 144, 143, 142, 141, 140, 139, 138, 137, 136, 135, 134, 133, 132, 131, 130, 129, 128, 127, 126, 125, 124, 123, 122, 121, 120, 119, 118, 117, 116, 115, 114, 113, 112, 111, 110, 109, 108, 107, 106, 105, 104, 103, 102, 101, 100, 99, 98, 97, 96, 95, 94, 93, 92, or 91 degrees. An obtuse angle formed by a surface of a top section of a poppet valve and a plane parallel to the base of the top section can be less than about: 179, 178, 177, 176, 175, 174, 173, 172, 171, 170, 169, 168, 167, 166, 165, 164, 163, 162, 161, 160, 159, 158, 157, 156, 155, 154, 153, 152, 151, 150, 149, 148, 147, 146, 145, 144, 143, 142, 141, 140, 139, 138, 137, 136, 135, 134, 133, 132, 131, 130, 129, 128, 127, 126, 125, 124, 123, 122, 121, 120, 119, 118, 117, 116, 115, 114, 113, 112, 111, 110, 109, 108, 107, 106, 105, 104, 103, 102, 101, 100, 99, 98, 97, 96, 95, 94, 93, 92, or 91 degrees. An obtuse angle formed by a surface of a top section of a poppet valve and a plane parallel to the base of the top section can be more than about: 179, 178, 177, 176, 175, 174, 173, 172, 171, 170, 169, 168, 167, 166, 165, 164, 163, 162, 161, 160, 159, 158, 157, 156, 155, 154, 153, 152, 151, 150, 149, 148, 147, 146, 145, 144, 143, 142, 141, 140, 139, 138, 137, 136, 135, 134, 133, 132, 131, 130, 129, 128, 127, 126, 125, 124, 123, 122, 121, 120, 119, 118, 117, 116, 115, 114, 113, 112, 111, 110, 109, 108, 107, 106, 105, 104, 103, 102, 101, 100, 99, 98, 97, 96, 95, 94, 93, 92, or 91 degrees.

First Shelf of a Poppet Valve

A first shelf can connect the top section and a first cylindrical section. The shortest length of the surface of a first shelf from the base of the top section to the top of a first cylindrical section can be about: 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5 mm. The shortest length of the surface of a first shelf from the base of the top section to the top of a first cylindrical section can be more than about: 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5 mm. The shortest length of the surface of a first shelf from the base of the top section to the top of a first cylindrical section can be less than about: 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5 mm. The shortest length of the surface of a first shelf from the base of the top section to the top of a first cylindrical section can be about: 0.1 to 5 mm, 0.1 to 4 mm, 0.1 to 3 mm, 0.1 to 2 mm, 0.1 to 1.75 mm, 0.1 to 1.5 mm, 0.1 to 1.25 mm, or 0.1 to 1 mm.

An angle formed between the side of the first cylindrical section and the surface of the first shelf can be between about: 91 to 179 degrees, 100 to 170 degrees, 110 to 160 degrees, 120 to 150 degrees, or 130 to 140 degrees. An angle formed between the side of the first cylindrical section and the surface of the first shelf can be about: 179, 178, 177, 176, 175, 174, 173, 172, 171, 170, 169, 168, 167, 166, 165, 164, 163, 162, 161, 160, 159, 158, 157, 156, 155, 154, 153, 152, 151, 150, 149, 148, 147, 146, 145, 144, 143, 142, 141, 140, 139, 138, 137, 136, 135, 134, 133, 132, 131, 130, 129, 128, 127, 126, 125, 124, 123, 122, 121, 120, 119, 118, 117, 116, 115, 114, 113, 112, 111, 110, 109, 108, 107, 106, 105, 104, 103, 102, 101, 100, 99, 98, 97, 96, 95, 94, 93, 92, or 91 degrees. An angle formed between the side of the first cylindrical section and the surface of the first shelf can be more than about: 179, 178, 177, 176, 175, 174, 173, 172, 171, 170, 169, 168, 167, 166, 165, 164, 163, 162, 161, 160, 159, 158, 157, 156, 155, 154, 153, 152, 151, 150, 149, 148, 147, 146, 145, 144, 143, 142, 141, 140, 139, 138, 137, 136, 135, 134, 133, 132, 131, 130, 129, 128, 127, 126, 125, 124, 123, 122, 121, 120, 119, 118, 117, 116, 115, 114, 113, 112, 111, 110, 109, 108, 107, 106, 105, 104, 103, 102, 101, 100, 99, 98, 97, 96, 95, 94, 93, 92, or 91 degrees. An angle formed between the side of the first cylindrical section and the surface of the first shelf can be less than about: 179, 178, 177, 176, 175, 174, 173, 172, 171, 170, 169, 168, 167, 166, 165, 164, 163, 162, 161, 160, 159, 158, 157, 156, 155, 154, 153, 152, 151, 150, 149, 148, 147, 146, 145, 144, 143, 142, 141, 140, 139, 138, 137, 136, 135, 134, 133, 132, 131, 130, 129, 128, 127, 126, 125, 124, 123, 122, 121, 120, 119, 118, 117, 116, 115, 114, 113, 112, 111, 110, 109, 108, 107, 106, 105, 104, 103, 102, 101, 100, 99, 98, 97, 96, 95, 94, 93, 92, or 91 degrees. An angle formed between the side of the first cylindrical section and the surface of the first shelf can be an obtuse angle.

First Shelf Dimensions Relative to Nozzle Pipe

A first shelf can be configured to have a diameter that is wider than the internal diameter of a nozzle pipe. A first shelf can be configured to contact the base of a nozzle with the device is activated. The first shelf can be configured to prevent the entire poppet valve from entering a nozzle pipe with the device is activated. The first shelf can be configured to prevent a powdered therapeutic formulation from moving upstream in a manual air pump (e.g., a flexible vial) when the device is activated.

First Cylindrical Section of a Poppet Valve

The first shelf can be connected at its base to a first cylindrical section. The width of the first cylindrical section can be the same as the width of the base of a first shelf.

First Cylindrical Section Height

The height of a first cylindrical section of a poppet valve can be about: 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, or 20 mm. The height of the first cylindrical section of a poppet valve can be more than about: 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, or 20 mm. The height of a first cylindrical section of a poppet valve can be less than about: 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, or 20 mm. The height of the first cylindrical section of a poppet valve can be about: 1 to 20 mm, about: 1 to 10 mm, about: 1 to 7.5 mm, about: 1 to 5 mm, about: 2.5 to 20 mm, about: 2.5 to 10 mm, about: 2.5 to 7.5 mm, or about: 2.5 to 5 mm.

First Cylindrical Section Width

The diameter of a first cylindrical section can be about: 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, or 20 mm. The diameter of a first cylindrical section can be more than about: 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, or 20 mm. The diameter of a first cylindrical section can be less than about: 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, or 20 mm. The diameter of a first cylindrical section can be from about: 1 to 20 mm, 1 to 10 mm, 1 to 7.5 mm, 1 to 5 mm, 2.5 to 20 mm, 2.5 to 10 mm, or 2.5 to 7.5 mm.

Second Shelf

A poppet valve can have a second shelf that extends inward and downward from the base of a first cylindrical section. A second shelf can be configured to cover a flow outlet on a manual air pump when the manual air pump is not compressed to prevent a powdered therapeutic formulation from moving upstream into the manual air pump.

Second Shelf Length

The shortest length of the surface of a second shelf from the bottom of the first cylindrical section to the top of the second cylindrical section can be about: 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5 mm. The shortest length of the surface of a second shelf from the bottom of the first cylindrical section to the top of the second cylindrical section can be more than about: 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5 mm. The shortest length of the surface of a second shelf from the bottom of the first cylindrical section to the top of the second cylindrical section can be less than about: 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5 mm. The shortest length of the surface of a second shelf from the bottom of the first cylindrical section to the top of the second cylindrical section can be about: 0.1 to 5 mm, 0.1 to 4 mm, 0.1 to 3 mm, 0.1 to 2 mm, 0.1 to 1.75 mm, 0.1 to 1.5 mm, 0.1 to 1.25 mm, or 0.1 to 1 mm.

Second Shelf Angle

An angle formed between the side of the second cylindrical section and the surface of the second shelf can be between about: 0 to 90 degrees, 10 to 80 degrees, 20 to 70 degrees, 30 to 60 degrees, or 40 to 50 degrees. An angle formed between the side of the second cylindrical section and the surface of the second shelf can be about: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 degrees. An angle formed between the side of the second cylindrical section and the surface of the second shelf can be more than about: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 degrees. An angle formed between the side of the second cylindrical section and the surface of the second shelf can be less than about: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 degrees. An angle formed between the side of the second cylindrical section and the surface of the second shelf can be an acute angle or a right angle.

Slits or Grooves

A second shelf can have one or more slits or grooves on the surface of the shelf. The grooves can permit air flow from a manual air pump to a nozzle with the device is activated (e.g., by compression). The one or more grooves can be used to create a vortex in the reservoir of the device when the device is activated (e.g., when air enters a powdered therapeutic formulation reservoir from a pump). The resulting vortex can enable complete delivery of the powdered therapeutic formulation. The slits or grooves can be positioned to permit laminar air flow in the reservoir.

Slit or Groove Length

A slit or groove can extend from the base of a first cylindrical section to the top of a second cylindrical section on the surface of a second shelf of a poppet valve. A slit or groove can extend about: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% of the shortest length from bottom of the first cylindrical section to the top of the second cylindrical section on the surface of the second shelf. A slit or groove can extend more than about: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% of the shortest length from bottom of the first cylindrical section to the top of the second cylindrical section on the surface of the second shelf. A slit or groove can extend less than about: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% of the shortest length from bottom of the first cylindrical section to the top of the second cylindrical section on the surface of the second shelf. A slit or groove can extend about: 1-100%, 10-100%, 20-100%, 30-100%, 40-100%, 50-100%, 60-100%, 70-100%, 80-100%, or 90-100% of the shortest length from the bottom of the first cylindrical section to the top of the second cylindrical section on the surface of the second shelf.

Angle of Slit or Groove

A slit or groove can lie at a 90 degree or non-90 degree angle relative to a line representing the shortest length from the bottom of the first cylindrical section to the top of the second cylindrical section on the surface of a second shelf. With respect to a line representing the shortest length from the bottom of the first cylindrical section to the top of the second cylindrical section on the surface of a second shelf, a slit or groove can be at an angle of about: 0 to 90 degrees, 5 to 90 degrees, 10 to 80 degrees, 15 to 75 degrees, 20 to 70 degrees, 25 to 65 degrees, 30 to 60 degrees, 35 to 55 degrees, or 40 to 50 degrees. With respect to a line representing the shortest length from the bottom of the first cylindrical section to the top of the second cylindrical section on the surface of a second shelf, a slit or groove can be at an angle of about: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 degrees. With respect to a line representing the shortest length from the bottom of the first cylindrical section to the top of the second cylindrical section on the surface of a second shelf, a slit or groove can be at an angle of more than about: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, or 89 degrees. With respect to a line representing the shortest length from the bottom of the first cylindrical section to the top of the second cylindrical section on the surface of a second shelf, a slit or groove can be at an angle of less than about: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89 or 90 degrees. When the one or more grooves are at a 0 degree angle (parallel to a line representing the shortest length from the bottom of the first cylindrical section to the top of the second cylindrical section on the surface of a second shelf) air can flow straight along the walls of the reservoir. When the grooves are at an angle of greater than 0 degrees and less than 90 degrees, a vortex can be created along the walls of the reservoir, enabling complete delivery of the drug out of the reservoir.

Slit or Groove Depth The maximum depth of a slit or groove can be about: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% of the length of a slit or groove. The maximum depth of a slit or groove can be more than about: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% of the length of a slit or groove. The maximum depth of a slit or groove can be less than about: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% of the length of a slit or groove. The maximum depth of a slit or groove can be about: 1 to 50%, 1 to 40%, 1 to 30%, 1 to 25%, 1 to 20%, 1 to 15%, 1 to 10%, 1 to 5%, or 1 to 2.5% of the length of a slit or groove.

Slit or Groove Shape

A slit or groove can be formed by a curved surface, two surfaces, three surfaces, four surfaces, five surfaces, six surfaces, seven surfaces, eight surfaces, nine surfaces, or 10 surfaces. A second shelf can have slits or grooves with at least 1, 2, 3, 4, 5, 6, 7, 8, 9, or 10 different forms.

Slit or Groove Number

A poppet valve can have at least: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 slits or grooves. A poppet valve can have less than: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 slits or grooves. A poppet valve can have about: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 slits or grooves. A poppet valve have about: 1-100, 1-90, 1-80, 1-70, 1-60, 1-50, 1-40, 1-30, 1-25, 1-20, or 1-10 slits or grooves.

Slit or Groove Positioning

When a second shelf has more than one slit or groove, the slits or grooves can be substantially parallel to each other. In some instances, all the slits or grooves are not substantially parallel to each other. In some instances, all the slits or grooves are not evenly spaced on the second shelf. In some instances, all the slits or grooves are evenly spaced on the second shelf.

Second Cylindrical Section

A poppet valve can have a second cylindrical section below the second shelf.

Second cylindrical section height. The height of a second cylindrical section of a poppet valve can be longer than the height of a first cylindrical section. The height of a second cylindrical section of a poppet valve can be shorter than the height of a first cylindrical section. The height of a second cylindrical section of a poppet valve can be about: 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, or 20 mm. The height of the first cylindrical section of a poppet valve can be more than about: 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, or 20 mm. The height of a first cylindrical section of a poppet valve can be less than about: 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, or 20 mm. The height of the first cylindrical section of a poppet valve can be about 1 to 20 mm, about 1 to 10 mm, about 1 to 7.5 mm, about 1 to 5 mm, about 1 to 4 mm, about 1 to 3 mm, or about 1 to 2 mm.

Second cylindrical section width. A second cylindrical section of a poppet valve can be wider than a first cylindrical section of a poppet valve. A second cylindrical section can be wider than the internal diameter of a nozzle pipe. A second cylindrical section can be narrower than the internal diameter of a nozzle pipe. The diameter of a second cylindrical section can be about: 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, or 20 mm. The diameter of a second cylindrical section can be more than about: 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, or 20 mm. The diameter of a second cylindrical section can be less than about: 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, or 20 mm. The diameter of a second cylindrical section can be from about: 1 to 20 mm, 1 to 10 mm, 1 to 7.5 mm, 1 to 5 mm, 2.5 to 20 mm, 2.5 to 10 mm, or 2.5 to 7.5 mm. In some instances, a second cylindrical portion of a poppet valve comprises a ridge. When a device is not activated, a ridge can rest on a bulge in the nozzle pipe. This positioning can prevent the poppet valve from moving upstream in to a manual air pump. This positioning can also prevent a powdered therapeutic formulation from moving upstream into a manual air pump. The combination of the ridge and the second cylindrical section can be wider than the width of the second cylindrical section. A ridge can be positioned anywhere along the length of a cylindrical second section. A ridge can form a ring around all or a portion of a second cylindrical section. A ridge can be any of a variety of shapes or sizes.

Base of a Poppet Valve

A poppet valve can be configured to have a base that is wider than the width of a second cylindrical section. In some instances, a base does not touch a nozzle pipe when a device is activated or when a device is not activated.

Configurations

In some instances, a poppet valve has a top section, first shelf, first cylindrical section, second shelf, and second cylindrical section or base. In some instances, the poppet valve need not have all such sections. For example, a poppet valve can be formed of a single cylinder or other shape that rests on a vial throat in its unactivated position and is positioned beneath a nozzle shoulder. The poppet valve may have one or more groove or passageway that is blocked by the vial throat when the poppet valve is resting on the vial throat. When a manual pump is compressed, the poppet valve can be pushed upward against the nozzle shoulder in its activated position, and air may flow through the one or more groove or passageway that is not blocked by the nozzle shoulder into the nozzle.

The poppet valve can have any shape with one or more sections that can allow the poppet valve to rest on the vial throat and not fall into the vial. In some instances, the poppet valve is limited in its upward movement by a nozzle shoulder or other shaped feature of the nozzle. The poppet valve can have one or more fluid flow passageway (e.g., slit, channel, groove, tunnel, tube) that is not in fluid communication with the air or gas source when the poppet valve is in an inactivated position. In some instances, the fluid flow passageway is blocked by the nozzle shoulder directly, or the fluid communication is blocked by a portion of the poppet valve resting on the vial shoulder. The fluid flow passageway can provide fluid communication between the air or gas source and the interior of the nozzle when the poppet valve is in an activated position. The fluid flow passageway can be positioned so as not to be blocked by the nozzle shoulder when the poppet valve is in an activated or inactivated position.

Retainer

Figure 2:
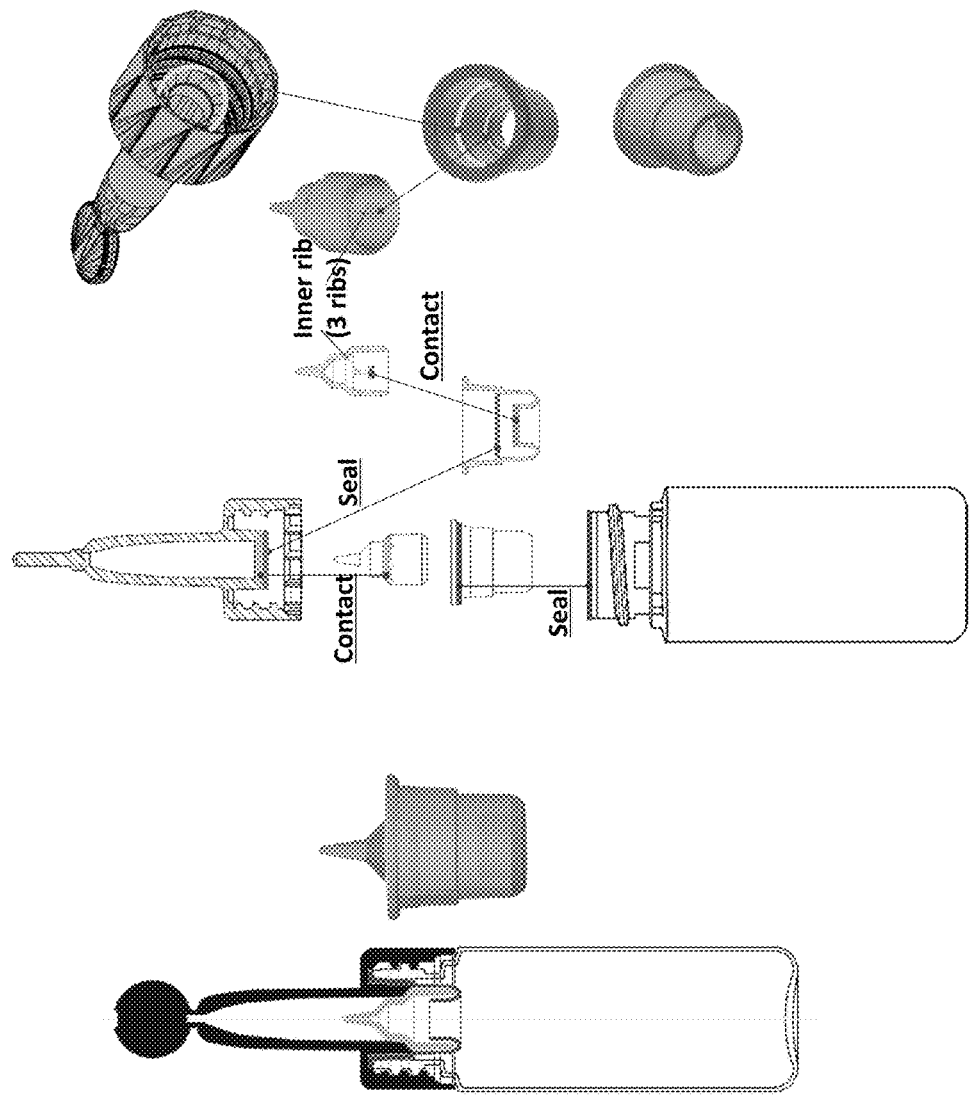
FIG. 2 illustrates contact and seal areas between the parts. The nozzle and the retainer are sealed. The retainer and the pump are also sealed. The poppet valve lifted by the retainer always contacts the nozzle, so there is no clearance between the nozzle and the poppet valve. This reduces a potential risk that powder prefilled in the nozzle falls into the pump.
Figure 3:
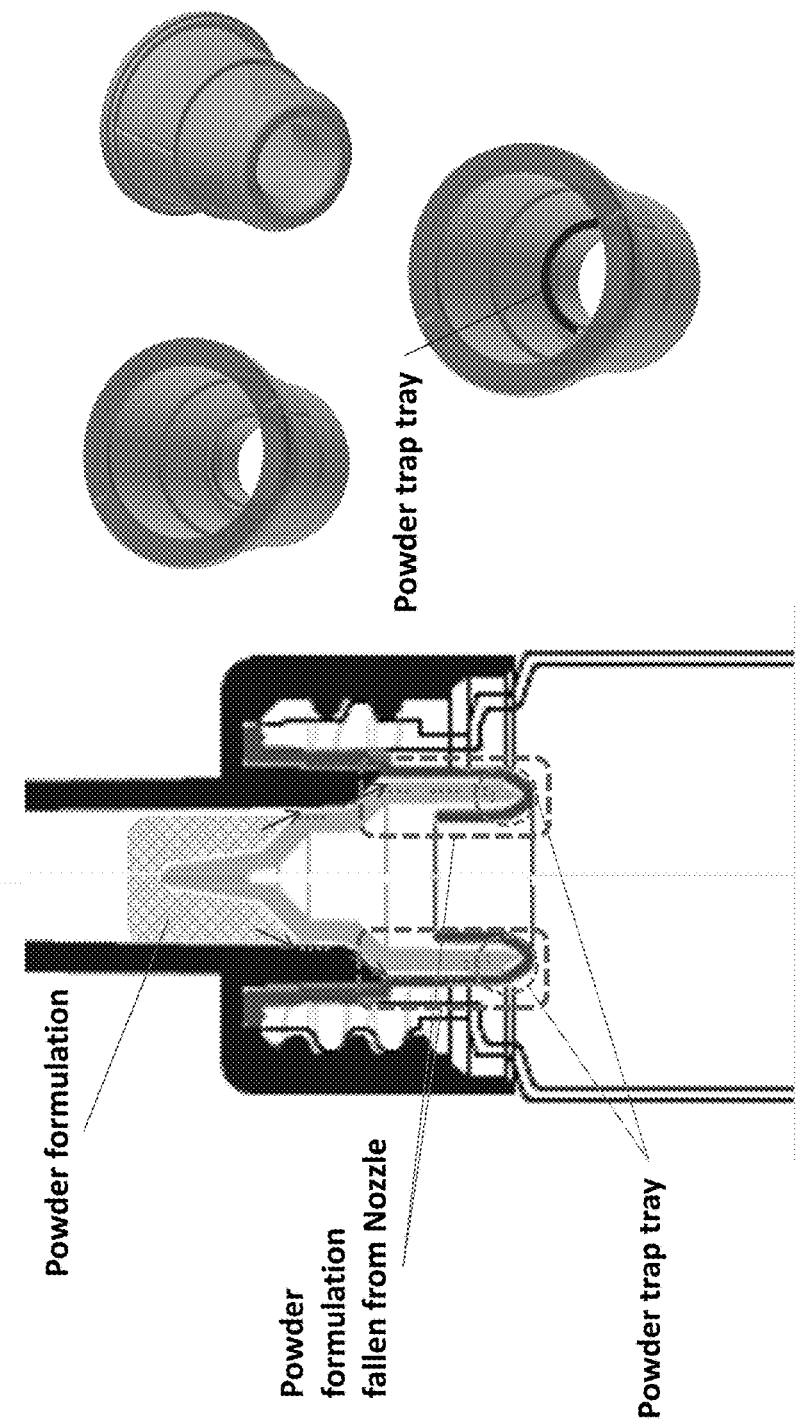
FIG. 3 illustrates that the retainer has a tray to trap powder fallen from the nozzle. This reduces a potential risk that powder from the nozzle falls into the pump.
Figure 4:
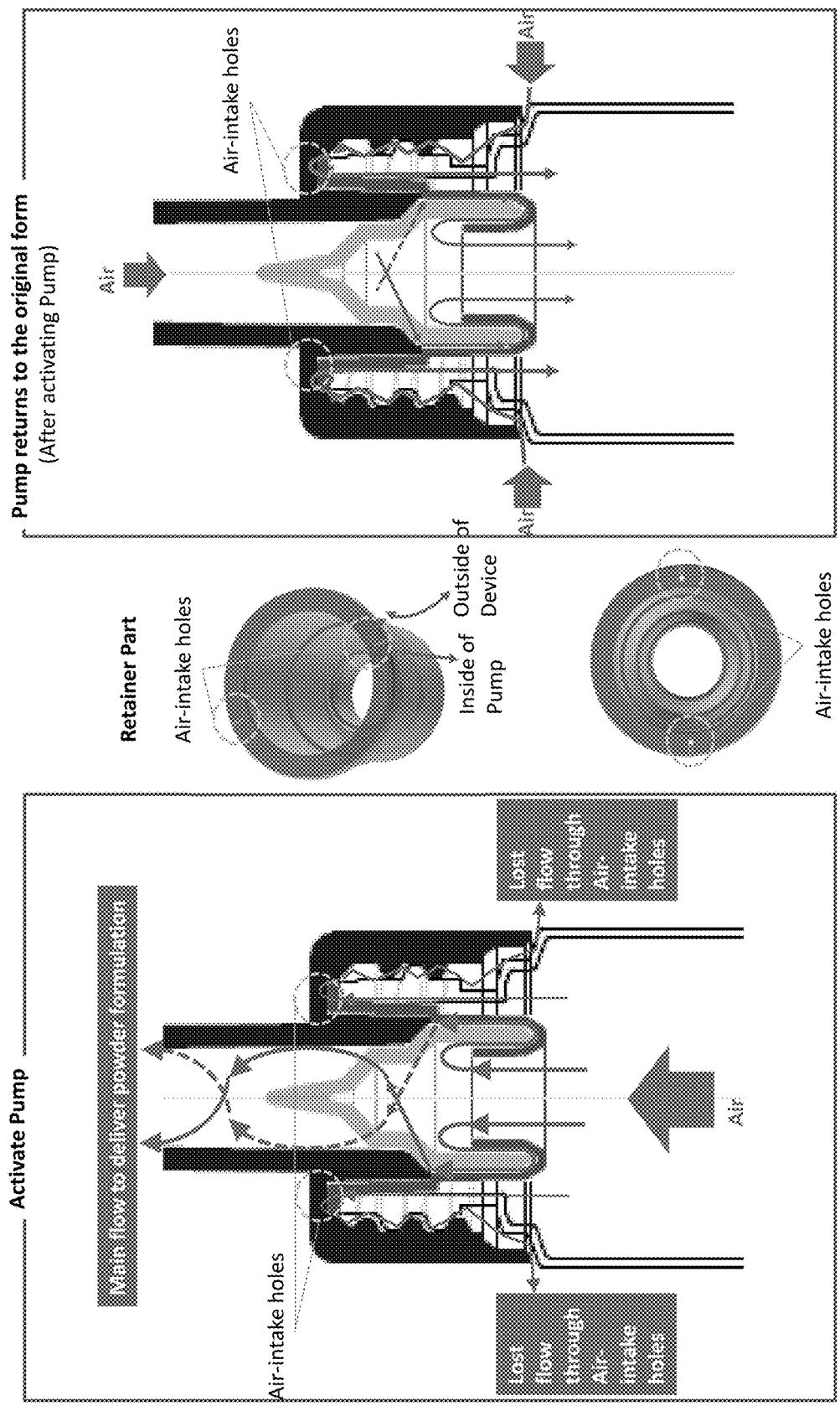
FIG. 4 illustrates the main flow to deliver powder and a side air flow to deliver trapped powder through the nozzle. If necessary, the pump may be activated up to 3 times to deliver powder. Air-intake holes in the retainer prevent the remaining powder in the nozzle from entering to the pump when the pump returns to the original form.

A device described herein can comprise a retainer, for example as shown in FIG. 1. The retainer can hold a poppet valve of the device by one more contacting points, for example one or more inner ribs (e.g., 3 ribs), for example as shown in FIG. 2. In the device, the nozzle and the retainer can be sealed; and/or the retainer and the pump can be sealed. In some instances, the retainer is hollow. In some instances, the retainer has a tray to trap powder fallen from the nozzle to prevent it from falling into the pump, for example as shown in FIG. 3. The tray can be an inner circumferential groove based from an upstream end of the retainer. In some instances, a rim of the circumferential groove of the retainer is in contact with the one or more contacting points of the poppet valve. In some instances, the inner circumferential groove has a height of 1-20 mm, for example about: 2, 3, 4, 5, 6, 7, 8, 9, 10, 11, 12, 13, 14, 15, 16, 17, 18, or 19 mm. In some instances, the retainer immobilizes the poppet valve in the device. Any trapped powder can be delivered by a side air flow through the nozzle when the device is activated, for example as shown in FIG. 4, the left panel. When the device is activated, a portion of air from the pump can flow into the retainer along the circumferential groove and travels through surface grooves of the retainer to generate a vortex into the reservoir. The retainer can have air-intake hole(s) to prevent the remaining powder in the nozzle from entering to the pump when the pump returns to the original form, for example as shown in FIG. 4, the right panel. In some instances, the retainer has 1, 2, 3, 4, 5, 6, 7, 8, 9, or 10 air intake holes. In some instances, the one or more air intake holes are about: 0.1-1, 0.1-0.5, or 0.2-0.4 mm wide, for example 0.3 mm wide. In some instances, the one or more air intake holes of the retainer allows outside air to enter the pump after the device is activated. In some instances, the retainer contains an outer circumferential rim that is wider than an opening of the pump. In some instances, the retainer is at least partially fit into the manual air pump.

A retainer can be any number of shapes including but not limited to a disc, an annulus, a torus, a cone, a pyramid, a cylinder, tapered cylinder, a frustum, a cuboid, and a parallelepiped or any other shape provided herein, including a combination of one or more shapes. A retainer can have a narrow end and a wide end. In some instances, the widest portion of a retainer can lie at the upstream or downstream end. In some instances, the narrowest portion of a retainer can lie at the upstream or downstream end. A retainer can have an opening at one end. In some instances, a retainer does not have an opening at one end.

The upstream to downstream length of a retainer can be less than about: 30, 29, 28, 27, 26, 25, 24, 23, 22, 21, 20, 19, 18, 17, 16, 15, 14, 13, 12, 11, 10, 9, 8, 7, 6, or 5 mm. The length of a retainer can be between about 5 mm and about 30 mm, between about 5 mm and about 20 mm, between about 5 mm and about 15 mm, or between about 5 mm and about 10 mm. The length the a retainer can be more than about: 5, 6, 7, 8, 9, 10, 11, 12, 13, 14, 15, 16, 17, 18, 19, 20, 21, 22, 23, 24, 25, 26, 27, 28, 29, or 30 mm. The length of a retainer can be about: 5, 6, 7, 8, 9, 10, 11, 12, 13, 14, 15, 16, 17, 18, 19, 20, 21, 22, 23, 24, 25, 26, 27, 28, 29, or 30 mm.

The width perpendicular to the upstream to downstream axis of a retainer at its widest section can be about 1 mm to about 30 mm, about 1 mm to about 25 mm, about 1 mm to about 20 mm, about 1 mm to about 15 mm, about 1 mm to about 10 mm, or about 1 mm to about 5 mm. The width perpendicular to the upstream to downstream axis of a retainer at its widest section can be more than about: 1 mm, 2 mm, 3 mm, 4 mm, 5 mm, 6 mm, 7 mm, 8 mm, 9 mm, or 10 mm wide. The width perpendicular to the upstream to downstream axis of a retainer at its widest section can be less than about: 1 mm, 2 mm, 3 mm, 4 mm, 5 mm, 6 mm, 7 mm, 8 mm, 9 mm, or 10 mm wide.

The width perpendicular to the upstream to downstream axis of a retainer at its narrowest section can be about 1 mm to about 30 mm, about 1 mm to about 25 mm, about 1 mm to about 20 mm, about 1 mm to about 15 mm, about 1 mm to about 10 mm, or about 1 mm to about 5 mm. In some instances, a retainer has a width at its narrowest section that is no more than about: 0.5 mm, 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, or 20 mm wide. In some instances, a retainer has a width at its narrowest section that is more than about: 0.5 mm, 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, or 20 mm wide. The width perpendicular to the upstream to downstream axis of a retainer at its widest section or narrowest section can be about 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, or 20 mm wide.

A retainer can be composed of a variety of polymers, plastics, rubber, silicones, metal, composites, any other materials described herein as suitable for use in the manufacture of a device applicator, or any other material suitable for use as an applicator medical device. A retainer can be made of one material or type of material. Alternatively, a retainer can be composed two or more different materials or types of materials. In some instances, all or a portion of a retainer can be a biocompatible material, or a hypoallergenic material. A retainer can be composed of rigid, substantially rigid, flexible, or substantially flexible materials, or a combination thereof. In some instances, a retainer is comprised of one or more of: COC (cyclic olefin copolymer), silicone, acrylates, polyethylenes, polyurethane, polyurethane, hydrogel, polyester (e.g., DACRONB from E. I. Du Pont de Nemours and Company, Wilmington, Del.), polypropylene, polytetrafluoroethylene (PTFE), expanded PTFE (ePTFE), polyether ether ketone (PEEK), nylon, extruded collagen, polymer foam, rubber, silicone rubber, polyethylene terephthalate, ultra high molecular weight polyethylene, polycarbonate urethane, polyurethane, polyimides, aluminum, stainless steel, nickel-titanium alloy (e.g., Nitinol), titanium, stainless steel, or cobalt-chrome alloy (e.g., ELGILOYB from Elgin Specialty Metals, Elgin, Ill.; CONICHROMEB from Carpenter Metals Corp., Wyomissing, Pa.).

Pump

A device described herein can comprise a pump. A pump can be configured to provide a flow of air or other propellant or a combination thereof through a powdered therapeutic formulation reservoir, out of a nozzle and into a nostril or nasal cavity of a subject. A pump can be configured to provide a flow of air past a poppet valve which regulates the flow of air into a nozzle or reservoir. In some instances, the pump has a smooth inner surface or a smooth outer surface A pump can be composed of a variety of polymers, plastics, rubber, silicones, metal, composites, any other materials described herein as suitable for use in the manufacture of a device applicator, or any other material suitable for use as an applicator pump. A pump can be made of one material or type of material. Alternatively, a pump can be composed two or more different materials or types of materials. In some instances, all or a portion of a pump can be a biocompatible material, or a hypoallergenic material. A pump can be composed of rigid, substantially rigid, flexible, or substantially flexible materials, or a combination thereof. In some instances, a pump is comprised of one or more of silicone, acrylates, polyethylenes, polyurethane, polyurethane, hydrogel, polyester (e.g., DACRONB from E. I. Du Pont de Nemours and Company, Wilmington, Del.), polypropylene, polytetrafluoroethylene (PTFE), expanded PTFE (ePTFE), polyether ether ketone (PEEK), nylon, extruded collagen, polymer foam, rubber, silicone rubber, polyethylene terephthalate, ultra high molecular weight polyethylene, polycarbonate urethane, polyurethane, polyimides, aluminum, stainless steel, nickel-titanium alloy (e.g., Nitinol), titanium, stainless steel, or cobalt-chrome alloy (e.g., ELGILOYB from Elgin Specialty Metals, Elgin, Ill.; CONICHROMEB from Carpenter Metals Corp., Wyomissing, Pa.).

A pump can be one of a variety of pumps suitable for use in a nasal applicator such as, for example, pumps described in U.S. Patent Application Nos. US20090025720, US20090064997, US20080819617, US20080161771, US20080289629, US20080142018, US20070129665, US20060219240, US20060024185, US20060254585, US20040187868, US20040149289, US20040112378, US20020174865; U.S. Pat. Nos. 3,856,185, 4,017,007, 4,200,099, 5,046,493, 5,683,361, 5,702,362, 6,488,648, 6,824,080, 6,866,039, 6,938,798, 6,186,141, 6,345,737, 6,585,172, 6,543,448, 6,089,228, 6,427,680, 6,644,305, 6,494,204, 6,290,667, 7,481,218, international patent applications nos. WO2002/00282, WO2005/000477, WO2008/026730, WO2007/102089, WO1990/07351, and WO/2003/000310, European Patent Nos. EP1673123, and EP1390091, and Japanese Patent and Application Nos. JP2006122189, JP2001095918, JP3678955, JP11226127, JP3488624, JP11221280, JP11197245, JP3547605, JP10028735, JP9248342, JP09028805, JP08322934, JP08280808, JP8206208, JP8103499, and JP8071152, all of which are herein incorporated by reference in their entireties.

A pump can be a pressurized container. In some instances, a pressurized container contains air or other propellant such as one or more of a low molecular weight hydrocarbon such as butane or propane, dimethyl ether, methyl ethyl ether, nitrous oxide, carbon dioxide, nitrogen, a hydrofluorocarbon, compressed air, a chlorofluorocarbon, or a hydrofluoroalkane such as for example, 1,1,2,-tetrafluoroethane or 1,1,1,2,3,3,3-heptafluoropropane. A pressurized container can contain between about 0.1 g of propellant and about 5 g of propellant including at least about: 4 g, 3 g, 2 g, 1.5 g, 1 g, 0.75 g, 0.5 g, 0.25 g, 0.2 g, or 0.1 g of propellant. A pressurized container can be configured to contain a propellant at a maximum pressure of at least about: 1.5 atm, 2 atm, 2.5 atm, 3 atm, 3.5 atm, 4 atm, 4.5 atm, 5 atm, 5.5 atm, 6 atm, 7 atm, 8 atm, 9 atm, 10 atm, 11 atm, or 12 atm. In some instances, a pressurized container can be configured to contain a propellant at a maximum pressure of between about 2 atm and about 10 atm, about 3 atm and about 9 atm, about 4 atm and about 8 atm, about 4 atm and about 7 atm, or between about 4 atm and about 6 atm.

A pressurized container can be activated to release propellant by any means known in the art. For example a pressure valve can engage a pump to release propellant upon the application of a compressive force, or a lever can engage a pump to release propellant upon movement of the lever. In another example, a pressurized container can be activated to release propellant in response to a digital or analog signal. For example, a user can push a button which controls the release of propellant such as by controlling a servo motor or a microprocessor controlled valve. In some instances, a container can be activated by a mechanism that detects nasal inhalation. For example, a lever or other sensing means such as a pressure sensor can be activated by positioning a device as described herein into the nostril of a subject and the inhalation of the subject. A pressurized container can be configured to release a controlled or metered amount of propellant each time a container is activated. In some instances, a pressurized container can continue to release propellant until a user has ceased to provide an activation input.

A pump can be an electric pump or a manual pump. A pump can comprise an inner container slidably disposed within an outer container. Movement of one or more of inner and outer containers by manual or other means can provide a flow of air out of a pump and into a flow passage. Inner and outer containers of a pump can be configured to return to a resting state in the absence of an external compressive force, such as for example through the action of a spring or other return mechanism. In another example, a pump comprises a slidable piston. A piston can be actuated by manual or electric means. Movement of a piston by manual or other means can provide a flow of air out of a pump and into a flow passage. A piston can be configured to return to a resting state in the absence of an external force, such as for example through the action of a spring or other return mechanism.

A pump can comprise a deformable volume. For example, a pump can comprise a plastic, rubber or other deformable material. A pump can also comprise an articulated volume such that accordion-like folds allow compression of a pump to deliver air. A deformable volume can be compressed by for example one or more fingers, (e.g., between a thumb and a forefinger, middle finger, ring finger, little finger) or combination or by one or more hands. Alternatively, a deformable volume can be compressed by electronic or hydraulic means. In some instances, a deformable volume is compressed such as by application of a squeezing or other compressive force and can revert to a non-compressed shape upon release of the compressive force. In some instances, the reversion to a non-compressed shape can be provided by an inherent elastomeric force of the shape and materials of a deformable volume. The reversion can be assisted by a spring or other energy return mechanism.

A pump can be any shape suitable for use in a device described herein, including but not limited to a sphere, an ellipsoid, a cylinder, a cuboid, a frustum, or any other suitable shape such as any of the shapes described herein, or a combination thereof. The upstream to downstream length of a pump can be less than about: 10 cm, 9 cm, 8 cm, 7 cm, 6 cm, 5 cm, 4.5 cm, 4 cm, 3.5 cm, 3 cm, or 2 cm. In some instances, the length of a pump can be between about 2 cm and about 10 cm, between about 2 cm and about 8 cm, between about 2 cm and about 5 mm, between about 4 cm and about 10 cm, or between about 4 cm and about 6 cm. The upstream to downstream length of a pump can be at least about: 1 cm, 2 cm, 3 cm, 4 cm, 5 cm, 6 cm, 7 cm, 8 cm, 9 cm, or 10 cm. The upstream to downstream length of a pump can be about: 1 cm, 2 cm, 3 cm, 4 cm, 5 cm, 6 cm, 7 cm, 8 cm, 9 cm, or 10 cm.

In some instances, the width perpendicular to the upstream to downstream axis of a pump at its widest section is less than about: 1 cm, 1.5 cm, 2 cm, 2.5 cm, 3 cm, 3.5 cm, 4 cm, 4.5 cm, 5 cm, 6 cm, 7 cm, 8 cm, 9 cm, 10 cm, 12 cm, 15 cm, or 20 cm wide. The width perpendicular to the upstream to downstream axis of a pump at its widest section can be at least about: 1 cm, 1.5 cm, 2 cm, 2.5 cm, 3 cm, 3.5 cm, 4 cm, 4.5 cm, 5 cm, 6 cm, 7 cm, 8 cm, 9 cm, 10 cm, 12 cm, 15 cm, or 20 cm wide. The width perpendicular to the upstream to downstream axis of a pump at its widest section can be about: 1 cm, 1.5 cm, 2 cm, 2.5 cm, 3 cm, 3.5 cm, 4 cm, 4.5 cm, 5 cm, 6 cm, 7 cm, 8 cm, 9 cm, 10 cm, 12 cm, 15 cm, or 20 cm wide.

In some instances, a pump has a volume that is less than about: 10 $cm^3$, 9 $cm^3$, 8 $cm^3$, 7 $cm^3$, 6 $cm^3$, 5 $cm^3$, 4 $cm^3$, 3 $cm^3$, 2 $cm^3$, or 1 $cm^3$. In some instances, a pump comprises a volume of about 1 $cm^3$ to about 10 $cm^3$, about 2 $cm^3$ to about 10 $cm^3$, about 2 $cm^3$ to about 7 $cm^3$, or about 4 $cm^3$ to about 8 $cm^3$. A pump can have a volume more than about: 10 $cm^3$, 9 $cm^3$, 8 $cm^3$, 7 $cm^3$, 6 $cm^3$, 5 $cm^3$, 4 $cm^3$, 3 $cm^3$, 2 $cm^3$, or 1 $cm^3$. A pump can have a volume of about: 10 $cm^3$, 9 $cm^3$, 8 $cm^3$, 7 $cm^3$, 6 $cm^3$, 5 $cm^3$, 4 $cm^3$, 3 $cm^3$, 2 $cm^3$, or 1 $cm^3$.

A pump can be configured to deliver between about 1 mL to about 10 mL of air or other propellant to a nostril of a subject during a single activation. A pump can be configured to deliver between about 1 mL to about 10 mL of air or other propellant to a powdered therapeutic reservoir of a device during a single activation. In some instances, a pump is configured to deliver at least about: 1 mL, 2 mL, 3 mL, 4 mL, 5 mL, 6 mL, 7 mL, 8 mL, 9 mL, or 10 mL of air or other propellant to a nostril of a subject or to a reservoir of a device. In some instances, a pump is configured to deliver about: between 1 mL and 10 mL, 1 mL and 8 mL, 1 mL and 5 mL, 2 mL and 10 mL, 2 mL and 8 mL, 2 mL and 7 mL, 2 mL and 6 mL, 2 mL and 5 mL, 3 mL and 10 mL or 3 mL and 8 mL of air or other propellant to a nostril of a subject or to a reservoir of a device. A pump can be configured to deliver less than: 1 mL, 2 mL, 3 mL, 4 mL, 5 mL, 6 mL, 7 mL, 8 mL, 9 mL, or 10 mL of air or other propellant to a nostril of a subject or to a reservoir of a device. A pump can be configured to deliver about: 1 mL, 2 mL, 3 mL, 4 mL, 5 mL, 6 mL, 7 mL, 8 mL, 9 mL, or 10 mL of air or other propellant to a nostril of a subject or to a reservoir of a device. A pump can be configured to be activated by a force of between about 5 kPa and about 100 kPa. A pump can be configured to be activated by a force of less than about: 5 kPa, 6 kPa, 7 kPa, 8 kPa, 9 kPa, 10 kPa, 11 kPa, 12 kPa, 13 kPa, 14 kPa, 15 kPa, 16 kPa, 17 kPa, 18 kPa, 19 kPa, 20 kPa, 21 kPa, 22 kPa, 23 kPa, 24 kPa, 25 kPa, 26 kPa, 28 kPa, 30 kPa, 32 kPa, 33 kPa, 35 kPa, 38 kPa, 40 kPa, 42 kPa, 45 kPa, 48 kPa, or 50 kPa of pressure. A pump can be configured to provide a pressure of air or other propellant at a flow outlet of about 1 kilopascal to about 100 kilopascals, about 2 kilopascals to about 50 kilopascals, about 4 kilopascals to about 40 kilopascals, about 5 kilopascals to about 35 kilopascals, or about 10 to about 30 kilopascals.

Flow Inlet

A pump can comprise a flow inlet for filling of a pump with air or other propellant. In some instances, a flow inlet is in communication with a pump and with an outside environment. A flow inlet can further comprise a poppet valve or other means for regulating the flow of air through a flow inlet. In some instances, a flow inlet can be configured to provide a unidirectional flow of air from the outside of a pump towards the inside of a pump. In some instances, a flow inlet is configured to provide for a movement from a compressed form of a pump provided by application of a compressive force and a non-compressed form of a pump provided by release of the compressive force. For example, application of compressive force by manual squeezing of a pump can provide for movement of air from a pump through a flow outlet and ultimately out of a nozzle, while, releasing of compressive force provides for movement of air into a pump via a flow inlet which in part or in whole provides for a return of a pump to a non-compressed state.

A flow inlet can be any of a number of shapes including but not limited to a cone, a cylinder, tapered cylinder, a frustum, and a parallelepiped or any other shape provided herein, including a combination of one or more of the shapes provided herein. In some instances, the width or diameter of a flow inlet is correlated to the width or diameter of a flow outlet. For example, the width or diameter of a flow inlet can be configured to be less than about: 1%, 2%, 2%, 4%, 5%, 6%, 8%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, or 90% of the width or diameter of a flow outlet. In some case, the size of a flow inlet is correlated to the size of a flow outlet. For example, the size of a flow inlet can be configured to be more than about: 1%, 2%, 2%, 4%, 5%, 6%, 8%, 8%, 9%, 10%, 11%, 12%, 13%, 14%, 15%, 16%, 17%, 18%, 19%, 20%, 21%, 22%, 23%, 24%, 25%, 30%, 35%, 40%, 45%, 50%, 55%, 60%, 65%, 70%, 75%, 80%, or 90% of the size of a flow outlet.

The diameter of a flow inlet can be between about 0.05 and about 2 mm, about 0.05 mm and about 1 mm, about 0.05 and about 0.5 mm, about 0.05 and about 0.1 mm. The diameter of a flow inlet can be about: 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 1, 1.1, 1.2, 1.3, 1.4, 1.5, 1.6, 1.7, 1.8, 1.9, and 2 mm. The diameter of a flow inlet can be more than about: 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 1, 1.1, 1.2, 1.3, 1.4, 1.5, 1.6, 1.7, 1.8, 1.9, and 2 mm. The diameter of a flow inlet can be less than about: 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 1, 1.1, 1.2, 1.3, 1.4, 1.5, 1.6, 1.7, 1.8, 1.9, and 2 mm.

A flow inlet can be on a pump. A flow inlet can be located in the throat of a pump. In some instances, a nozzle hole can also be a flow inlet.

Flow Outlet

A flow outlet can be configured to provide a pressure of from about 1 kilopascal to about 100 kilopascals, about 2 kilopascals to about 50 kilopascals, about 4 kilopascals to about 40 kilopascals or about 5 kilopascals to about 35 kilopascals. A flow outlet can be any of a number of shapes including but not limited to a cone, a cylinder, tapered cylinder, a frustum, and a parallelepiped or any other shape provided herein, including a combination of one or more shapes. In some instances, the upstream to downstream length of a flow outlet is less than about 20 mm, less than about 15 mm, less than about 10 mm, less than about 8 mm, less than about 7 mm, less than about 6 mm, less than about 5 mm, less than about 4 mm, or less than about 3 mm. In some instances, the length of a flow outlet is between about 3 mm and about 20 mm, between about 3 mm and about 15 mm, between about 3 mm and about 10 mm, or between about 5 mm and about 10 mm. A flow outlet can be about: 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 mm in length. In some instances, the width perpendicular to the upstream to downstream axis of a flow outlet at its widest section is between about 5 mm and about 20 mm, or about 5 mm and about 15 mm. In some instances, the width perpendicular to the upstream to downstream axis of a flow outlet at its widest section is at least about: 5 mm, 6 mm, 7 mm, 8 mm, 9 mm, 10 mm, 11 mm, 12 mm, 13 mm, 14 mm, 15 mm, or 20 mm wide. In some instances, the width perpendicular to the upstream to downstream axis of a flow outlet at its narrowest is less than about: 4 mm, 5 mm, 6 mm, 7 mm, 8 mm, 9 mm, 10 mm, 11 mm, 12 mm, 13 mm, 14 mm, 15 mm, or 20 mm wide. The width perpendicular to the upstream to downstream axis of a flow outlet at its widest section can be about: 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, or 30 mm.

Poppet Valve for Airtight Apparatus

In some instances, the poppet valve can be configured to minimize or prevent exposure of the powder formulation to air and moisture, which can result in increased stability of a powder formulation pre-filled in the device or reservoir when the device does not contain an air inlet or when the device is a closed system. The poppet valve can be made by a more simplified manufacturing process of the parts of the device and can result in better cost effectiveness.

The poppet valve can be a poppet valve for the powder formulation and a two way valve for air. The poppet valve can be configured to allow the exit of a powdered therapeutic formulation from the nozzle and allow exit of air from the pump from the nozzle and allow entry of air from the outside environment through the nozzle, which can allow air to enter into the pump. This can allow for repeated activation of the device without the need for a flow inlet in the pump of the device.

In some instances, the device can be an airtight container or a closed system, for example there can be no inlets or holes in the device, for example the pump, when the removable or breakable cover is in place or has not been removed. In some instances the pump does not comprise an air inlet. A device comprising an air inlet in the pump (as described above) can access the outside air. Air can escape from within the device through the air inlet in the pump when the pump is activated in such a device. This loss of air through the air inlet in the pump during activation of the pump can lead to a less than maximal amount of air from within the pump being used to expel the therapeutic formulation from the device. In a device without an air inlet in the pump, there is no air from within the pump lost to the environment through an air inlet. This prevention of air loss in the pump during activation of the pump can lead to the maximal amount of air within the pump being used to expel the therapeutic formulation from the device. In some instances, all air that has been squeezed out of the pump upon activation of the pump in a device lacking an air inlet in the pump can act to propel the therapeutic formulation. This device design (no air inlet in the pump) enables for a reduction in the pump volume and a smaller device compared to a device with an air inlet in the pump. The reduced pump volume size and reduced device size can decrease manufacturing costs and increasing portability of the device lacking an air inlet in the pump compared to a device with an air inlet in the pump.

In some instances, when the removable or breakable cover is in place or has not been removed, there is no communication with a pump and with the outside environment. In some instances, when the removable or breakable cover is removed the device can comprise a flow inlet. In some instances, the flow inlet can comprise the nozzle hole when the removable or breakable cover is removed. The nozzle hole (flow inlet) can be adapted to allow the exit of a powdered therapeutic formulation from the nozzle as a single stream. In some instances, the nozzle has multiple holes (flow inlets) that can emit a powdered therapeutic formulation as multiple streams that remain separate or that can combine into a single stream when the device is activated. In some instances, the nozzle hole is disposed at the downstream end of the nozzle. In some instances, the nozzle hole is also the downstream end of the flow restrictor. A nozzle hole can be any of a number of shapes including but not limited to a circle, oval, triangle, rectangle, or combination thereof.

In some instances, a poppet valve is configured to block movement of powdered therapeutic formulation (e.g., by gravity) in an upstream direction (e.g., into a pump). A poppet valve can be configured so it can be in one position in the device when the device is not activated (e.g., a pump is not activated) and another position in the device when the device is activated (e.g., a pump is activated). A poppet valve can be configured to block movement of a powdered therapeutic formulation (e.g., by gravity) in an upstream direction (e.g., into a flexible vial and/or manual air pump) when the device is not activated (e.g., a manual air pump is not compressed) and when the device is activated (e.g., a manual air pump is compressed).

A poppet valve can be configured to regulate the flow of air from a pump and into a nozzle of a device. A poppet valve can further be configured to regulate the movement of a powdered therapeutic formulation. A poppet valve can be configured to block air or gas flow from a pump into a nozzle when the device is not activated (e.g., a manual air pump is not compressed) and can permit air or gas flow from a pump into a nozzle when the device is activated (e.g., a manual air pump is compressed).

In some instances the poppet valve can be configured to allow movement of air from the outside environment in an upstream direction (e.g., into a flexible vial and/or manual air pump) when the device is being deactivated (e.g., a manual air pump is being decompressed) and in a downstream direction when the device is activated (e.g., a manual air pump is compressed). The decompression of the pump can pull air from the outside environment through the nozzle hole (e.g., flow inlet) and into the nozzle reservoir, through the poppet valve cavity, and into the pump.

In some instances, a nozzle hole (flow inlet) can be configured to provide a bidirectional flow of air from the outside of a pump towards the inside of a pump and from the inside of a pump toward the outside of a pump. In some instances, a nozzle hole or flow inlet is configured to provide for a movement from a compressed form of a pump provided by application of a compressive force and a non-compressed form of a pump provided by release of the compressive force. For example, application of compressive force by manual squeezing of a pump can provide for movement of air from a pump through a flow outlet and ultimately out of a nozzle. Releasing of compressive force can provide for movement of air into a pump via a flow inlet (nozzle hole), through a cavity in the poppet valve, and the flow outlet, which in part or in whole provides for a return of a pump to a non-compressed state. For example, when the compressive force is released, air from the outside environment moves into the pump via the nozzle hole (flow inlet), into the nozzle reservoir, through a cavity spanning internally through the poppet valve, and into the pump.

The poppet valve can contain slits (or channels or grooves) diagonal to a major axis of the device that can create a vortex along the walls of the reservoir when the device is activated.

Inner Inlet Section Length

The length of an inner inlet section can be measured from an upstream end to a downstream end, where upstream and downstream denote the direction of flow of air or other propellant during operation of a device (i.e., air or other propellant can flow from upstream to downstream). The length of an inner inlet section can be the length of a reservoir for a powdered therapeutic formulation. The length of an inner inlet section can be the length of a nozzle pipe. The length of an inner inlet section can be at most about the length from the top (upstream end) of a poppet valve top section to the base (downstream end) of a nozzle hole. The length of the inner inlet section can be at least about the length from the top (upstream end) of a poppet valve top section to a length above the height (upstream end) of a powdered therapeutic formulation when a powdered therapeutic formulation is present in the powdered therapeutic formulation reservoir. The length of the inner inlet section can be at least about the length from the top (upstream) of a poppet valve top section to a length such that the powdered formulation in the reservoir cannot enter into the pump when the pump is activated or deactivated. The length of the inner inlet section can be at least about the length from the top (upstream) of a poppet valve top section to a length such that the powdered formulation in the reservoir cannot enter into or be pulled into the pump when the device is deactivated, or when there is negative pressure in the device.

The upstream to downstream length of an inner inlet section can be less than about 5 cm, less than about 4.5 cm, less than about 4 cm, less than about 3.5 cm, less than about 3 cm, less than about 2.5 cm, less than about 2 cm, less than about 1.5 cm, less than about 1.0 cm, or less than about 0.5 cm. The length of the inner inlet section can be between about 0.5 cm and about 5 cm, between about 1 cm and about 5 cm, between about 1 cm and about 4 cm, between about 1 cm and about 3 cm, between about 2 cm and about 5 cm, or between about 2 cm and about 4 cm, in length. The length of the inner inlet section can be about: 0.5 cm, 1 cm, 1.5 cm, 2 cm, 2.5 cm, 3 cm, 3.5 cm, 4 cm, 4.5 cm, or 5 cm. The length of the inner inlet section can be more than about: 0.5 cm, 1 cm, 1.5 cm, 2 cm, 2.5 cm, 3 cm, 3.5 cm, 4 cm, 4.5 cm, or 5 cm.

External Inner Inlet Section Width

In some instances, the external width perpendicular to the upstream to downstream axis of the inner inlet section at its widest section is about: 0.01 cm to 0.2 cm, 0.01 cm to about 0.15 cm, 0.01 cm to about 0.1 cm, 0.01 cm to about 0.05 cm, 0.02 cm to 0.2 cm, 0.02 cm to about 0.15 cm, 0.02 cm to about 0.1 cm, 0.02 cm to about 0.05 cm, 0.03 cm to 0.2 cm, 0.03 cm to about 0.15 cm, 0.03 cm to about 0.1 cm, 0.03 cm to about 0.05 cm, 0.04 cm to 0.2 cm, 0.04 cm to about 0.15 cm, 0.04 cm to about 0.1 cm, or 0.04 cm to about 0.05 cm. In some instances, the external width perpendicular to the upstream to downstream axis of the inner inlet section at its widest section is no more than about: 0.01 cm, 0.02 cm, 0.03 cm, 0.04 cm, 0.05 cm, 0.06 cm, 0.07 cm, 0.08 cm, 0.09 cm, 0.1 cm, 0.11 cm, 0.12 cm, 0.13 cm, 0.14 cm, 0.15 cm, 0.16 cm, 0.17 cm, 0.18 cm, 0.19 cm, 0.2 cm, 0.3 cm, or 0.4 cm wide. In some instances, the external width perpendicular to the upstream to downstream axis of the inner inlet section at its widest section is about: 0.01 cm, 0.02 cm, 0.03 cm, 0.04 cm, 0.05 cm, 0.06 cm, 0.07 cm, 0.08 cm, 0.09 cm, 0.1 cm, 0.11 cm, 0.12 cm, 0.13 cm, 0.14 cm, 0.15 cm, 0.16 cm, 0.17 cm, 0.18 cm, 0.19 cm, 0.2 cm, 0.3 cm, or 0.4 cm wide. In some instances, the external width perpendicular to the upstream to downstream axis of the inner inlet section at its widest section is more than about: 0.01 cm, 0.02 cm, 0.03 cm, 0.04 cm, 0.05 cm, 0.06 cm, 0.07 cm, 0.08 cm, 0.09 cm, 0.1 cm, 0.11 cm, 0.12 cm, 0.13 cm, 0.14 cm, 0.15 cm, 0.16 cm, 0.17 cm, 0.18 cm, 0.19 cm, 0.2 cm, 0.3 cm, or 0.4 cm wide.

In some instances, the external width perpendicular to the upstream to downstream axis of the inner inlet section at its narrowest section is no more than about: 0.01 cm, 0.02 cm, 0.03 cm, 0.04 cm, 0.05 cm, 0.06 cm, 0.07 cm, 0.08 cm, 0.09 cm, 0.1 cm, 0.11 cm, 0.12 cm, 0.13 cm, 0.14 cm, 0.15 cm, 0.16 cm, 0.17 cm, 0.18 cm, 0.19 cm, 0.2 cm, 0.3 cm, or 0.4 cm. In some instances, the external width perpendicular to the upstream to downstream axis of the inner inlet section at its narrowest section lies within the range of about: 00.01 cm to 0.2 cm, 0.01 cm to about 0.15 cm, 0.01 cm to about 0.1 cm, 0.01 cm to about 0.05 cm, 0.02 cm to 0.2 cm, 0.02 cm to about 0.15 cm, 0.02 cm to about 0.1 cm, 0.02 cm to about 0.05 cm, 0.03 cm to 0.2 cm, 0.03 cm to about 0.15 cm, 0.03 cm to about 0.1 cm, 0.03 cm to about 0.05 cm, 0.04 cm to 0.2 cm, 0.04 cm to about 0.15 cm, 0.04 cm to about 0.1 cm, or 0.04 cm to about 0.05 cm. In some instances, the external width perpendicular to the upstream to downstream axis of the inner inlet section at its narrowest section is about: 0.01 cm, 0.02 cm, 0.03 cm, 0.04 cm, 0.05 cm, 0.06 cm, 0.07 cm, 0.08 cm, 0.09 cm, 0.1 cm, 0.11 cm, 0.12 cm, 0.13 cm, 0.14 cm, 0.15 cm, 0.16 cm, 0.17 cm, 0.18 cm, 0.19 cm, 0.2 cm, 0.3 cm, or 0.4 cm. In some instances, the external width perpendicular to the upstream to downstream axis of the inner inlet section at its narrowest section is more than about: 0.01 cm, 0.02 cm, 0.03 cm, 0.04 cm, 0.05 cm, 0.06 cm, 0.07 cm, 0.08 cm, 0.09 cm, 0.1 cm, 0.11 cm, 0.12 cm, 0.13 cm, 0.14 cm, 0.15 cm, 0.16 cm, 0.17 cm, 0.18 cm, 0.19 cm, 0.2 cm, 0.3 cm, or 0.4 cm.

The width of the inner inlet section can vary continuously, can vary in a step-wise fashion, does not vary, or a combination thereof. The inner width or the outer width of the inner inlet section can vary continuously, can vary in a step-wise fashion, does not vary, or a combination thereof. The upstream and downstream ends of the inner inlet section can be the same width or different. In some instances, the widest and narrowest sections of an inner inlet section are at the ends (i.e., the top (upstream) of the poppet valve top section and the upstream opening of the poppet valve cavity). For example, the widest section of an inner inlet section can be at the upstream end and the narrowest section of the inner inlet section can be at the downstream end, or vice versa. In some instances, the widest and/or narrowest sections of an inner inlet section are not at the end. In some instances, the widest section of an inner inlet section is an inner inlet section base for attachment to a poppet valve top section.

Internal Inner Inlet Section Width

In some instances, the internal width perpendicular to the upstream to downstream axis of the inner inlet section at its widest section is about: between about 0.001 cm to 0.2 cm, 0.001 cm to about 0.15 cm, 0.001 cm to about 0.1 cm, 0.001 cm to about 0.06 cm, 0.001 cm to about 0.05 cm, 0.005 cm to 0.2 cm, 0.005 cm to about 0.15 cm, 0.005 cm to about 0.1 cm, 0.005 cm to about 0.06 cm, 0.005 cm to about 0.05 cm, 0.01 cm to 0.2 cm, 0.01 cm to about 0.15 cm, 0.01 cm to about 0.1 cm, 0.01 cm to about 0.06 cm, 0.01 cm to about 0.05 cm, 0.015 cm to 0.2 cm, 0.015 cm to about 0.15 cm, 0.015 cm to about 0.1 cm, 0.015 cm to about 0.06 cm, 0.015 cm to about 0.05 cm, 0.02 cm to 0.2 cm, 0.02 cm to about 0.15 cm, 0.02 cm to about 0.1 cm, 0.02 cm to about 0.06 cm, or 0.02 cm to about 0.05 cm. In some instances, the internal width perpendicular to the upstream to downstream axis of the inner inlet section at its widest section is no more than about: 0.001 cm, 0.002 cm, 0.003 cm, 0.004 cm, 0.005 cm, 0.006 cm, 0.007 cm, 0.008 cm, 0.009 cm, 0.01 cm, 0.015 cm, 0.02 cm, 0.025 cm, 0.03 cm, 0.035 cm, 0.04 cm, 0.045 cm, 0.05 cm, 0.055 cm, 0.06 cm, 0.065 cm, 0.07 cm, 0.075 cm, 0.08 cm, 0.085 cm, 0.09 cm, 0.095 cm, 0.1 cm, 0.11 cm, 0.12 cm, 0.13 cm, 0.14 cm, 0.15 cm, 0.16 cm, 0.17 cm, 0.18 cm, 0.19 cm, or 0.2 cm wide. In some instances, the internal width perpendicular to the upstream to downstream axis of the inner inlet section at its widest section is more than about: 0.001 cm, 0.002 cm, 0.003 cm, 0.004 cm, 0.005 cm, 0.006 cm, 0.007 cm, 0.008 cm, 0.009 cm, 0.01 cm, 0.015 cm, 0.02 cm, 0.025 cm, 0.03 cm, 0.035 cm, 0.04 cm, 0.045 cm, 0.05 cm, 0.055 cm, 0.06 cm, 0.065 cm, 0.07 cm, 0.075 cm, 0.08 cm, 0.085 cm, 0.09 cm, 0.095 cm, 0.1 cm, 0.11 cm, 0.12 cm, 0.13 cm, 0.14 cm, 0.15 cm, 0.16 cm, 0.17 cm, 0.18 cm, 0.19 cm, or 0.2 cm wide. In some instances, the internal width perpendicular to the upstream to downstream axis of the inner inlet section at its widest section is about: 0.001 cm, 0.002 cm, 0.003 cm, 0.004 cm, 0.005 cm, 0.006 cm, 0.007 cm, 0.008 cm, 0.009 cm, 0.01 cm, 0.015 cm, 0.02 cm, 0.025 cm, 0.03 cm, 0.035 cm, 0.04 cm, 0.045 cm, 0.05 cm, 0.055 cm, 0.06 cm, 0.065 cm, 0.07 cm, 0.075 cm, 0.08 cm, 0.085 cm, 0.09 cm, 0.095 cm, 0.1 cm, 0.11 cm, 0.12 cm, 0.13 cm, 0.14 cm, 0.15 cm, 0.16 cm, 0.17 cm, 0.18 cm, 0.19 cm, or 0.2 cm wide.

In some instances, the internal width perpendicular to the upstream to downstream axis of the inner inlet section at its narrowest section is no more than about: 0.001 cm, 0.002 cm, 0.003 cm, 0.004 cm, 0.005 cm, 0.006 cm, 0.007 cm, 0.008 cm, 0.009 cm, 0.01 cm, 0.015 cm, 0.02 cm, 0.025 cm, 0.03 cm, 0.035 cm, 0.04 cm, 0.045 cm, 0.05 cm, 0.055 cm, 0.06 cm, 0.065 cm, 0.07 cm, 0.075 cm, 0.08 cm, 0.085 cm, 0.09 cm, 0.095 cm, 0.1 cm, 0.11 cm, 0.12 cm, 0.13 cm, 0.14 cm, 0.15 cm, 0.16 cm, 0.17 cm, 0.18 cm, 0.19 cm, or 0.2 cm wide. In some instances, the internal width perpendicular to the upstream to downstream axis of the inner inlet section at its narrowest section is more than about: 0.001 cm, 0.002 cm, 0.003 cm, 0.004 cm, 0.005 cm, 0.006 cm, 0.007 cm, 0.008 cm, 0.009 cm, 0.01 cm, 0.015 cm, 0.02 cm, 0.025 cm, 0.03 cm, 0.035 cm, 0.04 cm, 0.045 cm, 0.05 cm, 0.055 cm, 0.06 cm, 0.065 cm, 0.07 cm, 0.075 cm, 0.08 cm, 0.085 cm, 0.09 cm, 0.095 cm, 0.1 cm, 0.11 cm, 0.12 cm, 0.13 cm, 0.14 cm, 0.15 cm, 0.16 cm, 0.17 cm, 0.18 cm, 0.19 cm, or 0.2 cm wide. In some instances, the internal width perpendicular to the upstream to downstream axis of the inner inlet section at its narrowest section lies within the range of about: 0.001 cm to 0.2 cm, 0.001 cm to about 0.15 cm, 0.001 cm to about 0.1 cm, 0.001 cm to about 0.06 cm, 0.001 cm to about 0.05 cm, 0.005 cm to 0.2 cm, 0.005 cm to about 0.15 cm, 0.005 cm to about 0.1 cm, 0.005 cm to about 0.06 cm, 0.005 cm to about 0.05 cm, 0.01 cm to 0.2 cm, 0.01 cm to about 0.15 cm, 0.01 cm to about 0.1 cm, 0.01 cm to about 0.06 cm, 0.01 cm to about 0.05 cm, 0.015 cm to 0.2 cm, 0.015 cm to about 0.15 cm, 0.015 cm to about 0.1 cm, 0.015 cm to about 0.06 cm, 0.015 cm to about 0.05 cm, 0.02 cm to 0.2 cm, 0.02 cm to about 0.15 cm, 0.02 cm to about 0.1 cm, 0.02 cm to about 0.06 cm, or 0.02 cm to about 0.05 cm. In some instances, the internal width perpendicular to the upstream to downstream axis of the inner inlet section at its narrowest section is about: 0.001 cm, 0.002 cm, 0.003 cm, 0.004 cm, 0.005 cm, 0.006 cm, 0.007 cm, 0.008 cm, 0.009 cm, 0.01 cm, 0.015 cm, 0.02 cm, 0.025 cm, 0.03 cm, 0.035 cm, 0.04 cm, 0.045 cm, 0.05 cm, 0.055 cm, 0.06 cm, 0.065 cm, 0.07 cm, 0.075 cm, 0.08 cm, 0.085 cm, 0.09 cm, 0.095 cm, 0.1 cm, 0.11 cm, 0.12 cm, 0.13 cm, 0.14 cm, 0.15 cm, 0.16 cm, 0.17 cm, 0.18 cm, 0.19 cm, or 0.2 cm wide.

Internal Volume of Inner Inlet Section

The inner inlet section can be hollow and can contain an internal volume. The internal volume of an inner inlet section can be about: 0.0001 $cm^3$ or more, 0.0005 $cm^3$ or more, 0.001 $cm^3$ or more, 0.005 $cm^3$ or more, 0.01 $cm^3$ or more, 0.02 $cm^3$ or more, or 0.03 $cm^3$ or more. In some instances, the internal volume of an inner inlet section is between about: 0.0001 $cm^3$ and about 0.03 $cm^3$, between about 0.0001 $cm^3$ and about 0.02 $cm^3$, between about 0.0001 $cm^3$ and about 0.01 $cm^3$, between about 0.0001 $cm^3$ and about 0.005 $cm^3$, between about 0.0001 $cm^3$ and about 0.001 $cm^3$, between about 0.0001 $cm^3$ and about 0.0005 $cm^3$, between about 0.0005 $cm^3$ and about 0.03 $cm^3$, between about 0.0005 $cm^3$ and about 0.02 $cm^3$, between about 0.0005 $cm^3$ and about 0.01 $cm^3$, between about 0.0005 $cm^3$ and about 0.005 $cm^3$, between about 0.0005 $cm^3$ and about 0.001 $cm^3$, between about 0.001 $cm^3$ and about 0.03 $cm^3$, between about 0.001 $cm^3$ and about 0.02 $cm^3$, between about 0.001 $cm^3$ and about 0.01 $cm^3$, between about 0.001 $cm^3$ and about 0.005 $cm^3$, between about 0.005 $cm^3$ and about 0.03 $cm^3$, between about 0.005 $cm^3$ and about 0.02 $cm^3$, between about 0.005 $cm^3$ and about 0.01 $cm^3$, between about 0.01 $cm^3$ and about 0.03 $cm^3$, or between about 0.01 $cm^3$ and about 0.02 $cm^3$. The internal volume of the inner inlet section can be about: 0.0001 $cm^3$, 0.0002 $cm^3$, 0.0003 $cm^3$, 0.0004 $cm^3$, 0.0005 $cm^3$, 0.0006 $cm^3$, 0.0007 $cm^3$, 0.0008 $cm^3$, 0.0009 $cm^3$, 0.001 $cm^3$, 0.002 $cm^3$, 0.003 $cm^3$, 0.004 $cm^3$, 0.005 $cm^3$, 0.006 $cm^3$, 0.007 $cm^3$, 0.008 $cm^3$, 0.009 $cm^3$, 0.011 $cm^3$, 0.012 $cm^3$, 0.013 $cm^3$, 0.014 $cm^3$, 0.015 $cm^3$, 0.016 $cm^3$, 0.017 $cm^3$, 0.018 $cm^3$, 0.019 $cm^3$, 0.02 $cm^3$, 0.021 $cm^3$, 0.022 $cm^3$, 0.023 $cm^3$, 0.024 $cm^3$, 0.025 $cm^3$, 0.026 $cm^3$, 0.027 $cm^3$, 0.028 $cm^3$, 0.029 $cm^3$, 0.03 $cm^3$, 0.04 $cm^3$, 0.05 $cm^3$, 0.06 $cm^3$, 0.07 $cm^3$, 0.08 $cm^3$, 0.09 $cm^3$, or 1.0 $cm^3$. The internal volume of the inner inlet section can be more than about: 0.0001 $cm^3$, 0.0005 $cm^3$, 0.001 $cm^3$, 0.005 $cm^3$, 0.01 $cm^3$, 0.02 $cm^3$, or 0.03 $cm^3$. The internal volume of the inner inlet section can be less than about: 0.0001 $cm^3$, 0.0005 $cm^3$, 0.001 $cm^3$, 0.005 $cm^3$, 0.01 $cm^3$, 0.02 $cm^3$, or 0.03 $cm^3$.

Throat Ring

A flow outlet of a pump can be located in the throat of the pump (e.g., manual air pump and/or vial). A manual air pump or vial can contain a throat ring in a throat of the manual air pump of vial. A throat ring can be fused to the throat of a manual air pump or vial. A throat ring can be inserted into the throat of a manual air pump or vial. A throat ring can be configured to restrict the width of the throat of a manual air pump or vial. An opening in a throat ring can be of a width narrower than the widest width of a poppet valve.

The width of a hole formed by a throat ring can be about: 1 to 20 mm, 1 to 10 mm, 1 to 7.5 mm, or 1 to 5 mm. The width of a hole formed by a throat ring can be about: 1, 2, 3, 4, 5, 6, 7, 8, 9, 10, 11, 12, 13, 14, 15, 16, 17, 18, 19, or 20 mm. The width of a hole formed by a throat ring can be more than about: 1, 2, 3, 4, 5, 6, 7, 8, 9, 10, 11, 12, 13, 14, 15, 16, 17, 18, 19, or 20 mm. The width of a hole formed by a throat ring can be less than about: 1, 2, 3, 4, 5, 6, 7, 8, 9, 10, 11, 12, 13, 14, 15, 16, 17, 18, 19, or 20 mm.

The diameter of a throat ring can be about: 1 to 20 mm, 1 to 17.5 mm, 1 to 15 mm, 1 to 12.5 mm, 1 to 10 mm, 1 to 7.5 mm, or 1 to 5 mm. The diameter of a throat ring can be about: 1, 2, 3, 4, 5, 6, 7, 8, 9, 10, 11, 12, 13, 14, 15, 16, 17, 18, 19, or 20 mm. The diameter of a throat ring can be more than about: 1, 2, 3, 4, 5, 6, 7, 8, 9, 10, 11, 12, 13, 14, 15, 16, 17, 18, 19, or 20 mm. The diameter of a throat ring can be less than about: 1, 2, 3, 4, 5, 6, 7, 8, 9, 10, 11, 12, 13, 14, 15, 16, 17, 18, 19, or 20 mm.

The height of a throat ring can be about: 1 to 20 mm, 1 to 17.5 mm, 1 to 15 mm, 1 to 12.5 mm, 1 to 10 mm, 1 to 7.5 mm, or 1 to 5 mm. The height of a throat ring can be about: 1, 2, 3, 4, 5, 6, 7, 8, 9, 10, 11, 12, 13, 14, 15, 16, 17, 18, 19, or 20 mm. The height of a throat ring can be more than about: 1, 2, 3, 4, 5, 6, 7, 8, 9, 10, 11, 12, 13, 14, 15, 16, 17, 18, 19, or 20 mm. The height of a throat ring can be less than about: 1, 2, 3, 4, 5, 6, 7, 8, 9, 10, 11, 12, 13, 14, 15, 16, 17, 18, 19, or 20 mm. The height of a throat ring can be the same or different as the height of a throat of a manual air pump or vial.

A throat ring thickness (distance inner to outer edge of a throat ring) can be about: 0.1 to 20 mm, 0.1 to 15 mm, 0.1 to 10 mm, 0.1 to 7.5 mm, 0.1 to 5 mm, or 0.1 to 2.5 mm. A throat ring thickness (distance from inner to outer edge of a throat ring) can be about: 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5 5.6, 5.7, 5.8, 5.9, 6, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, or 10 mm. A throat ring thickness (distance from inner to outer edge of a throat ring) can be more than about: 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5 5.6, 5.7, 5.8, 5.9, 6, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, or 10 mm. A throat ring thickness (distance from inner to outer edge of a throat ring) can be less than about: 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5 5.6, 5.7, 5.8, 5.9, 6, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, or 10 mm.

A throat ring can be composed of a variety of polymers, plastics, rubber, silicones, metal, composites, any other materials described herein as suitable for use in the manufacture of an intranasal delivery device, or any other material suitable for use in an intranasal delivery device. A throat ring can be made of one material or type of material. Alternatively, a throat ring can be composed two or more different materials or types of materials. All or a portion of a throat ring can be a biocompatible material or a hypoallergenic material. A throat ring can be composed of rigid, substantially rigid, flexible, or substantially flexible materials, or a combination thereof. In some instances, a throat ring can be comprised of one or more of paper, silicone, acrylates, polyethylenes, polyurethane, polyurethane, hydrogel, polyester (e.g., DACRONB from E. I. Du Pont de Nemours and Company, Wilmington, Del.), polypropylene, polytetrafluoroethylene (PTFE), expanded PTFE (ePTFE), polyether ether ketone (PEEK), nylon, extruded collagen, polymer foam, rubber, silicone rubber, polyethylene terephthalate, ultra high molecular weight polyethylene, polycarbonate urethane, polyurethane, polyimides, aluminum, stainless steel, nickel-titanium alloy (e.g., Nitinol), titanium, stainless steel, or cobalt-chrome alloy (e.g., ELGILOYB from Elgin Specialty Metals, Elgin, Ill.; CONICHROMEB from Carpenter Metals Corp., Wyomissing, Pa.).

The devices disclosed herein can be utilized for the delivery of any formulation which can be delivered intranasally. For example, the devices can be used for delivering dry powder formulations of a pharmaceutical, a neutraceutical or other suitable compound.

Methods of Use

Provided herein are methods for delivering a powdered therapeutic formulation to a subject with an intranasal delivery device described herein. A drug can be loaded to a nozzle, and the nozzle with the drug can be attached to a pump. If the intranasal delivery device contains a cover, for example, a removable or breakable cover or a cap, the cover can be removed from the intranasal delivery device. The removal can be by breaking, lifting, twisting, pressing, or turning the cover. When the device is not activated, a poppet valve can rest on the surface of a vial throat to prevent the powdered therapeutic from moving upstream into a pump (e.g., a flexible vial). The nozzle can be inserted or partially inserted in a nostril of a subject. The user can insert the device or another person (e.g., a health care provider) can insert the device in a nostril of the subject. A device can be activated (e.g., by compressing a pump that is a flexible vial, by activating a pressurized pump). Air can flow out a flow outlet of a pump and cause the poppet valve to rise in the nozzle of the device. When the poppet valve rises in the nozzle it may no longer be resting on the vial throat. The non-slit portions of a poppet valve can contact the nozzle pipe to prevent a powdered therapeutic formulation from moving upstream into the pump. Air can travel around parts of the poppet valve and flow over grooves in the poppet valve. The air can then flow into a reservoir and force the powdered therapeutic formulation up a nozzle pipe, out a nozzle hole, and into the nostril of the subject.

Assembly

A powdered therapeutic formulation can be loaded into a nozzle. The nozzle can have a cap, removable or breakaway cover, etc. A nozzle can then be coupled to a pump. The nozzle can be coupled to the pump by, for example, screwing the nozzle to the pump, clipping the nozzle to the pump, snapping the nozzle to the pump, etc.

II. Formulations

A device described herein is suitable for delivering active agents including, but not limited to, free-base and salt forms of the agents. An active agent can be in crystalline or amorphous forms. A powdery therapeutic formulation can consist of just the therapeutic agent "carrier free" or they can further comprise a suitable carrier, filler, diluent, excipient, permeation enhancers, solubilizers and adjuvants or other material.

A device described herein can protect the powdered therapeutic formulation from moisture or air until a device is prepared for use. A device can be prepared for use by removing or breaking off of a protective cover. Anhydrous formulations can be provided in a reservoir and a device can further be packaged using materials known to prevent exposure to humidity or water such that they can be included in suitable formulary kits. Examples of suitable packaging include, but are not limited to, hermetically sealed foils, plastic or the like, unit dose containers, blister packs, and strip packs.

Active Agents

In some cases, an active agent disclosed herein is a non-peptide/non-protein drug. In some instances, the active agent is selected from the group consisting of ergot alkaloid, serotonin (5-HT)-1B, -1D or -1F receptor agonist, 5-hydroxytryptaminel (5-HT1) receptor agonist, CGRP antagonist, NK-1 receptor antagonist, antihistamine, antiemetic agent, decongestant, opioid receptor agonist, antibiotic, antifungal agent, sulfa drug, antituberculosis drug, antimicrobial agent, antiviral agent, hypnotic sedative, antiepileptic agent, narcotic analgesic, nonnarcotic analgesic, sedative drug, psychotherapeutic agent, muscle relaxant, antiallergic agent, anti-rheumatic drug, cardiotonic drug, antiarrhythmic agent, antihypertensive agent, diuretic agent, coronary vasodilator, antidementia drug, brain activator, brain circulation ameliorating agent, antiparkinsonian agent, antihyperlipidemic drug, antiulcer drug, obesity drug, diabetic drug, hemostatic drug, antithrombotic agent, migraine drug, antitussive drug, expectorant, respiratory stimulant, asthma drug, antidiarrheal drug, nonsteroidal antiinflammatory agent, antipodagric, therapeutic agent for urinary disease, drug for improving sexual function, agent for the uterus, steroid, prostaglandin, vitamin, antidote, therapeutic agent for heavy metal toxification, quit smoking agent, antianaphylactic agent, antitumor agent, immunostimulator, immunosuppressive drug, and any combination thereof. In some instances, the active agent is selected from the group consisting of didanosine, zidovudine, lamivudine, acyatazanavir, nelfenavir, sanilvudine, emtricitabine, polyinosinic-polycytidylic acid, oseltamivir, zanamivir, valganciclovir, peramivir, laninamivir, favipiravir, amantadine, amphotericin B, miconazole, fluconazole, itraconazole, ketoconazole, ketamine, pentobarbital sodium, thiopental, amopentobarbital, hexobarbital, lidocaine, triazolam, zopiclone, zolpidem, eszopiclone, etizolam, clotiazepam, brotizolam, lormetazepam, estazolam, midazolam, nitrazepam, flunitrazepam, diazepam, chlordiazepoxide HCl, alprazolam, lorazepam, ethyl loflazepate, bromazepam, rilmazafone, chloral hydrate, carbamazepine, clonazepam, zonisamide, sodium valproate, phenytoin, phenobarbital, primidone, gabapentin, opium, morphine, ethylmorphine, oxycodone, hydrocodone, codeine, dihydrocodeine, fentanyl, remifentanil, droperidol, levorphanol, methadone, meperidine, pethidine, buprenorphine, butorphanol, tramadol, tapentadol, nalfurafine, pentazocine, nalbuphine hydrochloride, nalorphine, eptazocine, levallorphan, sulpyrine, aspirin, acetaminophen, ergotamine, dihydroergotamine, sumatriptan, eletriptan, zolmitriptan, rizatriptan, naratriptan, almotriptan, frovatriptan, avitriptan, lasmiditan, olcegepant, telcagepant, donepezil, suxamethonium, pancuronium, sildenafil, vardenafil, apomorphine, tadalafil, atropine, scopolamine, homatropine methylbromide, chlorpromazine, digitoxin, levomepromazine, thioridazine, acepromazine, digoxin, methyldigoxin, isosorbide, nitroglycerin, quinidine, disopyramide, dopamine, dobutamine, epinephrine, etilefrine, norepinephrine, phenylephrine, dimorpholamine, doxapram, naloxone, flumazenil, tipepidine, dextromethorphan, ambroxol, bromhexine, salbutamol, terbutaline, procaterol, theophylline, ephedrine, sodium cromoglycate, ketotifen, oxatomide, tranilast, granisetron, azasetron, ramosetron, tropisetron, indisetron, palonosetron, cisapride, domperidone, metoclopramide, trimebutine, loperamide, mefenamic acid, indomethacin, sulindac, ibuprofen, ketoprofen, naproxen, pranoprofen, loxoprofen, diclofenac, tiaprofenic acid, tiaramide, carbazochrome sulfonic acid, tranexamic acid, pralidoxime iodide methyl, progesterone, testosterone, dehydroepiandrosterone, estrogen, estradiol, levonorgestrel, protamine, leucovorin, dimercaprol, deferoxamine, sodium thiosulfate, mifepristone, risperidone, olanzapine, thalidomide, civamide, acyclovir, valacyclovir, famciclovir, penciclovir, lopinavir, ritonavir, saquinavir, vidarabine, idoxuridine, nifedipine, nimodipine, amiodarone, loratadine, tretinoin, carmustin, beraprost sodium, and any combination thereof.

In some instances, the active agent is a small molecule drug, e.g., having a molecular weight of less than about 1000 grams/mole (g/mol), about 750 g/mol, or about 500 g/mol. In some instances, the active agent is an anti-migraine drug. In some instances, the active agent is an ergot alkaloid. In some instances, the active agent is dihydroergotamine (DHE) or a pharmaceutically acceptable salt thereof, e.g., DHE mesylate. In some instances, the active agent is indomethacin, midazolam, or phenobarbital. In some instances, the active agent is indomethacin or a pharmaceutically acceptable salt thereof. In some instances, the active agent is testosterone or a pharmaceutically acceptable salt thereof.

In some cases, an active agent disclosed herein is a peptide or a peptide-related compound, wherein the peptide or peptide-related compound has a molecular weight of about 10,000 Daltons (Da) or less, about 20,000 (Da) or less, about 30,000 (Da) or less, about 40,000 (Da) or less, or about 50,000 Daltons or less. In some instances, the active agent is selected from the group consisting of insulin, human growth hormone, calcitonin, glucagon, parathyroid hormone, parathyroid hormone (1-34), glucagon-like peptide-1, interferon, interleukin, erythropoietin, luteinizing hormone-releasing hormone, somatostatin, vasopressin, oxytocin, enkephalin, adrenocorticotropic hormone, growth hormone-releasing hormone, granulocyte colony formation-stimulating factor, parathyroid hormone, thyroid-stimulating hormone-releasing hormone, angiotensin, prolactin, luteinizing hormone, gastric inhibitory polypeptide (GIP), C-peptide, cyclosporine, FK-506, octreotide, carperitide, pramlintide, lanreotide, eptifibatide, albiglutide, pasireotide, teriparatide, exenatide, liraglutide, emfuvirtide, ziconotide, ecallantide, mifamurtide, nesiritide, peglinesatide, afamelanotide, linaclotide, lixisenatide, teduglutide, bentiromide, cureletide diethylamine, degarelix, ghrelin, atrial natriuretic peptide, a peptide analog thereof, and any combination thereof.

Methods and formulations presented herein can utilize an active agent in a freebase, salt, hydrate, polymorph, isomer, diastereomer, prodrug, metabolite, ion pair complex, or chelate form. An active agent can be formed using a pharmaceutically acceptable non-toxic acid or base, including an inorganic acid or base, or an organic acid or base. In some instances, an active agent that can be utilized in connection with the methods and formulations presented herein is a pharmaceutically acceptable salt derived from acids including, but not limited to, the following: acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, or p-toluenesulfonic acid. In some instances, the active agent is a salt of methanesulfonic acid. An alternative nomenclature of the methanesulfonic acid salt of DHE is DHE mesylate. For further description of pharmaceutically acceptable salts that can be used in the methods described herein see, for example, S. M. Barge et al., "Pharmaceutical Salts," 1977, J. Pharm. Sci. 66:1-19, which is incorporated herein by reference in its entirety.

In some cases, an average particle size of an active agent or a formulation disclosed herein can be less than about 100 micrometer (μm), for example, about: 95 μm, 90 μm, 85 μm, 80 μm, 75 μm, 70 μm, 65 μm, 60 μm, 55 μm, 50 μm, 45 μm, 40 μm, 35 μm, 30 μm, 25 μm, 20 μm, 15 μm, 10 μm, 5 μm or less. In some instances, an average particle size of an active agent or a formulation disclosed herein can be larger than 10 μm, for example, more than about: 250 μm, 200 μm, 190 μm, 180 μm, 170 μm, 160 μm, 150 μm, 140 μm, 130 μm, 120 μm, 110 μm, 100 μm, 95 μm, 90 μm, 85 μm, 80 μm, 75 μm, 70 μm, 65 μm, 60 μm, 55 μm, 50 μm, 45 μm, 40 μm, 35 μm, 30 μm, 25 μm, 20 μm, or 15 μm. The particle size of an active agent or a powder formulation can be about: 20-100 microns, 25-150 microns, 25-175 microns, 25-200 microns, 25-250 microns, 25-300 microns, 50-150 microns, 50-175 microns, 50-200 microns, 50-250 microns, 50-300 microns, 10-100 μm, for example, about: 15-90 μm, 15-80 μm, 15-70 μm, 15-60 μm, 15-50 μm, 15-40 μm, 15-30 μm, 15-20 μm, 15-20 μm, 10-90 μm, 10-80 μm, 10-70 μm, 10-60 μm, 10-50 μm, 10-40 μm, 10-30 μm, 10-20 μm, 20-90 μm, 20-80 μm, 20-70 μm, 20-60 μm, 20-50 μm, 20-40 μm, 20-30 μm, 30-90 μm, 30-80 μm, 30-70 μm, 30-60 μm, 30-50 μm, 30-40 μm, 40-90 μm, 40-80 μm, 40-70 μm, 40-60 μm, 40-50 μm, 50-90 μm, 50-80 μm, 50-70 μm, 50-60 μm, 60-90 μm, 60-80 μm, 60-70 μm, 70-90 μm, 70-80 μm, or 80-90 μm. The average particle size of the active agent or the formulation can be about: 5.0 μm, 5.5 μm, 6.0 μm, 6.5 μm, 7.0 μm, 7.5 μm, 8.0 μm, 8.5 μm, 9.0 μm, 9.5 μm, 10 μm, 11 μm, 12 μm, 13 μm, 14 μm, 15 μm, 16 μm, 17 μm, 18 μm, 19 μm, 20 μm, 25 μm, 30 μm, 35 μm, 40 μm, 45 μm, 50 μm, 55 μm, 60 μm, 65 μm, 70 μm, 75 μm, 80 μm, 85 μm, 90 μm, 95 μm, or 100 μm. In some instances, not less than 90% of the powder formulations presented herein have a particle diameter less than 150 μm, and not more than 5% of the particles have a diameter less than 5 μm. In some instances, the overall average particle size of the powder formulations presented herein are about 15 μm to about 30 μm, about 18 μm to about 25 μm, about 18 μm to about 20 μm, or 20 μm.

In some cases, a total weight of a powder formulation comprises about 0.4% to about 46%, or about 0.4% to about 23% or about 0.4% to about 9%, or about 2% to about 9%, or about 4% to about 9% of an active agent. In some instances, the total weight of the powder formulation comprises about 0.3% to about 37%, or about 0.3% to about 18% or about 0.3% to about 7%, or about 2% to about 7%, or about 3% to about 9% of an active agent or a pharmaceutically acceptable salt thereof.

In some cases, a formulation disclosed herein further comprises an additional active agent, for example: an adenosine receptor antagonist, a phosphodiesterase inhibitor, an acetylcholinesterase inhibitor, a vasodilator, xanthine, caffeine, paraxanthine, theobromine, and theophylline. For example, the methods and formulations further comprise caffeine. The additional active agent (e.g., caffeine) can be at least about 1% of the total weight of the powder formulation, for example about: 1%, 2%, 3%, 4%, 5%, 6%, 7%, 8%, 9%, 10%, 15%, 20%, 25%, 30%, 35%, 40%, 45%, 50%, 55%, 60% or more of the total weight of the powder formulation. The additional active agent (e.g., caffeine) can be about 1% to 60% of the total weight of the powder formulation, for example, about: 1%-60%, 1%-50%, 1%-40%, 1%-30%, 1%-20%, 1%-10%, 1%-5%, 10%-60%, 10%-50%, 10%-40%, 10%-30%, 10%-20%, 20%-60%, 20%-50%, 20%-40%, 20%-30%, 30%-60%, 30%-50%, 30%-40%, 40%-60%, 40%-50%, or 50%-60% of the total weight of the powder formulation. In some instances, the powder formulation comprises about 5% to 10% of an additional active agent (e.g., caffeine). In some instances, the caffeine is anhydrous caffeine. In some instances, the powder formulation comprises about 10% to 15% of an additional active agent (e.g., caffeine).

In some cases, the present disclosure provides for a device containing a powdered therapeutic formulation comprising particles that comprise an active agent and at least one member selected from the group consisting of a thickening agent, a carrier, a pH adjusting agent, a sugar alcohol, and any combination thereof, wherein: at least about 10%, about 20%, about 30%, about 40%, or about 50% by weight of the active agent in the particles is amorphous as determined by X-ray diffraction; when the active agent has a crystalline form, a solubility of the active agent in a crystalline form in an aqueous liquid ranges from about 0.1 μg/mL to about 1 milligram/milliliter (mg/mL) in water at a temperature of 37±0.5° C.; the particles have an average particle size of about 10 microns to about 300 microns, as measured by laser diffraction; and when the powdered therapeutic formulation is administered, a pharmacokinetic parameter of the active agent improves by at least about 15%, compared to a corresponding formulation that comprises the active agent in a crystalline form when administered. In some instances, the powdered therapeutic formulation further comprises particles that comprise the active agent and are free from the thickening agent, the carrier, the pH adjuster, the sugar alcohol, or a combination thereof. In some instances, the active agent is a non-peptide/non-protein drug. In some instances, the particles have an average particle size of from about 15 to about 100 μm, as measured by laser diffraction. In some instances, the particles have an average particle size of from about 20 to about 50 μm, as measured by laser diffraction. In some instances, the particles are spray dried. In some instances, the active agent is spray dried onto the carrier, the thickening agent, the pH adjuster, the sugar alcohol or a combination thereof to form the particles. In some instances, the solubility is measured at a pH of about 6.0, 6.1, 6.2, 6.3, 6.4, 6.5, 6.6, 6.7, 6.8, 6.9, 7.0, 7.1, 7.2, 7.3, 7.4, 7.5, 7.8, 7.9, 7.10, for example, ranging from about 6.8 to about 7.4. In some instances, the particles comprise the carrier that is at least partially water insoluble at 37±0.5° C. In some instances, the water insolubility is measured at a pH ranging from about 6.8 to about 7.4. In some instances, the particles further comprise the thickening agent, and wherein the carrier has lower water solubility than that of the thickening agent. In some instances, the particles comprise the carrier that is at least partially adhesive to mucus. In some instances, the particles comprise the carrier that comprises an oligosaccharide, a polysaccharide, or any combination thereof. In some instances, the carrier comprises microcrystalline cellulose, ethyl cellulose, cellulose acetate, cellulose acetate butyrate, cellulose acetate propionate, cellulose acetate phthalate, hydroxypropylmethylcellulose phthalate, starch, chitosan, β cyclodextrin, or any combination thereof. In some instances, the particles comprise the carrier that has an average particle size of from about 10 to about 100 μm, as measured by laser diffraction. In some instances, the carrier has an average particle size of about 20 μm, as measured by laser diffraction. In some instances, the particles comprise the thickening agent that is at least partially water soluble at 37±0.5° C. In some instances, the water solubility is measured at a pH ranging from about 6.8 to about 7.4. In some instances, the particles further comprise the carrier, and wherein the thickening agent has higher water solubility than that of the carrier. In some instances, the particles comprise that the thickening agent binds to the active agent. In some instances, the particles further comprise the carrier, and wherein the thickening agent binds to the active agent and the carrier. In some instances, the particles comprise the thickening agent that comprises a polysaccharide. In some instances, the thickening agent comprises hydroxypropyl methylcellulose (HPMC), hydroxypropyl cellulose, methyl cellulose, carboxymethylcellulose calcium, sodium carboxymethylcellulose, sodium alginate, xanthan gum, acacia, guar gum, locust bean gum, gum tragacanth, starch, carbopols, methylcellulose, polyvinylpyrrolidone, or any combination thereof. In some instances, the particles comprise the thickening agent and have an average particle size of from about 10 to about 50 μm, or about 15-200 microns, as measured by laser diffraction. In some instances, the particles have an average particle size of about 15 μm, or about 50-150 microns, as measured by laser diffraction. In some instances, the particles comprise the thickening agent and the carrier and have an average particle size of from about 10 to about 50 μm, as measured by laser diffraction. In some instances, the particles have an average particle size of about 20 or about 23 μm, as measured by laser diffraction. In some instances, the powdered therapeutic formulation further comprises a fluidizing agent. In some instances, the fluidizing agent comprises a tribasic calcium phosphate. In some instances, the administration of the powdered therapeutic formulation improves the pharmacokinetic parameter of the active agent by at least about: 20%, 25%, 30%, 40%, 45%, 50%, 60%, 70%, 80%, 90%, 100%, 150%, 200%, 250%, 300%, 400%, or 500%, when compared to administration of the corresponding formulation that comprises the active agent in the crystalline form. In some instances, the improved pharmacokinetic parameter comprises a greater relative bioavailability from 0 min to 15 min (rBA$_{0-15\ min}$), a greater relative bioavailability from 0 min to 30 min (rBA$_{0-30\ min}$), a greater relative bioavailability from 0 min to 60 min (rBA$_{0-60\ min}$), or any combination thereof. In some instances, the improved pharmacokinetic parameter comprises an average rBA$_{0-15\ min}$, and the improvement is at least about 100%, e.g., at least about: 115% or 150%. In some instances, the average rBA$_{0-15\ min}$ is about 150% to 1500% in serum of the subject. In some instances, the improved pharmacokinetic parameter comprises an average rBA$_{0-30\ min}$, and the improvement is at least about 80%, e.g., at least about 115%. In some instances, the improvement is about 400%. In some instances, the improved pharmacokinetic parameter comprises an average rBA$_{0-60\ min}$, and the improvement is at least 100%, e.g., at least about 115%. In some instances, the improvement is about 200%. In some instances, the improved pharmacokinetic parameter comprises a higher maximum blood concentration ($C_{max}$). In some instances, the improved pharmacokinetic parameter comprises a shorter time to reach maximum blood concentration (Tmax). In some instances, the improved pharmacokinetic parameter comprises an increased area under the curve (AUC) for blood concentration-time profile. In some instances, the powdered therapeutic formulation further comprises an additional active agent. In some instances, the additional active agent comprises caffeine, which is amorphous, crystalline, at least 20% of amorphous by weight of the caffeine, or any combination thereof. In some instances, at least about: 25%, 30%, 40%, 45%, 50%, 55%, 60%, 65%, 70%, 75%, 80%, 85%, 90%, 95%, or 98% by weight of the active agent is amorphous. In some instances, the powdered therapeutic formulation retains at least about: 80%, 85%, 90%, or 95% by weight of the active agent in a closed container after a period of at least about: 30, 60, 120, 180, 360, 720, or 1080 days. In some instances, the container is kept at about 15° C., about 20° C., about 30° C., about 40° C., about 50° C., about 60° C., or about 70° C., for example about 20° C. to about 40° C. at a standard atmosphere pressure with a relative humidity of about 50% to about 75%. For example, the relative humidity may be about 40%, about 45%, about 50%, about 55%, about 60%, about 65%, about 70%, about 75%, about 80%, or about 85%. In some instances, the container is kept at about 25° C. at a standard atmosphere pressure with a relative humidity of about 50%. In some instances, the crystalline form comprises a polymorph.

In some cases, an active agent disclosed herein has an average particle size (e.g., diameter) of about 5 μm or larger than 5 μm.

In some cases, an active agent is present in an amount of about: 2-4%, 1-5%, 1-10%, 1-15%, 1-20%, 1-25%, 1-30%, 1-40%, 10-50%, 10-40%, 10-30%, or 15-25%, by weight based on a weight of the particles or a powdered therapeutic formulation, for example about: 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, or 50%.

In some cases, particle size for each active agent, excipient and powder preparation are determined under a dry powder dispersion condition by a laser diffraction system (Mastersizer 2000, Malvern Instruments Ltd.).

Excipients

In some cases, a formulation disclosed herein comprises one or more excipients, e.g., different substance, or same substance but different sizes. In some instances, the excipient comprises a carrier, e.g., water-insoluble polysaccharide or oligosaccharide. In some instances, the carrier is selected from a group consisting of cellulose acetate, cellulose acetate butyrate, cellulose acetate propionate, cellulose acetate phthalate, chitosan, β-cyclodextrin, ethyl cellulose, hydroxypropylmethyl cellulose phthalate (HPMCP), microcrystalline cellulose, starch, and any combination thereof. In some instances, the excipient comprises a thickening agent, e.g., a water-soluble polysaccharide. In some instances, the thickening agent is selected from the group consisting of hydroxy propyl methyl cellulose (HPMC), acacia, alginic acid, colloidal silicone dioxide, carboxymethylcellulose calcium, gelatin, hydroxy propyl cellulose, hydroxyl propyl cellulose (hypromellose), methyl cellulose, sucrose, sodium alginate, sodium carboxy methyl cellulose, and any combination thereof. In some instances, the excipient comprises a first excipient (any excipient disclosed herein) and a second excipient (any excipient disclosed herein). In some instances, the excipient comprises a carrier (e.g., microcrystalline cellulose) and a thickening agent (e.g., HPMC).

In some instances, particles comprise a thickening agent that is present in an amount of about: 0.1-0.5%, 0.05-1%, 0.05-2%, 0.05-3%, 0.05-4%, 0.05-5%, 4-6%, 3-7%, 2-8%, 1-10%, or 1-20% by weight based on a weight of the particles or a powdered therapeutic formulation, for example about: 0.1, 0.2, 0.3, 0.4, 0.5, 0.6, 0.7, 0.8, 0.9, 1, 1.5, 2, 2.5, 3, 3.5, 4, 4.5, 5, 6, 7, 8, 9, 10, 11, 12, 13, 14, 15, 16, 17, 18, 19, or 20 percent. In some instances, particles comprise microcrystalline cellulose that is present in an amount of about: 10-95%, 10-75%, 15-55%, 20-75%, 35-75%, or 40-75% by weight based on a weight of the particles or a powdered therapeutic formulation, for example about: 10%, 20%, 30%, 40%, 50%, 60%, 70%, 75%, 80%, 85%, 90%, or 95%. In some instances, particles comprise a sugar alcohol that is present in an amount of about: 10-95%, 10-75%, 15-55%, 20-75%, 35-75%, or 40-75% by weight based on a weight of the particles or a powdered therapeutic formulation, for example about: 10%, 20%, 30%, 40%, 50%, 60%, 70%, 75%, 80%, 85%, 90%, or 95%. In some instances, particles comprise the pH adjusting agent that is present in an amount of about: 10-20%, 20-30%, 5-25%, 15-35%, or 5-40% by weight based on a weight of the particles or a powdered therapeutic formulation, for example about: 5%, 6%, 7%, 8%, 9%, 10%, 15%, 20%, 25%, 30%, 35%, or 40%.

In some instances, a particle or formulation disclosed herein comprises a pH adjusting agent. In some instances, the pH adjusting agent is selected from the group consisting of ascorbic acid, sodium ascorbate, tartaric acid, sodium tartrate, potassium tartrate, calcium tartrate, lithium tartrate, citric acid, sodium citrate, potassium citrate, calcium citrate, lithium citrate, phosphoric acid, sodium dihydrogenphosphate, sodium monohydrogenphosphate, lithium phosphate, potassium phosphate, calcium phosphate, sodium carbonate, sodium hydrogencarbonate, lactic acid, sodium lactate, potassium lactate, calcium lactate, acetic acid, sodium acetate, potassium acetate, calcium acetate, propionic acid, sulphuric acid, sodium sulphate, potassium sulphate, boric acid, sodium borate, maleic acid, lithium maleate, sodium maleate, potassium maleate, calcium maleate, succinic acid, lithium succinate, sodium succinate, potassium succinate, calcium succinate, fumaric acid, glutamic acid, formic acid, malic acid, hydrochloric acid, nitric acid, sodium hydroxide, potassium hydroxide, triethanolamine, diisopropanolamine, ammonia solution, monoethanole amine, diethanoleamine, triethanoleamine meglumine, sodium citrate, sodium bicarbonate, potassium bicarbonate, and any combination thereof. In some instances, a pH adjusting agent disclosed herein is acetic acid; adipic acid; ammonium aluminum sulphate; ammonium bicarbonate; ammonium carbonate; ammonium citrate, dibasic; ammonium citrate, monobasic; ammonium hydroxide; ammonium phosphate, dibasic; ammonium phosphate, monobasic; calcium acetate; calcium acid pyrophosphate; calcium carbonate; calcium chloride; calcium citrate; calcium fumarate; calcium gluconate; calcium hydroxide; calcium lactate; calcium oxide; calcium phosphate, dibasic; calcium phosphate, monobasic; calcium phosphate, tribasic; calcium sulphate; carbon dioxide; citric acid; cream of tartar; fumaric acid; gluconic acid; glucono-delta-lactone; hydrochloric acid; lactic acid; magnesium carbonate; magnesium citrate; magnesium fumarate; magnesium hydroxide; magnesium oxide; magnesium phosphate; magnesium sulphate; malic acid; manganese sulphate; metatartaric acid; phosphoric acid; potassium acid tartrate; potassium aluminum sulphate; potassium bicarbonate; potassium carbonate; potassium chloride; potassium citrate; potassium fumarate; potassium hydroxide; potassium lactate; potassium phosphate, dibasic; potassium phosphate, tribasic; potassium sulphate; potassium tartrate; potassium tripolyphosphate; sodium acetate; sodium acid pyrophosphate; sodium acid tartrate; sodium aluminum phosphate; sodium aluminum sulphate; sodium bicarbonate; sodium bisulphate; sodium carbonate; sodium citrate; sodium fumarate; sodium gluconate; sodium hexametaphosphate; sodium hydroxide; sodium lactate; sodium phosphate, dibasic; sodium phosphate, monobasic; sodium phosphate, tribasic; sodium potassium hexametaphosphate; sodium potassium tartrate; sodium potassium tripolyphosphate; sodium pyrophosphate, tetrabasic; sodium tripolyphosphate; sulphuric acid; sulphurous acid; tartaric acid; or any combination thereof.

In some instances, a particle or formulation disclosed herein comprises a sugar alcohol. In some instances, the sugar alcohol is selected from the group consisting of mannitol, glycerol, galactitol, fucitol, inositol, volemitol, maltotriitol, maltoetetraitol, polyglycitol, erythritol, threitol, ribitol, arabitol, xylitol, allitol, dulcitol, glucitol, sorbitol, altritol, iditol, maltitol, lactitol, isomalt, and any combination thereof. In some instances, the sugar alcohol has 3, 4, 5, 6, 7, 12, 18, or 24 carbons.

In some instances, formulations may further comprise a fluidizing agent. For example, the fluidizing agent is a metal salt (e.g., a calcium salt) or a phosphate salt. In some instances, the fluidizing agent is a calcium phosphate salt, e.g., tribasic calcium phosphate. The tribasic calcium phosphate can be about 0.1% to about 5.0% of the total weight of the powder formulation, for example about: 0.1%-5%, 0.1%-4%, 0.1%-3%, 0.1%-2%, 0.1%-1%, 0.1%-0.5%, 0.5%-5%, 0.5%-4%, 0.5%-3%, 0.5%-2%, 0.5%-1%, 1%-5%, 1%-4%, 1%-3%, 1%-2%, 2%-5%, 2%-4%, 2%-3%, 3%-5%, 3%-4%, or 4%-5% of the total weight of the powder formulation. In some instances, the tribasic calcium phosphate is about 0.5% to about 1.0% of the total weight of the powder formulation. In some instances, the tribasic calcium phosphate is about 0.5% to about 1.5% of the total weight of the powder formulation. In some instances, the tribasic calcium phosphate is about 0.8% of the total weight of the powder formulation.

In some cases, an excipient has an average particle size of about 100 μm or less, e.g., about: 95 μm, 90 μm, 85 μm, 80 μm, 75 μm, 70 μm, 65 μm, 60 μm, 55 μm, 50 μm, 45 μm, 40 μm, 35 μm, 30 μm, 25 μm, 20 μm, 15 μm, 10 μm, 5 μm or less. In some instances, a formulation herein may comprise a first excipient with an average particle diameter size of about 30 μm or less, and a second excipient with an average particle size diameter of about 30 to about 100 μm. The first excipient may have an average particle diameter size of about 30 μm or less, for example, about: 30-25 μm, 30-20 μm, 30-15 μm, 30-10 μm, 30-5 μm, 25-20 μm, 25-15 μm, 25-10 μm, 25-5 μm, 20-15 μm, 20-10 μm, 20-5 μm, 15-10 μm, 15-5 μm or 10-5 μm. In some instances, the first excipient has an average particle diameter size of about 15-30 μm. In some instances, the first excipient has an average particle diameter size of about 18-20 μm. In some instances, the first excipient has an average particle diameter size of about 20 μm. The second excipient may have an average particle diameter size of about 30 to about 100 μm, for example, about: 30-90 μm, 30-80 μm, 30-70 μm, 30-60 μm, 30-50 μm, 30-40 μm, 40-90 μm, 40-80 μm, 40-70 μm, 40-60 μm, 40-50 μm, 50-90 μm, 50-80 μm, 50-70 μm, 50-60 μm, 60-90 μm, 60-80 μm, 60-70 μm, 70-90 μm, 70-80 μm, or 80-90 μm. In some instances, the second excipient has an average particle diameter size of about 45-65 μm. In some instances, the second excipient has an average particle diameter size of about 45-55 μm. In some instances, the second excipient has an average particle diameter size of about 50-55 μm. In some instances, the second excipient has an average particle diameter size of about 50 μm. In some instances, the first excipient has an average particle diameter size of about 15 to about 30 μm and the second excipient has an average particle diameter size of about 45 to about 65 µm. In some instances, the first excipient has an average particle size of about 20 µm and the second excipient has an average particle size diameter of about 50 to about 55 µm. In some instances, the first excipient has an average particle diameter size of about 20 µm, and the second excipient has an average particle size diameter of about 50 µm. In some cases, the excipient is substantially free of particles with an average particle diameter size of about 31 to about 44 µm. In some instances, the excipient is substantially free of particles with an average particle diameter size of about 31 to about 49 µm. In some cases, substantially free of particles with an average particle diameter size means less than 15%, 10%, 5%, or 2% of all the particles fall into the given range.

In some cases, one or more excipient(s) (e.g., microcrystalline cellulose, HPMC, mannitol, TCP) may comprise at least about 5% of the total weight of the powder formulation, for example, at least about: 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or 98% of the total weight of the powder formulation. The excipient(s) may comprise about 15% to about 99% of the total weight of the powder formulation, for example, about: 15%-99%, 20%-99%, 30%-99%, 40-99%, 50-99%, 60-99%, 70-99%, 80-99%, 90-99%, 15%-90%, 20%-90%, 30%-90%, 40-90%, 50-90%, 60-90%, 70-90%, 80-90%, 15%-80%, 20%-80%, 30%-80%, 40-80%, 50-80%, 60-80%, 70-80%, 15%-70%, 20%-70%, 30%-70%, 40-70%, 50-70%, 60-70%, 15%-60%, 20%-60%, 30%-60%, 40-60%, 50-60%, 15%-50%, 20%-50%, 30%-50%, 40-50%, 15%-40%, 20%-40%, 30%-40%, 15%-30%, 20%-30%, or 15-20% of the total weight of the powder formulation. In some instances, the first excipient comprises about 10 to about 90% of the total weight of the powder formulation, for example, about: 10%-90%, 15%-90%, 20%-90%, 30%-90%, 40-90%, 50-90%, 60-90%, 70-90%, 80-90%, 10%-80%, 15%-80%, 20%-80%, 30%-80%, 40-80%, 50-80%, 60-80%, 70-80%, 10%-70%, 15%-70%, 20%-70%, 30%-70%, 40-70%, 50-70%, 60-70%, 10%-60%, 15%-60%, 20%-60%, 30%-60%, 40-60%, 50-60%, 10%-50%, 15%-50%, 20%-50%, 30%-50%, 40-50%, 10%-40%, 15%-40%, 20%-40%, 30%-40%, 10%-30%, 15%-30%, 20%-30%, 10%-20%, 15-20%, or 10%-15% of the total weight of the powder formulation. In some instances, the first excipient comprises about 70% to about 90% of the total weight of the powder formulation. In some instances, the first excipient comprises about 70% to about 90% of the total weight of the powder formulation. In some instances, the second excipient comprises about 5% to about 15% of the total weight of the powder formulation, for example, about 5%-15%, 5%-10%, or 10%-15% of the total weight of the powder formulation. In some instances, the second excipient comprises about 10% of the total weight of the powder formulation. For example, the first excipient comprises about 8% to about 90% of the total weight of the formulation, and the second excipient comprises about 10% of the total weight of the formulation. In some instances, the first excipient is about 5% to about 90% of the total weight of the powder formulation, and the second excipient is about 10% of the total weight of the powder formulation.

With respect to the microcrystalline cellulose component of the powder formulations presented herein, generally, acceptable microcrystalline cellulose can include microcrystalline cellulose obtained by decomposing cellulose materials such as pulp by either or both of acid and alkaline hydrolyses, then purifying the hydrolysate, and crushing or grinding it before, during, or after drying. Microcrystalline cellulose of a select average particle diameter size can be obtained, for example, via appropriate processing, e.g., via fine grinding using a high-speed rotary impact mill or air attrition mill as necessary, and size sorting. In some instances, microcrystalline cellulose components utilized as part of the microcellulose of the powder formulations presented herein can include products available under the trade names of Ceolus® PH-F20JP (e.g., average particle size about 20-23 microns, bulk density about 0.23 g/cm$^3$, repose angle not less than 60 degrees), Ceolus® PH-301 (e.g., average particle size about 50 microns, bulk density about 0.41 g/cm$^3$, repose angle about 41 degrees), Ceolus® PH-101 (e.g., average particle size about 50 microns, bulk density about 0.29 g/cm$^3$, repose angle about 45 degrees), Ceolus® PH-102 (e.g., average particle size about 90 microns, bulk density about 0.3 g/cm$^3$, repose angle about 42 degrees), and Ceolus® PH-302 (available from Asahi Kasei Corporation, e.g., average particle size about 90 microns, bulk density about 0.43 g/cm$^3$, repose angle about 38 degrees), and Avicel® PH-105 (e.g., average particle size about 20 microns, bulk density about 0.20-0.30 g/cm$^3$), Avicel® PH-101 (e.g., average particle size about 50 microns, bulk density about 0.26-0.31 g/cm$^3$), Avicel® PH-102 (e.g., average particle size about 100 microns, bulk density about 0.28-0.33 g/cm$^3$), Avicel® PH-301 (e.g., average particle size about 50 microns, bulk density about 0.34-0.45 g/cm$^3$), and Avicel® PH-302 (available from FMC Biopolymer Corporation, e.g., average particle size about 100 microns, bulk density about 0.35-0.46 g/cm$^3$). In some instances, powder formulations that can be used in conjunction with the methods and formulations presented herein can comprise Ceolus® PH-F20JP and Ceolus® PH-301.

Average particle size diameters, for example, the average particle size diameters of the microcrystalline portions of the powder formulations described herein, can be determined using standard techniques, for example, via a laser-diffraction particle size distribution analyzer or via sorting methods. The average particle diameter size refers to a diameter that divides particles into two groups of equal numbers: a group with greater diameters and a group with smaller diameters. The average diameter size determined using a laser-diffraction particle size distribution analyzer corresponds to 50% volume in a determined cumulative particle size distribution curve. The average particle diameter size can, for example, be determined by a sorting method that corresponds to 50% (W/W) on a cumulative particle size distribution curve that can be obtained by sorting an appropriate amount of the particle being assessed, for an appropriate time, e.g., ten minutes, on an electromagnetic sieve shaker, using standard sieves and weighing the sample remaining on each sieve.

In some instances, the microcrystalline cellulose component of the formulation comprises a first microcrystalline cellulose portion with an average particle diameter size of about 30 µm or less, and a second microcrystalline cellulose portion with an average particle size diameter of about 30-100 µm. In some instances, the first microcrystalline cellulose portion has an average particle diameter size of about 15-30 µm. In some instances, the first microcrystalline cellulose portion has an average particle diameter size of about 18-20 µm. In some instances, the first microcrystalline cellulose portion has an average particle diameter size of about 20 µm. In some instances, the second microcrystalline cellulose portion has an average particle diameter size of about 45-65 µm. In some instances, the second microcrystalline cellulose portion has an average particle diameter size of about 45-55 µm. In some instances, the second microcrystalline cellulose portion has an average particle diameter size of about 50-55 μm. In some instances, the second microcrystalline cellulose portion has an average particle diameter size of about 50 μm. In some instances, the first microcrystalline cellulose portion has an average particle diameter size of about 20 μm, and the second microcrystalline cellulose portion has an average particle size diameter of about 50 μm. In some instances, the first microcrystalline cellulose portion has an average particle diameter size of about 30 μm or less, for example, about 15-30 μm, about 18-20 μm, or about 20 μm, and the second microcrystalline cellulose portion has an average particle diameter size of about 45-65 μm, about 45-55 μm, about 50-55 μm, or about 50 μm.

In some instances, the microcrystalline cellulose component of the powder formulation comprises about 10 to about 99%, e.g., about 15 to about 99%, of the total weight of the formulation. In some instances, the microcrystalline cellulose component of the powder formulation comprises about 53 to about 99%, about 76 to about 99%, about 76 to about 97%, about 90 to about 97%, or about 90 to about 95% of the total weight of the formulation. In some instances, the microcrystalline cellulose component of the powder formulation comprises about 10 to about 98%, about 18 to about 98%, about 18 to about 91%, about 67 to about 91%, or about 67 to about 83%. In some instances, the microcrystalline cellulose component of the powder formulation comprises about 53%, about 76%, about 90%, about 95%, about 97%, or about 99% of the total weight of the formulation. In some instances, the microcrystalline cellulose component of the powder formulation comprises about 10%, about 18%, about 66%, about 83%, about 91%, or about 98% of the total weight of the formulation. In some instances, the first microcrystalline cellulose portion comprises about 3.0 to about 90%, e.g., about 8.0 to about 90%, of the total weight of the formulation, and the second microcrystalline cellulose portion comprises about 10% of the total weight of the formulation. In some instances, the first microcrystalline cellulose portion comprises about 43 to about 89%, about 66 to about 89%, about 66 to about 87%, about 80 to about 87%, or about 80 to about 85% of the total weight of the formulation, of the total weight of the formulation, and the second microcrystalline cellulose portion comprises about 10% of the total weight of the formulation. In some instances, the microcrystalline cellulose component of the powder formulation comprises about 1 to about 88%, about 8 to about 88%, about 8 to about 81%, about 57 to about 81%, or about 57 to about 83%, and the second microcrystalline cellulose portion comprises about 10% of the total weight of the formulation. In some instances, the microcrystalline cellulose component of the powder formulation comprises about 43%, about 66%, about 80%, about 85%, about 87%, or about 89% of the total weight of the formulation, and the second microcrystalline cellulose portion comprises about 10% of the total weight of the formulation. In some instances, the microcrystalline cellulose component of the powder formulation comprises about 1%, about 8%, about 57%, about 73%, about 81%, or about 88% of the total weight of the formulation, and the second microcrystalline cellulose portion comprises about 10% of the total weight of the formulation.

With respect to tribasic calcium phosphate (also known as hydroxyapatite), any pharmaceutically acceptable tribasic calcium phosphate can be used in conjunction with the methods and formulations presented herein. In some instances, the tribasic calcium phosphate utilized has an average particle diameter of about 10-100 μm, for example, about 10-75 μm, about 10-50 μm, about 10-30 μm, or about 10 μm. In some instances, not less than 90% of the tribasic calcium phosphate particles in the powder formulations presented herein have a diameter less than 150 μm, and not more than 5% of the particles in the powder formulation have a diameter less than 10 μm. In some instances, the overall average particle size of the tribasic calcium phosphate particles in the powder formulations presented herein about 15 to about 30 μm, about 18 to about 25 μm, about 18 to about 20 μm, or about 20 μm.

In some instances, greater than or equal to about 90% of the tribasic calcium phosphate particles have a diameter less than 150 μm. In some instances, the overall average particle size of the tribasic calcium phosphate particles is about 15 to about 30 μm, about 18 to about 25 μm, about 18 to about 20 μm, or about 20 μm. In some instances, less than or equal to about 5% of the tribasic calcium phosphate particles have a diameter less than 10 μm. In some instances, for the tribasic calcium phosphate particles, greater than or equal to about 90% of the particles have a diameter less than 150 μm; and the overall average particle size is about 15 to about 30 μm, about 18 to about 25 μm, about 18 to about 20 μm, or about 20 μm; and less than or equal to about 5% of the particles have a diameter less than 10 μm.

In some instances, tribasic calcium phosphate comprises at least: about 0.1%, about 0.2%, about 0.3%, about 0.4%, about 0.5%, about 0.6%, about 0.7%, about 0.8%, about 0.9%, about 1%, about 1.5%, 2.0%, for example, 0.5-1.0% of the total weight of the formulation. In specific instances of the methods of treating headache, including migraine, the tribasic calcium phosphate comprises about 0.8% of the total weight of the formulation.

Doses

In some cases, a total dose of a powder formulation administered can be at least about 0.1 mg, for example, at least about: 0.1 mg, 0.2 mg, 0.3 mg, 0.4 mg, 0.5 mg, 0.6 mg, 0.7 mg, 0.8 mg, 0.9 mg, 1 mg, 1.5 mg, 2 mg, 2.5 mg, 3 mg, 3.5 mg, 4 mg, 4.5 mg, 5 mg, 5.5 mg, 6 mg, 6.5 mg, 7 mg, 7.5 mg, 8 mg, 8.5 mg, 9 mg, 9.5 mg, 10 mg, 11 mg, 12 mg, 13 mg, 14 mg, 15 mg, 16 mg, 17 mg, 18 mg, 19 mg, 20 mg, 25 mg, or 50 mg. The total dose of the powder formulation administered can be about 0.1 to about 50 mg, for example, about 0.1-50 mg, about 0.1-25 mg, about 0.1-20 mg, about 0.1-15 mg, about 0.1-10 mg, about 0.1-5 mg, about 0.1-2 mg, about 0.1-1 mg, about 0.1-0.5 mg, about 0.2-50 mg, about 0.2-25 mg, about 0.2-20 mg, about 0.2-15 mg, about 0.2-10 mg, about 0.2-5 mg, about 0.2-2 mg, about 0.2-1 mg, about 0.2-0.5 mg, about 0.5-55 mg, 0.5-25 mg, about 0.5-20 mg, about 0.5-15 mg, about 0.5-10 mg, about 0.5-5 mg, about 0.5-2 mg, about 0.5-1 mg, about 1-25 mg, about 1-50 mg, about 1-20 mg, about 1-15 mg, about 1-10 mg, about 1-5 mg, about 1-2 mg, about 2-50 mg, about 2-25 mg, about 2-20 mg, about 2-15 mg, about 2-10 mg, about 2-5 mg, about 5-25 mg, about 5-20 mg, about 5-15 mg, about 5-10 mg, about 10-50 mg, about 0.5-25 mg, about 10-20 mg, about 10-15 mg, about 15-25 mg, or about 15-20 mg. For example, the total dose of the powder formulation administered is about 25 mg.

In some cases, a powder formulation comprises a total dose of an active agent administered of at least about 0.1 mg, for example, at least about: 0.1 mg, 0.2 mg, 0.3 mg, 0.4 mg, 0.5 mg, 0.6 mg, 0.7 mg, 0.8 mg, 0.9 mg, 1 mg, 1.5 mg, 2 mg, 2.5 mg, 3 mg, 3.5 mg, 4 mg, 4.5 mg, 5 mg, 5.5 mg, 6 mg, 6.5 mg, 7 mg, 7.5 mg, 8 mg, 8.5 mg, 9 mg, 9.5 mg, or 10 mg. The powder formulation may comprise a total dose of an active agent administered at about 0.1 to about 10.0 mg, for example, about 0.1-10.0 mg, about 0.1-9.0 mg, about 0.1-8.0 mg, about 0.1-7.0 mg, about 0.1-6.0 mg, about 0.1-5.0 mg, about 0.1-4.0 mg, about 0.1-3.0 mg, about 0.1-2.0 mg, about 0.1-1.0 mg, about 0.1-0.5 mg, about 0.2-10.0 mg, about 0.2-9.0 mg, about 0.2-8.0 mg, about 0.2-7.0 mg, about 0.2-6.0 mg, about 0.2-5.0 mg, about 0.2-4.0 mg, about 0.2-3.0 mg, about 0.2-2.0 mg, about 0.2-1.0 mg, about 0.2-0.5 mg, about 0.5-10.0 mg, about 0.5-9.0 mg, about 0.5-8.0 mg, about 0.5-7.0 mg, about 0.5-6.0 mg, about 0.5-5.0 mg, about 0.5-4.0 mg, about 0.5-3.0 mg, about 0.5-2.0 mg, about 0.5-1.0 mg, about 1.0-10.0 mg, about 1.0-5.0 mg, about 1.0-4.0 mg, about 1.0-3.0 mg, about 1.0-2.0 mg, about 2.0-10.0 mg, about 2.0-9.0 mg, about 2.0-8.0 mg, about 2.0-7.0 mg, about 2.0-6.0 mg, about 2.0-5.0 mg, about 2.0-4.0 mg, about 2.0-3.0 mg, about 5.0-10.0 mg, about 5.0-9.0 mg, about 5.0-8.0 mg, about 5.0-7.0 mg, about 5.0-6.0 mg, about 6.0-10.0 mg, about 6.0-9.0 mg, about 6.0-8.0 mg, about 6.0-7.0 mg, about 7.0-10.0 mg, about 7.0-9.0 mg, about 7.0-8.0 mg, about 8.0-10.0 mg, about 8.0-9.0 mg, or about 9.0-10.0 mg. For example, the total dose administered at about 0.5 mg. In some instances, the total dose administered is about 0.1-5 mg. In some instances, the total amount administered is about 0.5-5 mg. In some instances, the total amount administered is about 0.5-3 mg. In some instances, the total amount of administered is about 1-2 mg.

Pharmaceutical Kits

A pharmaceutical kit is provided for use of a therapeutic formulations described herein. In some instances, a kit comprising a unit dosage of a dry powder formulation suitable for intranasal administration and an intranasal delivery device or dispenser is provided. In some instances, a therapeutic formulation is present in a therapeutic quantity. In some instances, kits include a carrier, package, or container that is compartmentalized to receive one or more blister packs, bottles, tubes, capsules, and the like. In certain instances, a pharmaceutical formulation is presented in a pack or dispenser device which contains one or more unit dosage forms containing a compound provided herein. In some instances, a pack contains metal or plastic foil, such as a blister pack. In some instances, a pack contains capsules, cartridges, vials, or tubes. In some instances, a pack or dispenser device is accompanied by instructions for administration. In some instances, a dispenser is disposable or single use, while in some instances, a dispenser is reusable. In certain instances, a pharmaceutical formulation is pre-loaded into a device. In some instances, nasal applicator has a volume of not more than about: 3 mL, 5 mL, 10 mL, 15 mL, 20 mL, 30 mL, 40 mL, or 50 mL.

In some instances, a pack or dispenser also accompanied with a notice as required by a governmental agency regulating the manufacture, use, or sale of pharmaceuticals. This notice states that a drug is approved by the agency for human or veterinary administration. Such notice, for example, is a labeling approved by the U.S. Food and Drug Administration for prescription drugs, or an approved product. Formulations containing a compound provided herein formulated in a compatible pharmaceutical carrier are also prepared, placed in an appropriate container, and labeled for treatment of an indicated condition.

The articles of manufacture provided herein can also contain an intranasal administration or dispensing device. A device can rely on the patient's inspiration to transport a formulation or pumps can be provided or built into devices to assist the aerosolization and transport of a formulation. Alternatively, a propellant can be included with or it can be stored within devices.

Such kits optionally comprise an identifying description or label for containers. In some instances, a label is on a container with letters, numbers or other characters forming the label and attached, molded or etched into a container itself; a label is associated with a container when it is present within a receptacle or carrier that also holds the container, e.g., as a package insert. In some instances, a label is used to indicate that the contents are to be used for a specific therapeutic application. In yet some instances, a label also indicates directions for use of the contents, such as in methods described herein. A set of instructions can also be included, generally in the form of a package insert. An informational material can contain instructions on how to dispense the pharmaceutical formulation, including description of the type of patients who can be treated, the schedule (e.g., dose and frequency), and the like.

III. Treatment

In some instances, a powdered therapeutic formulation or a method disclosed herein is used in the treatment or prevention of a disease or a condition in a subject in need thereof. In some instances, the disease or condition is pain, hormone disorder, a headache, amyotrophic lateral sclerosis, Parkinson's disease, stress, anxiety, nausea, emesis, aggression, pain, neuropathic pain, sleeplessness, insomnia, restless leg syndrome, depression, or any combination thereof. In some instances, the disease or condition is a headache. In some instances, the headache is a migraine headache, a cluster headache, a hemicrania continua headache, a chronic headache, a tension headache, a chronic tension headache, or any combination thereof. In some instances, the headache is a migraine headache. In some instances, the headache is a migraine headache with aura. In some instances, the headache is a migraine headache without aura. In some instances, the headache is moderate to severe. In some instances, the headache is acute. In some instances, the powdered therapeutic formulation is administered for at least one day, two days, three days, four days, five days, six days, one week, one month, or one year. In some instances, the administration of the powdered therapeutic formulation is 1 time, 2 times, 3 times, 4 times, 5 times, 6 times, 7 times, or 8 times daily. In some instances, the powdered therapeutic formulation is in a single unit dose. In some instances, the powdered therapeutic formulation is a unit dose of from about 5 mg to about 50 mg, for example about: 10, 15, 20, 25, 30, 35, 40, or 45 mg. In some instances, a unit dosage of the powdered therapeutic formulation contains about 0.1 mg to about 25 mg of the active agent, for example about: 1, 2, 3, 4, 5, 6, 7, 8, 9, 10, 15, or 20 mg. In some instances, the subject is a primate. In some instances, the subject is a human. In some instances, the subject is a monkey.

In some instances, provided herein is a method of treating a disease or a condition, including pain, headache, or hormone disorder, comprising administering intranasally (e.g., through a nasal cavity) a powder formulation comprising an active agent. Other possible mucosal routes of administration include conjunctival administration, buccal administration, and sublingual administration. Buccal and sublingual have the advantage of being user friendly and non-invasive, and can be self-administered. Another alternative route to oral is transdermal, delivery of active agents through the patient's skin. The last form of administration is intradermal injection (administration to the dermis) and subcutaneous injection (administration to the fat layer below the skin). In some instances, the powder formulation comprises an active agent, microcrystalline cellulose with an average particle diameter size of about 100 μm or less, and tribasic calcium phosphate. In some instances, the powder formulation comprises an active agent, a microcrystalline cellulose portion with an average particle size diameter of about 50-55 µm, e.g., about 50 µm, comprising about 10% of the total weight of the powder formulation, a microcrystalline cellulose portion with an average particle size of about 20 µm comprising about 3 to about 90%, e.g., about 8 to about 90%, of the total weight of the powder formulation and, optionally, a fluidizing agent. In some instances, the powder formulations utilized as part of the methods further comprise an active agent disclosed herein, e.g. caffeine, for example, anhydrous caffeine.

In some instances, the headache treated by the methods provided herein is a cluster headache, chronic daily headache, or migraine, including adult migraine or pediatric migraine. The migraine can be migraine with aura or migraine without aura. In some instances, the methods presented herein are methods for acute treatment of a human having a migraine with or without aura. In some instances, the methods presented herein are methods for chronic treatment of migraine with or without aura.

"Treating," or "Treatment" as used with a method disclosed herein, refers to the amelioration, reduction, or elimination of at least one symptom of the disorder being treated. In some instances, the methods of treating headache or pain ameliorate, reduce, or eliminate at least one or more symptoms. Symptoms of headache, e.g., cluster headache, chronic daily headache or migraine, may include pain. Symptoms can also include, for example, nausea, vomiting, photophobia, phonophobia, osmophobia (aversion to, or hypersensitivity to, odors), vertigo, and/or allodynia. The symptom or symptoms can, for example, be evaluated via a four point severity scale as follows: 0=none 1=mild symptom, not interfering with normal daily activities 2=moderate symptom, causing some restriction to normal activities 3=severe, leading to inability to perform normal daily activities. Alternatively, or additionally, a symptom or symptoms, including the four listed above, can be evaluated via a four-point functional disability scale that assesses the level of impairment a symptom has on a patient's ability to perform usual daily activities, as follows: 0=not at all impaired 1=slightly impaired 2=moderately impaired 3=severely or completely impaired. See Cephalalgia 1991; 11:1-12. In some instances, the headache or pain has a severity of more than about any of 1, 2, 3, 4, 5, 6, 7, 8, 9, or 10 on a scale of 0 to 10. In some instances, the intensity of headache or pain, for example, pain associated with migraine, can be measured according to a 4-point severity scale (0=no pain, 1=mild, 2=moderate, 3=severe). In some instances, the methods of treating headache, for example migraine, presented herein reduce the severity of headache pain, for example pain associated with migraine, by at least one point on such a 4-point severity scale.

In some instances, the methods of treating a disease or condition can ameliorate, reduce, or eliminate at least one symptom within 10 minutes, 15 minutes, 20 minutes, 25 minutes, 30 minutes, 45 minutes, 1 hour, 1.5 hours, 2 hours, 2.5 hours, 3 hours, or 4 hours of intranasally administering a powder formulation presented herein. In some instances, the amelioration, reduction, or elimination of at least one symptom is sustained for about 3 hours, 4 hours, 5 hours, 6 hours, 8 hours, 12 hours, 18 hours, 36 hours, or 48 hours.

In some instances, presented herein is a method comprising: intranasally administering to a subject a powder formulation comprising: a) an active agent, wherein the total dose of an active agent being administered is about 0.1-10.0 mg; b) a microcrystalline cellulose component with an average particle size diameter of about 100 µm or less; and c) tribasic calcium phosphate. Herein, unless otherwise noted, "the total dose of DHE being administered" and like phrasing means the total amount of parent DHE in the DHE form, e.g., amount of DHE free base in a pharmaceutically acceptable DHE salt, being administered. In some instances, the powder formulation comprises DHE mesylate, and the total amount of DHE free base of the DHE mesylate being administered is about 0.1-10.0 mg. In some instances, the powder formulation is administered to a single nostril of the subject. In some instances, a portion of the powder formulation is administered to each nostril of the subject. For example, in some instances of the method, about half of the powder formulation is administered to one nostril and about half of the powder formulation is administered to the other nostril of the subject.

In some instances, for treating a disease or condition, a total amount of the powder formulation administered is about: 5 mg, 10 mg, 15 mg, 20 mg, 25 mg, 30 mg, 35 mg, 40 mg, 45 mg, or 50 mg, into a single or both nostrils. In some instances, the total amount of the powder formulation is administered into a single nostril. In some instances, a portion of the total amount of the powder formulation is administered into each nostril. In some instances, about half of the total amount of the powder formulation is administered into one nostril and the remaining half is administered into the other nostril.

In some instances, a total dose of an active agent administered is about 0.1-6.0 mg. In some instances, the total dose of an active agent administered is about 0.5-6.0 mg. In some instances, the total dose of an active agent administered is about 1.0-6.0 mg. In some instances, the total dose of an active agent administered is about 2.0-4.0 mg. In some instances, the total dose of an active agent administered is about 0.1 mg, about 0.5 mg, about 1.0 mg, about 1.5 mg, about 2.0 mg, about 3.0 mg, about 4.0 mg, about 5.0 mg, about 7.5 mg, or about 10.0 mg. In some instances, the total dose is administered into a single nostril. In some instances, a portion of the total dose is administered into each nostril. In some instances, about half of the total dose is administered into one nostril and the remaining half is administered into the other nostril.

In some instances, presented herein is a method comprising: intranasally administering to a human in need thereof, a powder formulation comprising: a) an active agent; b) an excipient component comprising a first excipient portion with an average particle size of about 30 µm or less, for example, about 15-30 µm, about 18-20 µm, or about 20 µm, and a second excipient portion with an average particle size diameter of about 45-65 µm, for example, about 45-55 µm or about 50-55 µm, e.g., about 50 µm, wherein the first excipient portion comprises about 80 to about 90%, e.g., about 85 to about 90%, of the total weight of the formulation, and the second excipient portion comprises about 10% of the total weight of the formulation; and c) fluidizing agent (e.g. tribasic calcium phosphate) comprising about 0.5-1.0%, e.g., about 0.8%, of the total weight of the formulation. In some instances, the powder formulation further comprises caffeine, for example, about 1-2% of an active agent disclosed herein, e.g. caffeine, for example, anhydrous caffeine.

In some instances, presented herein is a method of treating headache, including migraine, comprising: intranasally administering to a human in need thereof, a powder formulation comprising: a) an active agent (e.g., DHE or a salt thereof, DHE mesylate), wherein the total dose of an active agent being administered is about 2.0 mg; b) a microcrystalline cellulose component comprising a first microcrystalline cellulose portion with an average particle size of about 30 μm or less, for example, about 15-30 μm, about 18-20 μm, or about 20 μm, and a second microcrystalline cellulose portion with an average particle size diameter of about 45-65 μm, for example, about 45-55 μm or about 50-55 μm, e.g., about 50 μm, wherein the first microcrystalline cellulose portion comprises about 75 to about 90%, e.g., about 80 to about 90%, of the total weight of the formulation, and the second microcrystalline portion comprises about 10% of the total weight of the formulation; and c) tribasic calcium phosphate comprising about 0.5-1.0%, e.g., about 0.8%, of the total weight of the formulation. In some instances, the powder formulation further comprises a thickening agent, for example HPMC, which can be present in about 0.1-5% of a total weight. In some instances, the powder formulation further comprises a pH adjuster, for example ascorbic acid, which can be present in about 0.5-5% of a total weight. In some instances, the powder formulation further comprises a sugar alcohol, for example mannitol, which can be present in about 10-95.0% of a total weight. In some instances, the powder formulation further comprises an active agent, for example, about 5-10% of caffeine, e.g., anhydrous caffeine.

In some instances, of such methods of treating headache, including migraine, the powder formulation further comprises a fluidizing agent. Fluidizing agents include but are not limited to tribasic calcium phosphate, hydrous silicon dioxide, light anhydrous silicic acid, crystalline cellulose, synthetic aluminum silicate, calcium silicate, titanium oxide, stearic acid, calcium stearate, magnesium stearate, talc, cornstarch, magnesium metasilicate aluminate, anhydrous calcium hydrogenphosphate, synthetic hydrotalcite, and magnesium metasilicate aluminate. In some instances, the fluidizing agent is tribasic calcium phosphate. In some instances, the tribasic calcium phosphate comprises about 0.5-1.0% of the total weight of the formulation. In specific instances of the methods of treating migraine, the tribasic calcium phosphate comprises about 0.8% of the total weight of the formulation.

In some instances, the powder formulations utilized as part of such methods of treating headache, including migraine, further comprises an active agent disclosed herein, e.g. caffeine, for example, anhydrous caffeine. In some instances, the powder formulations utilized as part of the methods of treating migraine comprise about 1-60% of an active agent.

In some cases, presented herein is a powder formulation comprising one or more of an active agent (e.g., DHE, indomethacin, testosterone); a microcrystalline cellulose component (e.g., CEOLUS PH-F20JP, about 20-23 microns in particle size, or a mixture of CEOLUS PH-F20JP and CEOLUS PH-301); a thickening agent (e.g., HPMC); d) a sugar alcohol (e.g., mannitol, about 53-300 microns in particle size); a pH adjuster (e.g., ascorbic acid), a fluidizing agent (e.g., tribasic calcium phosphate); and, optionally an additional active agent disclosed herein, e.g. caffeine, for example, anhydrous caffeine.

In some instances, the powder formulation is prepared by fluid bed granulation of all its components. In some instances, the powdered therapeutic formulation comprises an active agent, a thickening agent, a carrier, and a sugar alcohol. In some instances, the active agent is amorphous, e.g., at least 20% amorphous. In some instances, the active agent is spray dried, e.g., with the thickening agent. In some instances, the thickening agent is a binder of low viscosity grade, e.g., HPMC. In some instances, the sugar alcohol is mannitol. In some instances, the sugar alcohol has a particle size diameter of about 53 to about 300 microns. In some instances, all components are aggregated together enough to withstand delivery from device and ensure deposition in same location. In some instances, the aggregation is loose enough for immediate break-up to individual components upon deposition on mucosa. In some instances, the particle size diameter of the powder formulation is about 50 microns to about 150 microns, e.g., about 150 microns. In some instances, the powder formulation has an angle of repose less than 55°, e.g., less than: 50°, 45°, 40°, 35°, 30°, or 25°. In some instances, the powder formulation is free from a fluidizing agent.

EXAMPLES

Example 1

Design of Device

Figure 5:
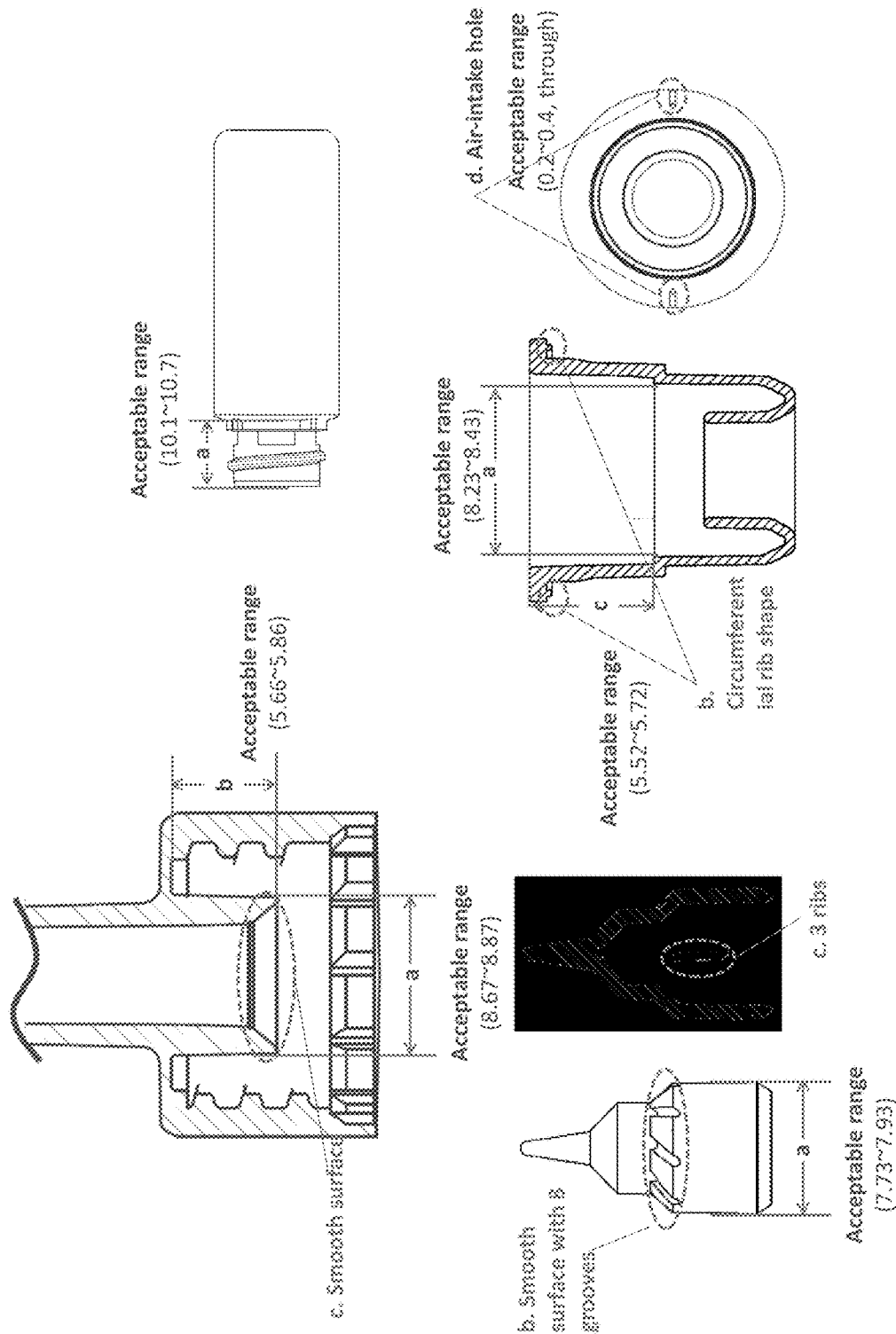
FIG. 5 illustrates measurements of the parts. The width of the thread of the pump "a" is 10.1-10.7 mm, and can be adjusted by 0.4 mm shorter or longer, in order to minimize the risk of insufficient seal between the retainer and the pump, and between the nozzle and the retainer.

A device comprises a nozzle (1), a poppet valve (2), a retainer (3), and a pump (4), as shown in FIG. 1. The device can further comprise a cap to protect the nozzle. The nozzle and the retainer are sealed; and the retainer and the pump are also sealed, as shown in FIG. 2. The poppet valve lifted by the retainer always contacts the nozzle, so there is no clearance between the nozzle and the poppet valve. This reduces a potential risk that powder prefilled in the nozzle falls into the pump. The retainer has a tray to trap powder fallen from the nozzle, as shown in FIG. 3. This reduces a potential risk that powder from the nozzle falls into the pump. FIG. 4 illustrates the main flow to deliver powder and a side air flow to deliver trapped powder through the nozzle. If necessary, the pump may be activated up to 3 times to deliver powder. Air-intake holes in the retainer prevent the remaining powder in the nozzle from entering to the pump when the pump returns to the original form. FIG. 5 illustrates measurements of the parts. The width of the thread of the pump "a" is 10.1-10.7 mm, and can be extended by 0.4 mm shorter or longer, in order to minimize the risk of insufficient seal between the retainer and the pump, and between the nozzle and the retainer.

Design Features of the Parts

The nozzle has no undercut structure and makes it convenient to manufacture with a multi-cavity mold. The pump has no air-intake hole, which eliminates a piercing process from manufacturing the pump. The retainer is added to hold the poppet valve on the nozzle and has air-intake function. These features are very effective for high-volume production, leading to high manufacturability. Additionally, the poppet valve is immobilized with the retainer and the nozzle, to further increase the delivery performance of the device. Furthermore, the outlet hole size of the nozzle is adapted to suit powder formulations with large particles.

Material and Color of the Parts

Nozzle: Cyclic olefin copolymer, Blue,
Poppet valve: Cyclic olefin copolymer, Clear
Retainer: Cyclic olefin copolymer, Clear,
Pump: Low Density Polyethylene, White,
Cap: Polypropylene, Clear, Example 2

Delivery Performance Test

Figure 6:
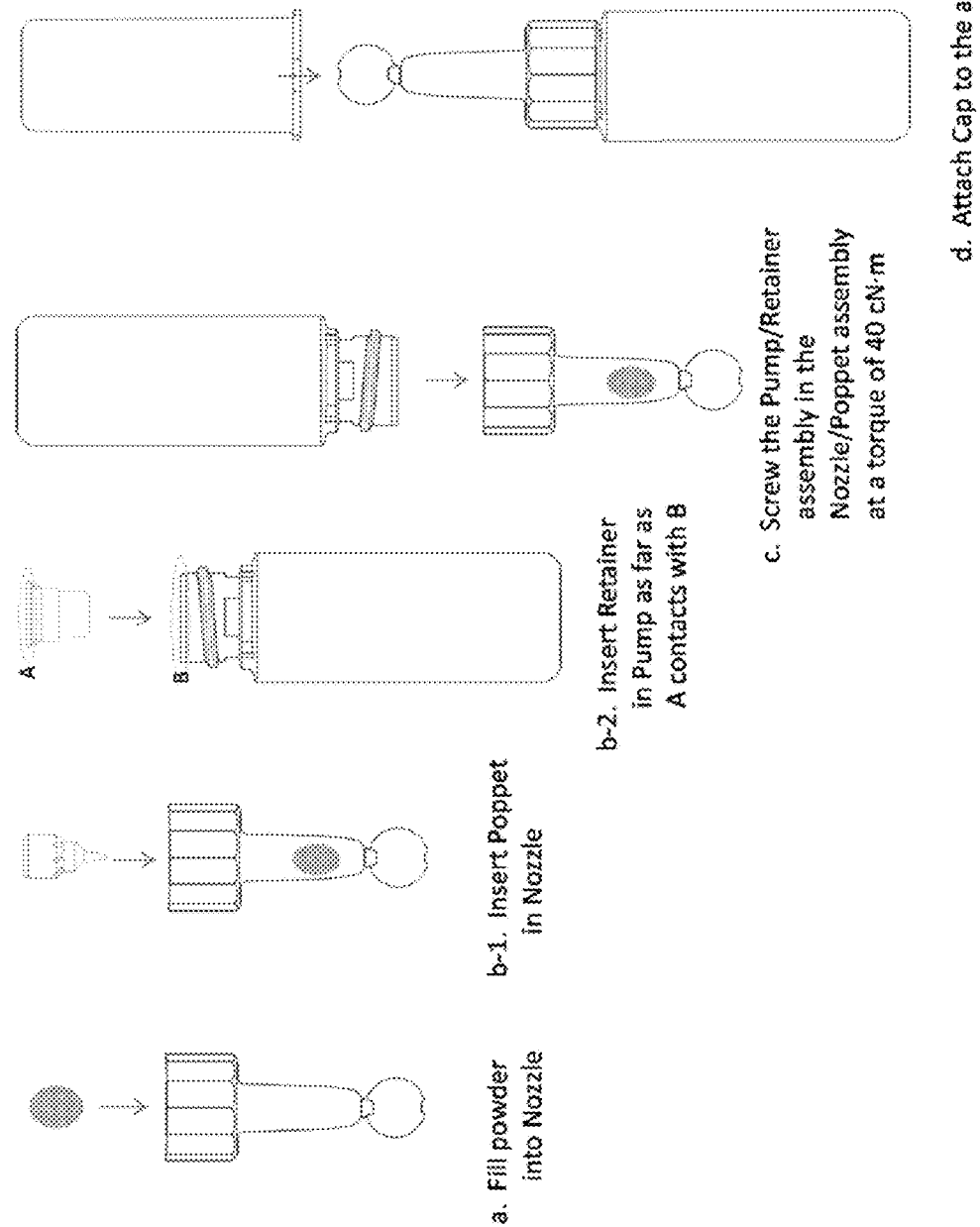
FIG. 6 illustrates an assembly procedure of the device.

According to the assembly procedure as illustrated in FIG. 6, 60 assembled devices filled with 15 mg (±0.8 mg) of placebo (composing tribasic calcium phosphate and two types of microcrystalline cellulose) were prepared and packaged into aluminum pouches (1 device/aluminum pouch). Thirty of the pouched devices were subject to delivery testing under normal condition (without climatic and transit conditioning). The remaining 30 pouched devices were packed into 5 cartons (6 devices/carton) into a box. The nozzle top of device was oriented to the top of the box. The box was subject to climatic and transit conditioning followed by delivery testing.

Climatic and transit conditioning was conducted as follows. In order to subject the test samples under extreme environmental conditions, according to ASTM's Standard Practice for Conditioning Containers, Packages, or Packaging Components for Testing (ASTM D4332-01), the test samples were stored at −30° C. for 24 hours (extreme cold condition), at 40° C./90% RH for 24 hours (tropical condition), and at 60° C./15% RH for 24 hours (desert condition), in the order listed. After the climatic conditioning, in order to subject the test samples under extreme shipping/distribution conditions, according to ASTM's Standard Practice for Performance Testing of Shipping Containers and Systems (ASTM D4169-14) and its related ASTM's standards, the test samples were exposed to impacts, in sequence and in the order listed, to the initial manual handling impact (ASTM D5276-98), the loose-load vibration impact (ASTM D999-08), the vehicle vibration impact based on both truck and air transits (D4728-06), and the final manual handling impact (ASTM D5276-98). The sequence was specified in Distribution Cycle 2 of ASTM D4169-14. Additionally, all assurance levels of these impacts were set at Assurance Level II, which is mostly employed for medical devices.

For delivery testing, after removal of the aluminum pouch and cap, the device was weighed and then actuated 3 times by an automated actuator (Vereo DSx, Proveris Scientific Corp.) using parameters based on actual human actuation manner. The device weight was measured after actuation, and the delivered weight was calculated by the following equation:

$$\text{Delivered Weight (\%)} = \frac{\text{device weight before actuation (mg)} - \text{device weight after actuation (mg)}}{15 \text{ (mg)}} \times 100$$

Figure 7:
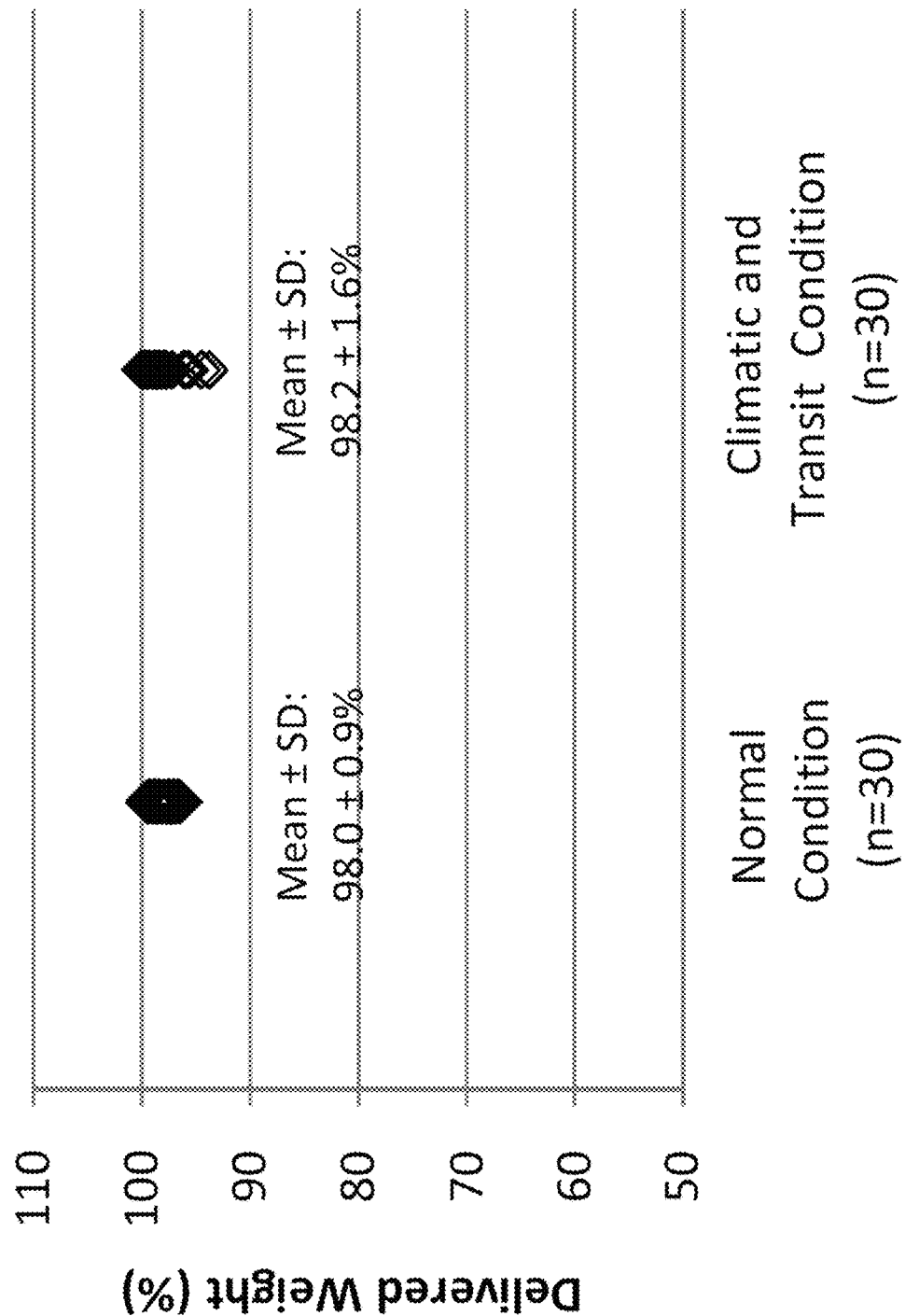
FIG. 7 illustrates delivered weight amounts of placebo under a normal condition and after climatic and transit conditioning in a delivery performance test of the device.

The results of delivered weight under normal condition and after the climatic and transit conditioning are shown in FIG. 7. There is no remarkable difference between the delivered weights under normal condition (mean±SD: 98.0±0.9%, min: 96.5%, max: 99.4%) and those after the climatic and transit conditioning (mean±SD: 98.2±1.6%, min: 93.8%, max: 100.1%).

Example 3

Use of the Device

After taking the device out of a package, a subject operates the device by removing the protective cap, tearing away the tip tab of the nozzle, positioning the nozzle at least partially within a nostril of the subject, and manually actuating the pump 1, 2, or 3 times to expel a powdered therapeutic formulation that is prefilled in the nozzle.

Example 4

Treatment

A device disclosed herein is used to deliver a powdered therapeutic formulation that comprises an effective amount of an active agent for the treatment or prevention of a disease or a condition in a subject in need thereof. The disease or condition can be pain, hormone disorder, a headache, amyotrophic lateral sclerosis, Parkinson's disease, stress, anxiety, nausea, emesis, aggression, pain, neuropathic pain, sleeplessness, insomnia, restless leg syndrome, depression, or any combination thereof. The powdered therapeutic formulation can be administered 1 time, 2 times, 3 times, 4 times, 5 times, 6 times, 7 times, or 8 times daily. The powdered therapeutic formulation can be in a single unit dose. The powdered therapeutic formulation can be a unit dose of about 5 mg to about 50 mg, for example about: 15, 20, 25, or 30 mg. A unit dosage of the powdered therapeutic formulation can contain about 0.1 mg to about 25 mg of the active agent, for example about: 2, 4, 6, or 8 mg.

While some cases and instances have been shown and described herein, it will be obvious to those skilled in the art that such disclosure are provided by way of example only. Numerous variations, changes, and substitutions will now occur to those skilled in the art without departing from devices, methods and formulations described herein. It should be understood that various alternatives to the instances described herein can be employed in practicing devices, methods and formulations described herein. It is intended that the following claims define the scope of methods, formulations and devices and that methods, formulations, and devices within the scope of these claims and their equivalents be covered thereby.

What is claimed is:

1. A device for delivering a therapeutic formulation, wherein the device comprises:
   a nozzle having a reservoir disposed within the nozzle,
   a valve comprising a conical section,
   a hollow retainer, and
   a manual air pump,
      wherein the reservoir has the therapeutic formulation disposed therein,
      wherein the conical section protrudes into a lower end of the reservoir and an outer portion of the conical section contacts the therapeutic formulation,
      wherein the manual air pump is operably linked to an upstream end of the nozzle and a downstream end of the retainer,
      wherein the valve is at least partially fit into the reservoir, and has one or more contacting points with the retainer that immobilizes the valve, and
      wherein the valve prevents movement of the therapeutic formulation into the manual air pump and regulates a flow of air.

2. The device of claim 1, wherein the one or more contacting points are one or more inner ribs.

3. The device of claim 1, wherein the retainer has an inner circumferential groove based from an upstream end of the retainer.

4. The device of claim 3, wherein a rim of the circumferential groove of the retainer is in contact with the one or more contacting points of the valve.

5. The device of claim 1, wherein the therapeutic formulation comprises a powdered therapeutic formulation.

6. The device of claim 5, wherein the powdered therapeutic formulation comprises dihydroergotamine (DHE) or a pharmaceutically acceptable salt thereof.

7. The device of claim 6, wherein the pharmaceutically acceptable salt of dihydroergotamine is dihydroergotamine mesylate.

8. The device of claim 1, wherein the device is a single-use device.

9. The device of claim 1, wherein the valve has one or more surface grooves.

10. The device of claim 9, wherein the valve has about 3 to about 20 surface grooves.

11. The device of claim 10, wherein the valve has about 8 surface grooves.

12. The device of claim 1, wherein the valve has about 2 to about 10 inner ribs.

13. The device of claim 12, wherein the valve has about 3 inner ribs.

14. The device of claim 1, wherein the valve comprises a cavity.

15. The device of claim 1, wherein the retainer contains an outer circumferential rim that is wider than an opening of the manual air pump.

16. The device of claim 1, wherein the retainer has two air intake holes.

17. The device of claim 1, wherein the retainer is at least partially fit into the manual air pump.

18. The device of claim 1, wherein the nozzle immobilizes the valve.

19. The device of claim 18, wherein the manual air pump immobilizes the valve.

20. A method of using a device to deliver a powdered therapeutic formulation to a subject in need thereof, wherein the device comprises:
    a nozzle having a reservoir disposed within the nozzle,
    a valve comprising a conical section,
    a hollow retainer, and
    a manual air pump,
        wherein the reservoir has the powedered therapeutic formulation disposed therein,
        wherein the conical section protrudes into a lower end of the reservoir and an outer portion of the conical section contacts the powedered therapeutic formulation,
        wherein the manual air pump is operably linked to an upstream end of the nozzle and a downstream end of the retainer,
        wherein the valve is at least partially fit into the reservoir, and has one or more contacting points with the retainer that immobilizes the valve, and
        wherein the valve prevents movement of the powedered therapeutic formulation into the manual air pump and regulates a flow of air, and
    the method comprising:
        positioning the nozzle of the device at least partially into a nostril of the subject and activating the manual air pump.

21. The method of claim 20, wherein the method treats a disease or condition of the subject.

22. The method of claim 21, wherein the disease or condition is a migraine.

23. A method of manufacturing a device, wherein the device comprises:
    a nozzle having a reservoir disposed within the nozzle,
    a valve comprising a conical section,
    a hollow retainer, and
    a manual air pump,
        wherein the reservoir has a therapeutic formulation disposed therein,
        wherein the conical section protrudes into a lower end of the reservoir and an outer portion of the conical section contacts the therapeutic formulation,
        wherein the manual air pump is operably linked to an upstream end of the nozzle and a downstream end of the retainer,
        wherein the valve is at least partially fit into the reservoir, and has one or more contacting points with the retainer that immobilizes the valve, and
        wherein the valve prevents movement of the therapeutic formulation into the manual air pump and regulates a flow of air, and
    the method comprising:
        inserting the valve in the nozzle,
        inserting the retainer in the manual air pump, and
        coupling the manual air pump to the nozzle.

24. A device for delivering a therapeutic formulation, wherein the device comprises:
    a nozzle having a reservoir disposed within the nozzle,
    an airflow regulator comprising a conical section,
    a hollow retainer, and
    a manual air pump,
        wherein the manual air pump is operably linked to an upstream end of
        the nozzle and a downstream end of the retainer,
        the reservoir has the therapeutic formulation disposed therein,
        the conical section protrudes into a lower end of the reservoir and an outer portion of the conical section contacts the therapeutic formulation,
        the airflow regulator is at least partially fit into the reservoir, and has one or more contacting points with the retainer that immobilizes the airflow regulator, and
        the airflow regulator prevents movement of the therapeutic formulation into the manual air pump.

* * * * *